United States Patent
Kang et al.

(10) Patent No.: US 10,676,727 B2
(45) Date of Patent: Jun. 9, 2020

(54) POLYPEPTIDES HAVING TREHALASE ACTIVITY AND THE USE THEREOF IN PROCESS OF PRODUCING FERMENTATION PRODUCTS

(71) Applicant: NOVOZYMES A/S, Bagsvaerd (DK)

(72) Inventors: Zhengfang Kang, Raleigh, NC (US); Kirk Matthew Schnorr, Holte (DK); Lar Kobberøe Skov, Ballerup (DK)

(73) Assignee: NOVOZYMES A/S, Bagsvaerd (DK)

( * ) Notice: Subject to any disclaimer, the term of this patent is extended or adjusted under 35 U.S.C. 154(b) by 108 days.

(21) Appl. No.: 15/579,349

(22) PCT Filed: Jun. 13, 2016

(86) PCT No.: PCT/US2016/037224
§ 371 (c)(1),
(2) Date: Dec. 4, 2017

(87) PCT Pub. No.: WO2016/205127
PCT Pub. Date: Dec. 22, 2016

(65) Prior Publication Data
US 2018/0179504 A1    Jun. 28, 2018

Related U.S. Application Data

(60) Provisional application No. 62/181,538, filed on Jun. 18, 2015.

(51) Int. Cl.
| | | |
|---|---|---|
| *C12N 15/82* | (2006.01) | |
| *C12N 9/24* | (2006.01) | |
| *C12P 7/06* | (2006.01) | |
| *C12P 7/10* | (2006.01) | |

(52) U.S. Cl.
CPC .............. *C12N 9/2402* (2013.01); *C12P 7/06* (2013.01); *C12P 7/10* (2013.01); *C12Y 302/01028* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | | | |
|---|---|---|---|---|
| 2015/0079627 A1* | 3/2015 | Rasmussen | ............. | C12P 19/14 435/43 |
| 2017/0088861 A1* | 3/2017 | Andrei | ...................... | C12N 9/88 |
| 2018/0073041 A1* | 3/2018 | Rasmussen | ............. | C12P 19/14 |

FOREIGN PATENT DOCUMENTS

| | | | | |
|---|---|---|---|---|
| WO | 2009/121058 A1 | 10/2009 | | |
| WO | WO-2009121058 A1 * | 10/2009 | ................ | C12P 7/06 |
| WO | 2012/027374 A2 | 3/2012 | | |
| WO | WO-2012027374 A2 * | 3/2012 | ............. | A21D 8/042 |
| WO | 2013/148993 A1 | 10/2013 | | |
| WO | WO-2014028434 A2 * | 2/2014 | | |
| WO | WO-2014028436 A1 * | 2/2014 | | |
| WO | 2015/065978 A1 | 5/2015 | | |

OTHER PUBLICATIONS

Berka et al. (Nature Biotechnology; 29:922-927; Published Jan. 1, 2011; IDS).*
Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495,1994).*
Thornton et al. (Nature structural Biology, structural genomics supplement, Nov. 2000).*
Keskin et al. (Protein Science, 13:1043-1055, 2004).*
Smith et al. (Nature Biotechnology, 15:1222-1223, 1997).*
Bork et al. (TIG, 12:425-427, 1996).*
Doerks et al., (TIG, 14:248-250, 1998).*
Maniatis et al. (Molecular Cloning: A Laboratory Manual, Cold Spring Harbor Laboratory, 1982; see in particular pp. 387-389).*
McConnell et al. (Nature, 411:709-713, 2001).*
Hanzawa et al. (PNAS, 102:7748-7753, 2005).*
Wishart et al. (JBC, 270:26782-26785, 1995).*
Kaur et al. (Pesticide Biochemistry and Physiology, 116:89-93, 2014).*
Da Lage et al. (Biologia, Bratislava, 57/Suppl. 11:181-189, 2002).*
Hostinvova' et al. (Biologia 65/4: 559-568, 2010).*
Aeschbacher et al, 1999, Plant Physiol 119, 489-496.
Amaral et al, 1996, Can J Microbiol 41, 1057-1062.
Berka et al, 2011, Nature Biotechnol 29(10), 922-927.
Berka et al, 2016, UniProt No. G2PZS2.
Berka et al, 2016, UniProt No. G2RDT9.
Cardello et al, 1994, Microbiology 140, 1671-1677.
D'Enfert et al, 1997, Mol Microbiol 24, 203-216.
Dewerchin et al, 1984, J Bacteriol 158, 575-579.
Grba et al, 1975, Eur J Appl Microbiol 2, 29-37.
Hecker et al, 1973, J Bacteriol 115, 592-599.
Kadowaki et al, 1996, Biochim Biophys Acta 1291, 199-205.
Londesborouh et al, 1984, Biochem J 219, 511-518.
Parvaeh et al, 1996, FEBS Lett 391, 273-278.
Sumida et al, 1989, J Ferm Bioeng 67, 83-86.
Thevelein et al, 1983, J Gen Microbiol 129, 719-726.
Zimmermann et al, 1990, Biochim Biophys Acta 1036, 41-46.

* cited by examiner

*Primary Examiner* — Vinod Kumar
(74) *Attorney, Agent, or Firm* — David Fazzolare

(57) ABSTRACT

The present invention relates to polypeptides having trehalase activity. The invention also relates to nucleic acid constructs, vectors, and host cells comprising the polynucleotides as well as methods of producing and using a trehalase of the invention, in particular a process of producing a fermentation product, such as ethanol.

14 Claims, 2 Drawing Sheets
Specification includes a Sequence Listing.

SEQUENCE LISTING

<160> NUMBER OF SEQ ID NOS: 32

<210> SEQ ID NO 1
<211> LENGTH: 3317
<212> TYPE: DNA
<213> ORGANISM: Myceliophthora sepedonium
<220> FEATURE:
<221> NAME/KEY: sig_peptide
<222> LOCATION: (501)..(560)
<220> FEATURE:
<221> NAME/KEY: CDS
<222> LOCATION: (501)..(679)
<220> FEATURE:
<221> NAME/KEY: Intron
<222> LOCATION: (680)..(765)
<220> FEATURE:
<221> NAME/KEY: CDS
<222> LOCATION: (766)..(1425)
<220> FEATURE:
<221> NAME/KEY: Intron
<222> LOCATION: (1426)..(1483)
<220> FEATURE:
<221> NAME/KEY: CDS
<222> LOCATION: (1484)..(2676)
<220> FEATURE:
<221> NAME/KEY: Intron
<222> LOCATION: (2677)..(2755)
<220> FEATURE:
<221> NAME/KEY: CDS
<222> LOCATION: (2756)..(2814)

<400> SEQUENCE: 1

```
aaagattgga agccactgct taaagatggc aatcaccagg ctcgcttctc gattcccaaa      60
gcggtgaaaa cacaaaaaag ttggagaagc gacgatcatg atcaagtagc ccctgctcga     120
gcgggaaggg cccagccttg gatccaggca tcaccccgtt actacttac gtatagagct      180 gcagcttcct gcaagcatgg ttacatgtgc agcttgtcaa ggcccctcga gagcttgcca     240
gaagggttcg gtctgttccc caagccgtat cgggagctaa gacggacatc cttcaatccg     300
attttgaagc ccggccgagc cggctcgttt ggctcctcag tctcccaatg catctgggct     360
gcagacagct tctctcgttt taaaaagcct gagcattccc tgccctcctc ggggccttcc     420
tcgttctctc ccatccttcg ggtacaacag accatcatcg taagcgcaag acagcaccac     480
cgcgtgctga aagctacaca atg gcg cta cga cac atc gcg gcg gcg gcg atc     533
                       Met Ala Leu Arg His Ile Ala Ala Ala Ala Ile
                         1               5                   10 gcc ggt ctt gcc tca agg act gca gcg ctg tac atc aat ggc tca gtc     581
Ala Gly Leu Ala Ser Arg Thr Ala Ala Leu Tyr Ile Asn Gly Ser Val
             15                  20                  25 aca gcg ccg tgc gac tcg ccc att tac tgc caa ggc gag ctt cta aaa     629
Thr Ala Pro Cys Asp Ser Pro Ile Tyr Cys Gln Gly Glu Leu Leu Lys
         30                  35                  40 gcg gtt gaa ctg gcg cgt cct ttc gtt gac agc aag aca ttt gtg gac     677
Ala Val Glu Leu Ala Arg Pro Phe Val Asp Ser Lys Thr Phe Val Asp
     45                  50                  55 at gtaagtcatg atcggccagc caggtgggaa tgcagccggc gggcagattc            729
Met
 60 gtggtgacac actgactgac ttggattccc gcccag g ccc acg atc aag cca gtg    784
                                        Pro Thr Ile Lys Pro Val
                                                           65 gat gaa gtg ctt gca gca ttc agc aag ctt agc cta cca ctt tcc aat     832
Asp Glu Val Leu Ala Ala Phe Ser Lys Leu Ser Leu Pro Leu Ser Asn
         70                  75                  80 aac tca gag ctc aac gcc ttg tat gag aac ttc gcc cag gct ggc         880
Asn Ser Glu Leu Asn Ala Leu Tyr Glu Asn Phe Ala Gln Ala Gly
```

```
                Asn Ser Glu Leu Asn Ala Phe Leu Tyr Glu Asn Phe Ala Gln Ala Gly
                        85                  90                  95 cac gag ctc gaa gaa gtg ccc gac agt gag cta gag acg gac gca aag         928
His Glu Leu Glu Glu Val Pro Asp Ser Glu Leu Glu Thr Asp Ala Lys
100                 105                 110 ttc ctc gac aag ctc gag gat cgc acc atc aag gag ttc gtc ggc aag         976
Phe Leu Asp Lys Leu Glu Asp Arg Thr Ile Lys Glu Phe Val Gly Lys
115                 120                 125                 130 gtg atc gac atc tgg ccc gac ttg acc agg cgc tat gcc ggc ccc agc        1024
Val Ile Asp Ile Trp Pro Asp Leu Thr Arg Arg Tyr Ala Gly Pro Ser
                135                 140                 145 aac tgc acc gag tgc gcc aac agc ttc att ccc gtg aac cgc acg ttc        1072
Asn Cys Thr Glu Cys Ala Asn Ser Phe Ile Pro Val Asn Arg Thr Phe
            150                 155                 160 gtc gtg gct ggc ggt cgc ttc cga gag ccc tac tat tgg gat tcg tac        1120
Val Val Ala Gly Gly Arg Phe Arg Glu Pro Tyr Tyr Trp Asp Ser Tyr
        165                 170                 175 tgg atc gtc gaa ggt ctc ctg cgc act ggc ggt gcc ttc acc cat atc        1168
Trp Ile Val Glu Gly Leu Leu Arg Thr Gly Gly Ala Phe Thr His Ile
180                 185                 190 tcc aag aac atc att gag aac ttc ctg gac ttt gtc gac acg att ggc        1216
Ser Lys Asn Ile Ile Glu Asn Phe Leu Asp Phe Val Asp Thr Ile Gly
195                 200                 205                 210 ttc att ccc aat ggc gcc agg atc tac tac ctg aac agg tca cag ccc        1264
Phe Ile Pro Asn Gly Ala Arg Ile Tyr Tyr Leu Asn Arg Ser Gln Pro
                215                 220                 225 cct ctc ctg aca ttg atg gtg aag agc tac gtc gac tac acc aac gac        1312
Pro Leu Leu Thr Leu Met Val Lys Ser Tyr Val Asp Tyr Thr Asn Asp
            230                 235                 240 acg agc atc ctg gac agg gcc ttg ccg ctg ctg atc aag gag cac gag        1360
Thr Ser Ile Leu Asp Arg Ala Leu Pro Leu Leu Ile Lys Glu His Glu
        245                 250                 255 ttc ttc atg aat aac cgg acg gtg tcc atc acg gga tcg aac ggc aag        1408
Phe Phe Met Asn Asn Arg Thr Val Ser Ile Thr Gly Ser Asn Gly Lys
260                 265                 270 gag tac act ctg aac ag gtaagcgagg tggacaggca ggcctcggcg                1455
Glu Tyr Thr Leu Asn Arg
275                 280 accatgcgct tattgttgta tctggcag g tat cac gtt gaa aac aac caa cca       1508
                              Tyr His Val Glu Asn Asn Gln Pro
                                                      285 cgc cca gag tcg ttc cgg gag gat tac att acc gct aac aac ggc tcc        1556
Arg Pro Glu Ser Phe Arg Glu Asp Tyr Ile Thr Ala Asn Asn Gly Ser
        290                 295                 300 tac tac gcg tct tcg ggc ata ata tat ccc gtt aag acg ccc ctc aac        1604
Tyr Tyr Ala Ser Ser Gly Ile Ile Tyr Pro Val Lys Thr Pro Leu Asn
305                 310                 315                 320 gag acg gaa aag gcc gcg ctc tac tcg aac cta gca acc ggc gcc gag        1652
Glu Thr Glu Lys Ala Ala Leu Tyr Ser Asn Leu Ala Thr Gly Ala Glu
                325                 330                 335 tcc ggc tgg gac tac acc tcc cga tgg ctt ggg gtc ccc agc gac gct        1700
Ser Gly Trp Asp Tyr Thr Ser Arg Trp Leu Gly Val Pro Ser Asp Ala
            340                 345                 350 gcg agg gac gtc tat ttc ccg ctc cgc tcg ctt aat gtc cgc gac ata        1748
Ala Arg Asp Val Tyr Phe Pro Leu Arg Ser Leu Asn Val Arg Asp Ile
        355                 360                 365 gtc ccc gtc gat ctc aac tcc atc ctc tac cag aac gag gtg atc att        1796
Val Pro Val Asp Leu Asn Ser Ile Leu Tyr Gln Asn Glu Val Ile Ile
370                 375                 380
```

```
                                                             -continued gcc gag tac ctc gag aag gcc ggt aac tcc tcc gcg gcc aag cgc ttc      1844
Ala Glu Tyr Leu Glu Lys Ala Gly Asn Ser Ser Ala Ala Lys Arg Phe
385                 390                 395                 400 gcc act gct gcc gaa cag cgc agc gag gcc atg tac tcc ctc atg tgg      1892
Ala Thr Ala Ala Glu Gln Arg Ser Glu Ala Met Tyr Ser Leu Met Trp
            405                 410                 415 aac gcc acg cac tgg tct tac ttt gac tac aat ctg acc gat aac acg      1940
Asn Ala Thr His Trp Ser Tyr Phe Asp Tyr Asn Leu Thr Asp Asn Thr
420                 425                 430 caa cac atc ttc gtc cca gcc gac gag gac acc gcc ccc cag gac cgg      1988
Gln His Ile Phe Val Pro Ala Asp Glu Asp Thr Ala Pro Gln Asp Arg
        435                 440                 445 atc gag gcc ccc ccc ggt caa caa gtc ttc ttc cac att gcg cag ctc      2036
Ile Glu Ala Pro Pro Gly Gln Gln Val Phe Phe His Ile Ala Gln Leu
450                 455                 460 tat cca ttc tgg acg ggc gcg gcc ccc gcc agc ctt aag gct aac ccc      2084
Tyr Pro Phe Trp Thr Gly Ala Ala Pro Ala Ser Leu Lys Ala Asn Pro
465                 470                 475                 480 ctc gcg gtg cag caa gcc tac gcc cgt gtg gcg cgc atg ctc gat atc      2132
Leu Ala Val Gln Gln Ala Tyr Ala Arg Val Ala Arg Met Leu Asp Ile
            485                 490                 495 aag aag ggc gcc atc ccc gcc acc aac tac cgc acc ggc caa caa tgg      2180
Lys Lys Gly Ala Ile Pro Ala Thr Asn Tyr Arg Thr Gly Gln Gln Trp
500                 505                 510 gac cag ccc aac gtc tgg ccg ccg ctg caa cat atc ctg atg aag ggc      2228
Asp Gln Pro Asn Val Trp Pro Pro Leu Gln His Ile Leu Met Lys Gly
        515                 520                 525 ctg ctt aac acc ccg gca acc ttt ggc aag tcc gac cct gcg tac cag      2276
Leu Leu Asn Thr Pro Ala Thr Phe Gly Lys Ser Asp Pro Ala Tyr Gln
530                 535                 540 agc gtg caa aac ctc gcc ctg cgt ctc gcc cag cgc tac ctc gat tcc      2324
Ser Val Gln Asn Leu Ala Leu Arg Leu Ala Gln Arg Tyr Leu Asp Ser
545                 550                 555                 560 acc ttt tgt acc tgg tac gcc acg ggc ggt tca acc agc gac ttc ccg      2372
Thr Phe Cys Thr Trp Tyr Ala Thr Gly Gly Ser Thr Ser Asp Phe Pro
            565                 570                 575 cag ctg gag ggt gtt acc ccg ggc gct acg ggc gtc atg ttt gag aag      2420
Gln Leu Glu Gly Val Thr Pro Gly Ala Thr Gly Val Met Phe Glu Lys
580                 585                 590 tac gcc gac aat gct acc aac gtt gcc ggc ggc ggc gaa tac gag          2468
Tyr Ala Asp Asn Ala Thr Asn Val Ala Gly Gly Gly Glu Tyr Glu
        595                 600                 605 gtc gtc gag ggt ttc ggg tgg acc aat ggc gta ctg atc tgg gcg gcc      2516
Val Val Glu Gly Phe Gly Trp Thr Asn Gly Val Leu Ile Trp Ala Ala
610                 615                 620 gac gtc ttt ggt aac aag ctc aag cgc ccg gac tgc ggc aac atc acg      2564
Asp Val Phe Gly Asn Lys Leu Lys Arg Pro Asp Cys Gly Asn Ile Thr
625                 630                 635                 640 gcc gca cat acc cac tct agt gcc aag aga ggt ctg gaa gag aat aag      2612
Ala Ala His Thr His Ser Ser Ala Lys Arg Gly Leu Glu Glu Asn Lys
            645                 650                 655 ctg ccg agg agg gcg gtg gag ctc gac ccg tgg gat gcc gcg tgg acc      2660
Leu Pro Arg Arg Ala Val Glu Leu Asp Pro Trp Asp Ala Ala Trp Thr
            660                 665                 670 aag atg ttt ggg cgg a gtaagctccg gagaagagag gcagaagatg tgcggaagcg    2716
Lys Met Phe Gly Arg
            675 gtggatgagc taaggtccta atccatatgc ttaatgaag gg  tgg ttc gtt gtg       2769
                                              Arg Trp Phe Val Val
                                              680
```

```
ctt cgc ttt caa gtt ggt aac tta gtg ttt agt gtc tcc gtc tcg      2814
Leu Arg Phe Gln Val Gly Asn Leu Val Phe Ser Val Ser Val Ser
        685                 690                 695 taagcgatgg caaactttgc gagggaagtc ggtcgatgaa gaggtaatcc gcatcctggc  2874
gccctatcta ggtcggtagc tacctgggcg gatatcgagc ttacattaat acctactag  2934 taatttccag agagatgatc acctggattg cggctgcaaa tggttaacac acacaataag  2994
ataagaatgt tattgctgcc catgtacaga cacggttgta gaatgagctt gataaagctg  3054
acaacggaaa actggacccc ccggtttgcg cataaatgtc ccgccaacgc caaaagttca  3114
accctccaac cgccaccgta gcaacgccga tacaaatgca accgtgtatt ttctccgtca  3174
tgccgccgta gcccctattc acacactcgg ctcaaaccgc tgtcgtcacc ggcgtgcccc  3234
gacacgcctc ccaatccgac ccagaggcct accccggcgc cgtgtgacga tgggcgtccc  3294
ccccagctca ctgccctcac ccc                                         3317
```

<210> SEQ ID NO 2
<211> LENGTH: 697
<212> TYPE: PRT
<213> ORGANISM: Myceliophthora sepedonium

<400> SEQUENCE: 2

```
Met Ala Leu Arg His Ile Ala Ala Ala Ile Ala Gly Leu Ala Ser
  1               5                  10                  15

Arg Thr Ala Ala Leu Tyr Ile Asn Gly Ser Val Thr Ala Pro Cys Asp
                 20                  25                  30

Ser Pro Ile Tyr Cys Gln Gly Glu Leu Leu Lys Ala Val Glu Leu Ala
             35                  40                  45

Arg Pro Phe Val Asp Ser Lys Thr Phe Val Asp Met Pro Thr Ile Lys
         50                  55                  60

Pro Val Asp Glu Val Leu Ala Ala Phe Ser Lys Leu Ser Leu Pro Leu
 65                  70                  75                  80

Ser Asn Asn Ser Glu Leu Asn Ala Phe Leu Tyr Glu Asn Phe Ala Gln
                 85                  90                  95

Ala Gly His Glu Leu Glu Glu Val Pro Asp Ser Glu Leu Glu Thr Asp
            100                 105                 110

Ala Lys Phe Leu Asp Lys Leu Glu Asp Arg Thr Ile Lys Glu Phe Val
        115                 120                 125

Gly Lys Val Ile Asp Ile Trp Pro Asp Leu Thr Arg Arg Tyr Ala Gly
    130                 135                 140

Pro Ser Asn Cys Thr Glu Cys Ala Asn Ser Phe Ile Pro Val Asn Arg
145                 150                 155                 160

Thr Phe Val Val Ala Gly Gly Arg Phe Arg Glu Pro Tyr Tyr Trp Asp
                165                 170                 175

Ser Tyr Trp Ile Val Glu Gly Leu Leu Arg Thr Gly Gly Ala Phe Thr
            180                 185                 190

His Ile Ser Lys Asn Ile Ile Glu Asn Phe Leu Asp Phe Val Asp Thr
        195                 200                 205

Ile Gly Phe Ile Pro Asn Gly Ala Arg Ile Tyr Tyr Leu Asn Arg Ser
    210                 215                 220

Gln Pro Pro Leu Leu Thr Leu Met Val Lys Ser Tyr Val Asp Tyr Thr
225                 230                 235                 240

Asn Asp Thr Ser Ile Leu Asp Arg Ala Leu Pro Leu Leu Ile Lys Glu
                245                 250                 255
```

-continued

```
His Glu Phe Phe Met Asn Asn Arg Thr Val Ser Ile Thr Gly Ser Asn
            260                 265                 270

Gly Lys Glu Tyr Thr Leu Asn Arg Tyr His Val Glu Asn Asn Gln Pro
        275                 280                 285

Arg Pro Glu Ser Phe Arg Glu Asp Tyr Ile Thr Ala Asn Asn Gly Ser
        290                 295                 300

Tyr Tyr Ala Ser Ser Gly Ile Ile Tyr Pro Val Lys Thr Pro Leu Asn
305                 310                 315                 320

Glu Thr Glu Lys Ala Ala Leu Tyr Ser Asn Leu Ala Thr Gly Ala Glu
            325                 330                 335

Ser Gly Trp Asp Tyr Thr Ser Arg Trp Leu Gly Val Pro Ser Asp Ala
            340                 345                 350

Ala Arg Asp Val Tyr Phe Pro Leu Arg Ser Leu Asn Val Arg Asp Ile
            355                 360                 365

Val Pro Val Asp Leu Asn Ser Ile Leu Tyr Gln Asn Glu Val Ile Ile
            370                 375                 380

Ala Glu Tyr Leu Glu Lys Ala Gly Asn Ser Ser Ala Ala Lys Arg Phe
385                 390                 395                 400

Ala Thr Ala Ala Glu Gln Arg Ser Glu Ala Met Tyr Ser Leu Met Trp
            405                 410                 415

Asn Ala Thr His Trp Ser Tyr Phe Asp Tyr Asn Leu Thr Asp Asn Thr
            420                 425                 430

Gln His Ile Phe Val Pro Ala Asp Glu Asp Thr Ala Pro Gln Asp Arg
            435                 440                 445

Ile Glu Ala Pro Pro Gly Gln Gln Val Phe Phe His Ile Ala Gln Leu
450                 455                 460

Tyr Pro Phe Trp Thr Gly Ala Ala Pro Ala Ser Leu Lys Ala Asn Pro
465                 470                 475                 480

Leu Ala Val Gln Gln Ala Tyr Ala Arg Val Ala Arg Met Leu Asp Ile
            485                 490                 495

Lys Lys Gly Ala Ile Pro Ala Thr Asn Tyr Arg Thr Gly Gln Gln Trp
            500                 505                 510

Asp Gln Pro Asn Val Trp Pro Pro Leu Gln His Ile Leu Met Lys Gly
            515                 520                 525

Leu Leu Asn Thr Pro Ala Thr Phe Gly Lys Ser Asp Pro Ala Tyr Gln
530                 535                 540

Ser Val Gln Asn Leu Ala Leu Arg Leu Ala Gln Arg Tyr Leu Asp Ser
545                 550                 555                 560

Thr Phe Cys Thr Trp Tyr Ala Thr Gly Gly Ser Thr Ser Asp Phe Pro
            565                 570                 575

Gln Leu Glu Gly Val Thr Pro Gly Ala Thr Gly Val Met Phe Glu Lys
            580                 585                 590

Tyr Ala Asp Asn Ala Thr Asn Val Ala Gly Gly Gly Glu Tyr Glu
            595                 600                 605

Val Val Glu Gly Phe Gly Trp Thr Asn Gly Val Leu Ile Trp Ala Ala
            610                 615                 620

Asp Val Phe Gly Asn Lys Leu Lys Arg Pro Asp Cys Gly Asn Ile Thr
625                 630                 635                 640

Ala Ala His Thr His Ser Ser Ala Lys Arg Gly Leu Glu Glu Asn Lys
            645                 650                 655

Leu Pro Arg Arg Ala Val Glu Leu Asp Pro Trp Asp Ala Ala Trp Thr
            660                 665                 670

Lys Met Phe Gly Arg Arg Trp Phe Val Val Leu Arg Phe Gln Val Gly
```

-continued

```
            675                 680                 685
Asn Leu Val Phe Ser Val Ser Val Ser
    690                 695

<210> SEQ ID NO 3
<211> LENGTH: 3204
<212> TYPE: DNA
<213> ORGANISM: Chaetomium virescens
<220> FEATURE:
<221> NAME/KEY: CDS
<222> LOCATION: (501)..(679)
<220> FEATURE:
<221> NAME/KEY: sig_peptide
<222> LOCATION: (501)..(560)
<220> FEATURE:
<221> NAME/KEY: Intron
<222> LOCATION: (680)..(751)
<220> FEATURE:
<221> NAME/KEY: CDS
<222> LOCATION: (752)..(1411)
<220> FEATURE:
<221> NAME/KEY: Intron
<222> LOCATION: (1412)..(1470)
<220> FEATURE:
<221> NAME/KEY: CDS
<222> LOCATION: (1471)..(2701)

<400> SEQUENCE: 3
aattggggaa aggcggtggt cctgaccagg tccccagaga gcgtggccca ccactgctcg      60
gacagggaag cccgaccttg gatcgggcct gacccgtctc ccgtttcctg cacacctct     120 cccatgattc gtggttgcac aaggggccgc agggttgcaa ctgccctgca gagctctcag    180
gttggtcatg tacgtaaggt aaacctgaac cataggatgt tgcggcccgg ctgcgggaag    240
ctcaaaaagc ttccatcgtc gacctgccta aaccgacgac ctaagacggg ctgccttctc    300
tccgatcttg tgtccctccc gtcgattggc ctccctcgtt tcgtcccgcg gcacaatat     360 ataaggcaag gtactgtcca aactggaggg cagatgttcc ttccctcgtc ctgctcccca    420 tgcttccct gccatccact ctcgttcttg tccacctcac tagatgccag tggtgatttc    480
gagaaactga gaaactcaca atg acg ctc cga cac ctc ggg gct gca gca ctc    533
                       Met Thr Leu Arg His Leu Gly Ala Ala Ala Leu
                         1               5                  10 gcc ggt ctc gct tcg gtc gct tct gct ttg tac atc aat ggc tcg gtc     581
Ala Gly Leu Ala Ser Val Ala Ser Ala Leu Tyr Ile Asn Gly Ser Val
            15                  20                  25 acg gcg cca tgc gat tcg ccg ctc tac tgc cag gga gag atc ctg aag     629
Thr Ala Pro Cys Asp Ser Pro Leu Tyr Cys Gln Gly Glu Ile Leu Lys
        30                  35                  40 gca att gag ctg gca cgg ccc ttc tcc gac tcc aag acg ttc gtg gat     677
Ala Ile Glu Leu Ala Arg Pro Phe Ser Asp Ser Lys Thr Phe Val Asp
    45                  50                  55 at  gtaagtcagc gagacccgcc ggcgtgggtg ttggtgagac atgggaatgt          729
Met
 60 tgacctggac ccccgcgctc ag g ccg acg atc aag cca ctg gag gag gtc      779
                          Pro Thr Ile Lys Pro Leu Glu Glu Val
                                                65 att gca gct ttc ggc cgc ttg aag cag ccc ttg agc aac aac tcg gag     827
Ile Ala Ala Phe Gly Arg Leu Lys Gln Pro Leu Ser Asn Asn Ser Glu
 70                  75                  80                  85 ctc acc gcc ttc ctg gct gag aac ttt gcc ccg gcc ggc ggc gag ctg     875
Leu Thr Ala Phe Leu Ala Glu Asn Phe Ala Pro Ala Gly Gly Glu Leu
             90                  95                 100
```

| | | |
|---|---|---|
| gag gag gtg ccc aag agc gag ctg cat acc gac ccc gtc ttc ctc aac<br>Glu Glu Val Pro Lys Ser Glu Leu His Thr Asp Pro Val Phe Leu Asn<br>105 110 115 | | 923 |
| aag ctc gac gat gcc gtg gtc aag gag ttc gtc gga aag gtc atc gac<br>Lys Leu Asp Asp Ala Val Val Lys Glu Phe Val Gly Lys Val Ile Asp<br>120 125 130 | | 971 |
| atc tgg ccc gac ctg acc aga cgc tat gcc ggc ccc ggc aac tgc tcc<br>Ile Trp Pro Asp Leu Thr Arg Arg Tyr Ala Gly Pro Gly Asn Cys Ser<br>135 140 145 | | 1019 |
| aac tgc gag aac agc ttc atc ccc gtg aac cgc acg ttc gtt gtg gcc<br>Asn Cys Glu Asn Ser Phe Ile Pro Val Asn Arg Thr Phe Val Val Ala<br>150 155 160 165 | | 1067 |
| ggc ggc cgc ttc cgc gag ccc tac tac tgg gac tcc tac tgg atc gtc<br>Gly Gly Arg Phe Arg Glu Pro Tyr Tyr Trp Asp Ser Tyr Trp Ile Val<br>170 175 180 | | 1115 |
| gag ggt ctc ctt cgc acc ggc ggc gct ttc gtc ggc atc acc aag aac<br>Glu Gly Leu Leu Arg Thr Gly Gly Ala Phe Val Gly Ile Thr Lys Asn<br>185 190 195 | | 1163 |
| atc ctc gag aac ttc ctg gac ttc atc gag acc att ggc ttc gtg ccc<br>Ile Leu Glu Asn Phe Leu Asp Phe Ile Glu Thr Ile Gly Phe Val Pro<br>200 205 210 | | 1211 |
| aat ggc gcc aga atc tac tac ctc aat cgg tcc cag cca ccg ctc ctc<br>Asn Gly Ala Arg Ile Tyr Tyr Leu Asn Arg Ser Gln Pro Pro Leu Leu<br>215 220 225 | | 1259 |
| aca aag atg atc aag atc tac gtc gac cac acc aag gac acc agc atc<br>Thr Lys Met Ile Lys Ile Tyr Val Asp His Thr Lys Asp Thr Ser Ile<br>230 235 240 245 | | 1307 |
| ctg cag agg gcc ttg cct ctg ctg atc aag gag cac gag tgg tgg acc<br>Leu Gln Arg Ala Leu Pro Leu Leu Ile Lys Glu His Glu Trp Trp Thr<br>250 255 260 | | 1355 |
| aac aac agg agc gtg act gtc act ggc ccc aat ggc aaa acg tac act<br>Asn Asn Arg Ser Val Thr Val Thr Gly Pro Asn Gly Lys Thr Tyr Thr<br>265 270 275 | | 1403 |
| ttg aac ag gtaagtgact cgcactgacg acggcgtggt attatgcagg<br>Leu Asn Arg<br>280 | | 1451 |
| gactgacagt tccccacag g tac cac gtc aac aac aac caa ccc cgg ccc<br>Tyr His Val Asn Asn Asn Gln Pro Arg Pro<br>285 290 | | 1501 |
| gag tca ttc agg gag gac tac atc acc gcc aac aac ggc tcc tac tac<br>Glu Ser Phe Arg Glu Asp Tyr Ile Thr Ala Asn Asn Gly Ser Tyr Tyr<br>295 300 305 | | 1549 |
| gcg acg tcg ggt ata ata tac ccc gtt aag agc ccg ctg aac gag acc<br>Ala Thr Ser Gly Ile Ile Tyr Pro Val Lys Ser Pro Leu Asn Glu Thr<br>310 315 320 | | 1597 |
| gag aaa gat gag acc tac gcc aac ttg gcc acc ggc gct gag tcc ggc<br>Glu Lys Asp Glu Thr Tyr Ala Asn Leu Ala Thr Gly Ala Glu Ser Gly<br>325 330 335 | | 1645 |
| tgg gac tat acc gct aga tgg ctg cgg act cca aat gat gcc gct aag<br>Trp Asp Tyr Thr Ala Arg Trp Leu Arg Thr Pro Asn Asp Ala Ala Lys<br>340 345 350 | | 1693 |
| gac gtc tac ttc ccg ctc cgc tcg ctc aac gtc cgc aac atg atc ccc<br>Asp Val Tyr Phe Pro Leu Arg Ser Leu Asn Val Arg Asn Met Ile Pro<br>355 360 365 370 | | 1741 |
| gtg gac ctc aac tcc atc ctc tac caa aac gag gtc atc att ggc gag<br>Val Asp Leu Asn Ser Ile Leu Tyr Gln Asn Glu Val Ile Ile Gly Glu<br>375 380 385 | | 1789 |
| tac ctc gag cag gca ggc aac aaa tcc gag gcc cag cgc tgg ttc caa<br>Tyr Leu Glu Gln Ala Gly Asn Lys Ser Glu Ala Gln Arg Trp Phe Gln<br>390 395 400 | | 1837 |

```
gcc gcc aac cag cgc agc gag gcc atg tac gcg ctc atg tgg aat gcc    1885
Ala Ala Asn Gln Arg Ser Glu Ala Met Tyr Ala Leu Met Trp Asn Ala
            405                 410                 415 acc cac tgg tcc tac ttc gac tac aac ctg acg agc aat tcc cag tat    1933
Thr His Trp Ser Tyr Phe Asp Tyr Asn Leu Thr Ser Asn Ser Gln Tyr
420                 425                 430 atc ttc atc gcc aac gac gag gac gcc acc acc gcc gag caa gcc aac    1981
Ile Phe Ile Ala Asn Asp Glu Asp Ala Thr Thr Ala Glu Gln Ala Asn
435                 440                 445                 450 tcc ccg cct ggc caa cag gtc ctc ttc tcc atc tcg cag ctc tac ccc    2029
Ser Pro Pro Gly Gln Gln Val Leu Phe Ser Ile Ser Gln Leu Tyr Pro
            455                 460                 465 ttc tgg acc ggc gcc gcc ccc gac cag ctc aag aag aac ccc ctt gcg    2077
Phe Trp Thr Gly Ala Ala Pro Asp Gln Leu Lys Lys Asn Pro Leu Ala
        470                 475                 480 gtc caa caa gcg tac tac cgc atc gag cgc atg ctg aac gag aaa gcc    2125
Val Gln Gln Ala Tyr Tyr Arg Ile Glu Arg Met Leu Asn Glu Lys Ala
            485                 490                 495 ggc gcc atc ccc tcc aca aat ttc agg acc ggc cag caa tgg gac gag    2173
Gly Ala Ile Pro Ser Thr Asn Phe Arg Thr Gly Gln Gln Trp Asp Glu
500                 505                 510 ccc aac gtc tgg cct ccc ctg caa cac atc ctg atg cag ggc ctg ctc    2221
Pro Asn Val Trp Pro Pro Leu Gln His Ile Leu Met Gln Gly Leu Leu
515                 520                 525                 530 aac acc ccg gcc acc ttc ggc acc gcg gac ccg gcc tac gcc gcc gtc    2269
Asn Thr Pro Ala Thr Phe Gly Thr Ala Asp Pro Ala Tyr Ala Ala Val
            535                 540                 545 cag aac ctg gcc ctc cgc ctc gct cag cgc tac ctc gac tcg acc ttc    2317
Gln Asn Leu Ala Leu Arg Leu Ala Gln Arg Tyr Leu Asp Ser Thr Phe
        550                 555                 560 tgc aca tgg tat gcc acg ggc ggc tcg acc agc cag acg ccc cag ctg    2365
Cys Thr Trp Tyr Ala Thr Gly Gly Ser Thr Ser Gln Thr Pro Gln Leu
            565                 570                 575 cag ggc gtc tcc cca ggc gca acg ggg atc atg ttt gag aag tat gcg    2413
Gln Gly Val Ser Pro Gly Ala Thr Gly Ile Met Phe Glu Lys Tyr Ala
        580                 585                 590 gac aac gcg acg aat gtg gct ggc agc ggc ggc gag tac gag gtg gtg    2461
Asp Asn Ala Thr Asn Val Ala Gly Ser Gly Gly Glu Tyr Glu Val Val
595                 600                 605                 610 gag ggg ttt ggg tgg acg aat ggc gtg ctg atc tgg gcg gcc gag acg    2509
Glu Gly Phe Gly Trp Thr Asn Gly Val Leu Ile Trp Ala Ala Glu Thr
            615                 620                 625 ttt ggg aat aag ctg aag agg ccg gat tgc ggt gat atc cag gca gcg    2557
Phe Gly Asn Lys Leu Lys Arg Pro Asp Cys Gly Asp Ile Gln Ala Ala
        630                 635                 640 cat act cat act gat aaa aag aag agg tgg tcg gtg gat ggt gag gtg    2605
His Thr His Thr Asp Lys Lys Lys Arg Trp Ser Val Asp Gly Glu Val
            645                 650                 655 agg gcg agg gag agg atg gcg gtg gag ctc gat ccg tgg gat gcg aag    2653
Arg Ala Arg Glu Arg Met Ala Val Glu Leu Asp Pro Trp Asp Ala Lys
660                 665                 670 tgg acg aag atg ttt ggg cag gca aag ggg agg gta ggg agg agg tcg    2701
Trp Thr Lys Met Phe Gly Gln Ala Lys Gly Arg Val Gly Arg Arg Ser
            675                 680                 685                 690 tgaggagttt gatgattgat ttctttgttc tacaatgagc gtttatgcgt cgtgcggagg    2761
gactcgctga taacgatacc attgccattc gttgcatgaa ccctgcagtt agcggcaagc    2821
tggttgtgtg tgtatcagtg gcagtgttat gataatgcct aatgacaacg tacgagacga    2881
```

```
atcaggtaaa gatttgcatg tgagctgaac tgtgtgggca agatacttag atgagatagc    2941
tgggagctcc ccttccccgg ctagagtgac gcaagctgaa ccgcacatac gacatgacga    3001
tgaacagaat caagccaccc aacacactgc gcccgaaacc ctctttattg cccatcccat    3061
acatatgccc ttcccaaacg ccaaacgcgc aagcaaccaa ccgcagccga gctccatcaa    3121
agtaaaaatg caactagcca ccgatgcccc aagcctatac cggaactgga ccctcctcct    3181
attctctctc ctctttcttt tcc                                            3204

<210> SEQ ID NO 4
<211> LENGTH: 690
<212> TYPE: PRT
<213> ORGANISM: Chaetomium virescens

<400> SEQUENCE: 4

Met Thr Leu Arg His Leu Gly Ala Ala Ala Leu Ala Gly Leu Ala Ser
1               5                   10                  15

Val Ala Ser Ala Leu Tyr Ile Asn Gly Ser Val Thr Ala Pro Cys Asp
            20                  25                  30

Ser Pro Leu Tyr Cys Gln Gly Glu Ile Leu Lys Ala Ile Glu Leu Ala
        35                  40                  45

Arg Pro Phe Ser Asp Ser Lys Thr Phe Val Asp Met Pro Thr Ile Lys
    50                  55                  60

Pro Leu Glu Glu Val Ile Ala Ala Phe Gly Arg Leu Lys Gln Pro Leu
65                  70                  75                  80

Ser Asn Asn Ser Glu Leu Thr Ala Phe Leu Ala Glu Asn Phe Ala Pro
                85                  90                  95

Ala Gly Gly Glu Leu Glu Val Pro Lys Ser Glu Leu His Thr Asp
            100                 105                 110

Pro Val Phe Leu Asn Lys Leu Asp Asp Ala Val Val Lys Glu Phe Val
        115                 120                 125

Gly Lys Val Ile Asp Ile Trp Pro Asp Leu Thr Arg Arg Tyr Ala Gly
    130                 135                 140

Pro Gly Asn Cys Ser Asn Cys Glu Asn Ser Phe Ile Pro Val Asn Arg
145                 150                 155                 160

Thr Phe Val Val Ala Gly Gly Arg Phe Arg Glu Pro Tyr Tyr Trp Asp
                165                 170                 175

Ser Tyr Trp Ile Val Glu Gly Leu Leu Arg Thr Gly Gly Ala Phe Val
            180                 185                 190

Gly Ile Thr Lys Asn Ile Leu Glu Asn Phe Leu Asp Phe Ile Glu Thr
        195                 200                 205

Ile Gly Phe Val Pro Asn Gly Ala Arg Ile Tyr Tyr Leu Asn Arg Ser
    210                 215                 220

Gln Pro Pro Leu Leu Thr Lys Met Ile Lys Ile Tyr Val Asp His Thr
225                 230                 235                 240

Lys Asp Thr Ser Ile Leu Gln Arg Ala Leu Pro Leu Leu Ile Lys Glu
                245                 250                 255

His Glu Trp Trp Thr Asn Asn Arg Ser Val Thr Val Thr Gly Pro Asn
            260                 265                 270

Gly Lys Thr Tyr Thr Leu Asn Arg Tyr His Val Asn Asn Gln Pro
        275                 280                 285

Arg Pro Glu Ser Phe Arg Glu Asp Tyr Ile Thr Ala Asn Asn Gly Ser
    290                 295                 300

Tyr Tyr Ala Thr Ser Gly Ile Ile Tyr Pro Val Lys Ser Pro Leu Asn
305                 310                 315                 320
```

```
Glu Thr Glu Lys Asp Glu Thr Tyr Ala Asn Leu Ala Thr Gly Ala Glu
                325                 330                 335

Ser Gly Trp Asp Tyr Thr Ala Arg Trp Leu Arg Thr Pro Asn Asp Ala
            340                 345                 350

Ala Lys Asp Val Tyr Phe Pro Leu Arg Ser Leu Asn Val Arg Asn Met
        355                 360                 365

Ile Pro Val Asp Leu Asn Ser Ile Leu Tyr Gln Asn Glu Val Ile Ile
370                 375                 380

Gly Glu Tyr Leu Glu Gln Ala Gly Asn Lys Ser Glu Ala Gln Arg Trp
385                 390                 395                 400

Phe Gln Ala Ala Asn Gln Arg Ser Glu Ala Met Tyr Ala Leu Met Trp
                405                 410                 415

Asn Ala Thr His Trp Ser Tyr Phe Asp Tyr Asn Leu Thr Ser Asn Ser
            420                 425                 430

Gln Tyr Ile Phe Ile Ala Asn Asp Glu Asp Ala Thr Thr Ala Glu Gln
        435                 440                 445

Ala Asn Ser Pro Pro Gly Gln Gln Val Leu Phe Ser Ile Ser Gln Leu
450                 455                 460

Tyr Pro Phe Trp Thr Gly Ala Pro Asp Gln Leu Lys Lys Asn Pro
465                 470                 475                 480

Leu Ala Val Gln Gln Ala Tyr Tyr Arg Ile Glu Arg Met Leu Asn Glu
                485                 490                 495

Lys Ala Gly Ala Ile Pro Ser Thr Asn Phe Arg Thr Gly Gln Gln Trp
            500                 505                 510

Asp Glu Pro Asn Val Trp Pro Leu Gln His Ile Leu Met Gln Gly
        515                 520                 525

Leu Leu Asn Thr Pro Ala Thr Phe Gly Thr Ala Asp Pro Ala Tyr Ala
530                 535                 540

Ala Val Gln Asn Leu Ala Leu Arg Leu Ala Gln Arg Tyr Leu Asp Ser
545                 550                 555                 560

Thr Phe Cys Thr Trp Tyr Ala Thr Gly Gly Ser Thr Ser Gln Thr Pro
                565                 570                 575

Gln Leu Gln Gly Val Ser Pro Gly Ala Thr Gly Ile Met Phe Glu Lys
            580                 585                 590

Tyr Ala Asp Asn Ala Thr Asn Val Ala Gly Ser Gly Gly Glu Tyr Glu
        595                 600                 605

Val Val Glu Gly Phe Gly Trp Thr Asn Gly Val Leu Ile Trp Ala Ala
610                 615                 620

Glu Thr Phe Gly Asn Lys Leu Lys Arg Pro Asp Cys Gly Asp Ile Gln
625                 630                 635                 640

Ala Ala His Thr His Thr Asp Lys Lys Lys Arg Trp Ser Val Asp Gly
                645                 650                 655

Glu Val Arg Ala Arg Glu Arg Met Ala Val Glu Leu Asp Pro Trp Asp
            660                 665                 670

Ala Lys Trp Thr Lys Met Phe Gly Gln Ala Lys Gly Arg Val Gly Arg
        675                 680                 685

Arg Ser
    690

<210> SEQ ID NO 5
<211> LENGTH: 1599
<212> TYPE: DNA
<213> ORGANISM: Aspergillus fumigatus
```

<400> SEQUENCE: 5

```
atgctggcct ccaccttctc ctaccgcatg tacaagaccg cgctcatcct ggccgccctt      60
ctgggctctg gccaggctca gcaggtcggt acttcccagg cggaagtgca tccgtccatg     120
acctggcaga gctgcacggc tggcggcagc tgcaccacca caacggcaa ggtggtcatc     180
gacgcgaact ggcgttgggt gcacaaagtc ggcgactaca ccaactgcta caccggcaac     240
acctgggaca cgactatctg ccctgacgat gcgacctgcg catccaactg cgcccttgag     300
ggtgccaact acgaatccac ctatggtgtg accgccagcg gcaattccct ccgcctcaac     360
ttcgtcacca ccagccagca gaagaacatt ggctcgcgtc tgtacatgat gaaggacgac     420
tcgacctacg agatgtttaa gctgctgaac caggagttca ccttcgatgt cgatgtctcc     480
aacctcccct gcggtctcaa cggtgctctg tactttgtcg ccatggacgc cgacggtggc     540
atgtccaagt acccaaccaa caaggccggt gccaagtacg gtactggata ctgtgactcg     600
cagtgccctc gcgacctcaa gttcatcaac ggtcaggcca acgtcgaagg gtggcagccc     660
tcctccaacg atgccaatgc gggtaccggc aaccacgggt cctgctgcgc ggagatggat     720
atctgggagg ccaacagcat ctccacggcc ttcaccccc atccgtgcga cacgcccggc     780
caggtgatgt gcaccggtga tgcctgcggt ggcacctaca gctccgaccg ctacggcggc     840
acctgcgacc ccgacggatg tgatttcaac tccttccgcc agggcaacaa gaccttctac     900
ggccctggca tgaccgtcga caccaagagc aagtttaccg tcgtcaccca gttcatcacc     960
gacgacggca cctccagcgg caccctcaag gagatcaagc gcttctacgt gcagaacggc    1020
aaggtgatcc ccaactcgga gtcgacctgg accggcgtca gcggcaactc catcaccacc    1080
gagtactgca ccgcccagaa gagcctgttc caggaccaga acgtcttcga aaagcacggc    1140
ggcctcgagg gcatgggtgc tgccctcgcc cagggtatgg ttctcgtcat gtccctgtgg    1200
gatgatcact cggccaacat gctctggctc gacagcaact acccgaccac tgcctcttcc    1260
accactcccg gcgtcgcccg tggtacctgc gacatctcct ccggcgtccc tgcggatgtc    1320
gaggcgaacc accccgacgc ctacgtcgtc tactccaaca tcaaggtcgg ccccatcggc    1380
tcgaccttca cagcggtgg ctcgaacccc ggtggcggaa ccaccacgac aactaccacc    1440
cagcctacta ccaccacgac cacggctgga aaccctggcg gcaccggagt cgcacagcac    1500
tatggccagt gtggtggaat cggatggacc ggacccacaa cctgtgccag cccttatacc    1560
tgccagaagc tgaatgatta ttactctcag tgcctgtag                           1599
```

<210> SEQ ID NO 6
<211> LENGTH: 532
<212> TYPE: PRT
<213> ORGANISM: Aspergillus fumigatus

<400> SEQUENCE: 6

```
Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
65                  70                  75                  80
```

```
Thr Trp Asp Thr Thr Ile Cys Pro Asp Asp Ala Thr Cys Ala Ser Asn
                    85                  90                  95
Cys Ala Leu Glu Gly Ala Asn Tyr Glu Ser Thr Tyr Gly Val Thr Ala
            100                 105                 110
Ser Gly Asn Ser Leu Arg Leu Asn Phe Val Thr Thr Ser Gln Gln Lys
        115                 120                 125
Asn Ile Gly Ser Arg Leu Tyr Met Met Lys Asp Asp Ser Thr Tyr Glu
    130                 135                 140
Met Phe Lys Leu Leu Asn Gln Glu Phe Thr Phe Asp Val Asp Val Ser
145                 150                 155                 160
Asn Leu Pro Cys Gly Leu Asn Gly Ala Leu Tyr Phe Val Ala Met Asp
                165                 170                 175
Ala Asp Gly Gly Met Ser Lys Tyr Pro Thr Asn Lys Ala Gly Ala Lys
            180                 185                 190
Tyr Gly Thr Gly Tyr Cys Asp Ser Gln Cys Pro Arg Asp Leu Lys Phe
        195                 200                 205
Ile Asn Gly Gln Ala Asn Val Glu Gly Trp Gln Pro Ser Ser Asn Asp
    210                 215                 220
Ala Asn Ala Gly Thr Gly Asn His Gly Ser Cys Cys Ala Glu Met Asp
225                 230                 235                 240
Ile Trp Glu Ala Asn Ser Ile Ser Thr Ala Phe Thr Pro His Pro Cys
                245                 250                 255
Asp Thr Pro Gly Gln Val Met Cys Thr Gly Asp Ala Cys Gly Gly Thr
            260                 265                 270
Tyr Ser Ser Asp Arg Tyr Gly Gly Thr Cys Asp Pro Asp Gly Cys Asp
        275                 280                 285
Phe Asn Ser Phe Arg Gln Gly Asn Lys Thr Phe Tyr Gly Pro Gly Met
    290                 295                 300
Thr Val Asp Thr Lys Ser Lys Phe Thr Val Val Thr Gln Phe Ile Thr
305                 310                 315                 320
Asp Asp Gly Thr Ser Ser Gly Thr Leu Lys Glu Ile Lys Arg Phe Tyr
                325                 330                 335
Val Gln Asn Gly Lys Val Ile Pro Asn Ser Glu Ser Thr Trp Thr Gly
            340                 345                 350
Val Ser Gly Asn Ser Ile Thr Thr Glu Tyr Cys Thr Ala Gln Lys Ser
        355                 360                 365
Leu Phe Gln Asp Gln Asn Val Phe Glu Lys His Gly Gly Leu Glu Gly
    370                 375                 380
Met Gly Ala Ala Leu Ala Gln Gly Met Val Leu Val Met Ser Leu Trp
385                 390                 395                 400
Asp Asp His Ser Ala Asn Met Leu Trp Leu Asp Ser Asn Tyr Pro Thr
                405                 410                 415
Thr Ala Ser Ser Thr Thr Pro Gly Val Ala Arg Gly Thr Cys Asp Ile
            420                 425                 430
Ser Ser Gly Val Pro Ala Asp Val Glu Ala Asn His Pro Asp Ala Tyr
        435                 440                 445
Val Val Tyr Ser Asn Ile Lys Val Gly Pro Ile Gly Ser Thr Phe Asn
    450                 455                 460
Ser Gly Gly Ser Asn Pro Gly Gly Thr Thr Thr Thr Thr Thr Thr Thr
465                 470                 475                 480
Gln Pro Thr Thr Thr Thr Thr Ala Gly Asn Pro Gly Gly Thr Gly
                485                 490                 495
Val Ala Gln His Tyr Gly Gln Cys Gly Gly Ile Gly Trp Thr Gly Pro
```

```
            500             505             510
Thr Thr Cys Ala Ser Pro Tyr Thr Cys Gln Lys Leu Asn Asp Tyr Tyr
        515             520                 525

Ser Gln Cys Leu
    530

<210> SEQ ID NO 7
<211> LENGTH: 1713
<212> TYPE: DNA
<213> ORGANISM: Aspergillus fumigatus

<400> SEQUENCE: 7
atgaagcacc ttgcatcttc catcgcattg actctactgt tgcctgccgt gcaggcccag    60
cagaccgtat ggggccaatg tatgttctgg ctgtcactgg aataagactg tatcaactgc   120
tgatatgctt ctaggtggcg ccaaggctg tctggcccg acgagctgtg ttgccggcgc    180
agcctgtagc acactgaatc cctgtatgtt agatatcgtc ctgagtggag acttatactg   240
acttccttag actacgctca gtgtatcccg ggagccaccg cgacgtccac caccctcacg   300
acgacgacgg cggcgacgac gacatcccag accaccacca aacctaccac gactggtcca   360
actacatccg cacccaccgt gaccgcatcc ggtaacccct tcagcggcta ccagctgtat   420
gccaacccct actactcctc cgaggtccat actctggcca tgccttctct gcccagctcg   480
ctgcagccca aggctagtgc tgttgctgaa gtgccctcat tgtttggct gtaagtggcc    540 ttatcccaat actgagacca actctctgac agtcgtagcg acgttgccgc caaggtgccc   600
actatgggaa cctacctggc cgacattcag gccaagaaca aggccggcgc caaccctcct   660
atcgctggta tcttcgtggt ctacgacttg ccggaccgtg actgcgccgc tctggccagt   720
aatggcgagt actcaattgc caacaacggt gtggccaact acaaggcgta cattgacgcc   780
atccgtgctc agctggtgaa gtactctgac gttcacacca tcctcgtcat cggtaggccg   840
tacacctccg ttgcgcgccg cctttctctg acatcttgca gaacccgaca gcttggccaa   900
cctggtgacc aacctcaacg tcgccaaatg cgccaatgcg cagagcgcct acctggagtg   960
tgtcgactat gctctgaagc agctcaacct gcccaacgtc gccatgtacc tcgacgcagg  1020
tatgcctcac ttcccgcatt ctgtatccct tccagacact aactcatcag gccatgcggg  1080
ctggctcgga tggcccgcca acttgggccc gccgcaaca ctcttcgcca aagtctacac   1140
cgacgcgggt tcccccgcgg ctgttcgtgg cctggccacc aacgtcgcca actacaacgc  1200
ctggtcgctc agtaccctgcc cctcctacac ccagggagac cccaactgcg acgagaagaa  1260
gtacatcaac gccatggcgc ctcttctcaa ggaagccggc ttcgatgccc acttcatcat  1320
ggatacctgt aagtgcttat tccaatcgcc gatgtgtgcc gactaatcaa tgtttcagcc  1380
cggaatggcg tccagcccac gaagcaaaac gcctggggtg actggtgcaa cgtcatcggc   1440
accggcttcg gtgttcgccc ctcgactaac accggcgatc cgctccagga tgcctttgtg  1500
tggatcaagc ccgtggagga gagtgatggc acgtccaact cgacttcccc ccggtatgac  1560
gcgcactgcg gatatagtga tgctctgcag cctgctcctg aggctggtac ttggttccag  1620
gtatgtcatc cattagccag atgagggata agtgactgac ggacctaggc ctactttgag  1680
cagcttctga ccaacgctaa cccgtccttt taa                              1713

<210> SEQ ID NO 8
<211> LENGTH: 454
<212> TYPE: PRT
<213> ORGANISM: Aspergillus fumigatus
```

<400> SEQUENCE: 8

```
Met Lys His Leu Ala Ser Ser Ile Ala Leu Thr Leu Leu Pro Ala
1               5                   10                  15

Val Gln Ala Gln Gln Thr Val Trp Gly Gln Cys Gly Gly Gln Gly Trp
            20                  25                  30

Ser Gly Pro Thr Ser Cys Val Ala Gly Ala Ala Cys Ser Thr Leu Asn
            35                  40                  45

Pro Tyr Tyr Ala Gln Cys Ile Pro Gly Ala Thr Ala Thr Ser Thr Thr
        50                  55                  60

Leu Thr Thr Thr Thr Ala Ala Thr Thr Thr Ser Gln Thr Thr Thr Lys
65                  70                  75                  80

Pro Thr Thr Thr Gly Pro Thr Thr Ser Ala Pro Thr Val Thr Ala Ser
                85                  90                  95

Gly Asn Pro Phe Ser Gly Tyr Gln Leu Tyr Ala Asn Pro Tyr Tyr Ser
                100                 105                 110

Ser Glu Val His Thr Leu Ala Met Pro Ser Leu Pro Ser Ser Leu Gln
            115                 120                 125

Pro Lys Ala Ser Ala Val Ala Glu Val Pro Ser Phe Val Trp Leu Asp
        130                 135                 140

Val Ala Ala Lys Val Pro Thr Met Gly Thr Tyr Leu Ala Asp Ile Gln
145                 150                 155                 160

Ala Lys Asn Lys Ala Gly Ala Asn Pro Pro Ile Ala Gly Ile Phe Val
                165                 170                 175

Val Tyr Asp Leu Pro Asp Arg Asp Cys Ala Ala Leu Ala Ser Asn Gly
                180                 185                 190

Glu Tyr Ser Ile Ala Asn Asn Gly Val Ala Asn Tyr Lys Ala Tyr Ile
            195                 200                 205

Asp Ala Ile Arg Ala Gln Leu Val Lys Tyr Ser Asp Val His Thr Ile
        210                 215                 220

Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
                245                 250                 255

Tyr Ala Leu Lys Gln Leu Asn Leu Pro Asn Val Ala Met Tyr Leu Asp
                260                 265                 270

Ala Gly His Ala Gly Trp Leu Gly Trp Pro Ala Asn Leu Gly Pro Ala
            275                 280                 285

Ala Thr Leu Phe Ala Lys Val Tyr Thr Asp Ala Gly Ser Pro Ala Ala
        290                 295                 300

Val Arg Gly Leu Ala Thr Asn Val Ala Asn Tyr Asn Ala Trp Ser Leu
305                 310                 315                 320

Ser Thr Cys Pro Ser Tyr Thr Gln Gly Asp Pro Asn Cys Asp Glu Lys
                325                 330                 335

Lys Tyr Ile Asn Ala Met Ala Pro Leu Leu Lys Glu Ala Gly Phe Asp
                340                 345                 350

Ala His Phe Ile Met Asp Thr Ser Arg Asn Gly Val Gln Pro Thr Lys
            355                 360                 365

Gln Asn Ala Trp Gly Asp Trp Cys Asn Val Ile Gly Thr Gly Phe Gly
        370                 375                 380

Val Arg Pro Ser Thr Asn Thr Gly Asp Pro Leu Gln Asp Ala Phe Val
385                 390                 395                 400

Trp Ile Lys Pro Gly Gly Glu Ser Asp Gly Thr Ser Asn Ser Thr Ser
```

405                 410                 415
Pro Arg Tyr Asp Ala His Cys Gly Tyr Ser Asp Ala Leu Gln Pro Ala
            420                 425                 430

Pro Glu Ala Gly Thr Trp Phe Gln Ala Tyr Phe Glu Gln Leu Leu Thr
        435                 440                 445

Asn Ala Asn Pro Ser Phe
    450

<210> SEQ ID NO 9
<211> LENGTH: 3060
<212> TYPE: DNA
<213> ORGANISM: Aspergillus fumigatus

<400> SEQUENCE: 9

| | | | | | |
|---|---|---|---|---|---|
| atgagattcg | gttggctcga | ggtggccgct | ctgacggccg | cttctgtagc | caatgcccag | 60 |
| gtttgtgatg | cttccccgtc | attgtttcgg | atatagttga | caatagtcat | ggaaataatc | 120 |
| aggaattggc | tttctctcca | ccattctacc | cttcgccttg | ggctgatggc | cagggagagt | 180 |
| gggcagatgc | ccatcgacgc | gccgtcgaga | tcgtttctca | gatgacactg | gcggagaagg | 240 |
| ttaaccttac | aacgggtact | gggtgggttg | cgactttttt | gttgacagtg | agctttcttc | 300 |
| actgaccatc | tacacagatg | ggaaatggac | cgatgcgtcg | gtcaaaccgg | cagcgttccc | 360 |
| aggtaagctt | gcaattctgc | aacaacgtgc | aagtgtagtt | gctaaaacgc | ggtggtgcag | 420 |
| acttggtatc | aactggggtc | tttgtggcca | ggattcccct | tgggtatcc | gtttctgtga | 480 |
| gctatacccg | cggagtcttt | cagtccttgt | attatgtgct | gatgattgtc | tctgtatagc | 540 |
| tgacctcaac | tccgccttcc | ctgctggtac | taatgtcgcc | gcgacatggg | acaagacact | 600 |
| cgcctacctt | cgtggcaagg | ccatgggtga | ggaattcaac | gacaagggcg | tggacatttt | 660 |
| gctggggcct | gctgctggtc | ctctcggcaa | atacccggac | ggcggcagaa | tctgggaagg | 720 |
| cttctctcct | gatccggttc | tcactggtgt | acttttcgcc | gaaactatca | agggtatcca | 780 |
| agacgcgggt | gtgattgcta | ctgccaagca | ttacattctg | aatgaacagg | agcatttccg | 840 |
| acaggttggc | gaggcccagg | atatggttta | caacatcacg | gagacgatca | gctccaacgt | 900 |
| ggatgacaag | accatgcacg | agttgtacct | tggtgagta | gttgacactg | caaatgagga | 960 |
| ccttgattga | tttgactgac | ctggaatgca | ggcccttgc | agatgctgtg | cgcggtaaga | 1020 |
| ttttccgtag | acttgacctc | gcgacgaaga | atcgctgac | gaaccatcgt | agctggcgtt | 1080 |
| ggcgctgtca | tgtgttccta | caatcaaatc | aacaacagct | acggttgtca | aaacagtcaa | 1140 |
| actctcaaca | agctcctcaa | ggctgagctg | ggcttccaag | gcttcgtcat | gagtgactgg | 1200 |
| agcgctcacc | acagcggtgt | cggcgctgcc | ctcgctgggt | tggatatgtc | gatgcctgga | 1260 |
| gacatttcct | tcgacgacgg | actctccttc | tggggcacga | acctaactgt | cagtgttctt | 1320 |
| aacggcaccg | ttccagcctg | gcgtgtcgat | gacatggctg | ttcgtatcat | gaccgcgtac | 1380 |
| tacaaggttg | gtcgtgaccg | tcttcgtatt | cccctaact | tcagctcctg | gacccgggat | 1440 |
| gagtacggct | gggagcattc | tgctgtctcc | gagggagcct | ggaccaaggt | gaacgacttc | 1500 |
| gtcaatgtgc | agcgcagtca | ctctcagatc | atccgtgaga | ttggtgccgc | tagtacagtg | 1560 |
| ctcttgaaga | acacgggtgc | tcttcctttg | accggcaagg | aggttaaagt | gggtgttctc | 1620 |
| ggtgaagacg | ctggttccaa | cccgtgggt | gctaacggct | gccccgaccg | cggctgtgat | 1680 |
| aacggcactc | ttgctatggc | ctgggtagt | ggtactgcca | acttccctta | ccttgtcacc | 1740 |
| cccgagcagg | ctatccagcg | agaggtcatc | agcaacggcg | gcaatgtctt | tgctgtgact | 1800 |

```
gataacgggg ctctcagcca gatggcagat gttgcatctc aatccaggtg agtgcgggct    1860
cttagaaaaa gaacgttctc tgaatgaagt ttttaaccaa ttgcgaacag cgtgtctttg    1920
gtgtttgtca acgccgactc tggagagggt ttcatcagtg tcgacggcaa cgagggtgac    1980
cgcaaaaatc tcactctgtg gaagaacggc gaggccgtca ttgacactgt tgtcagccac    2040
tgcaacaaca cgattgtggt tattcacagt gttgggcccg tcttgatcga ccggtggtat    2100
gataacccca acgtcactgc catcatctgg gccggcttgc ccggtcagga gagtggcaac    2160
tccctggtcg acgtgctcta tggccgcgtc aaccccagcg ccaagacccc gttcacctgg    2220
ggcaagactc gggagtctta cggggctccc ttgctcaccg agcctaacaa tggcaatggt    2280
gctccccagg atgatttcaa cgagggcgtc ttcattgact accgtcactt tgacaagcgc    2340
aatgagaccc ccatttatga gtttggccat ggcttgagct acaccaccct tggttactct    2400
caccttcggg ttcaggccct caatagttcg agttcggcat atgtcccgac tagcggagag    2460
accaagcctg cgccaaccta tggtgagatc ggtagtgccg ccgactacct gtatcccgag    2520
ggtctcaaaa gaattaccaa gtttatttac ccttggctca actcgaccga cctcgaggat    2580
tcttctgacg acccgaacta cggctgggag gactcggagt acattcccga aggcgctagg    2640
gatgggtctc ctcaaccccT cctgaaggct ggcggcgctc tggtggtaa ccctaccctt    2700 tatcaggatc ttgttagggt gtcggccacc ataaccaaca ctggtaacgt cgccggttat    2760
gaagtccctc aattggtgag tgacccgcat gttccttgcg ttgcaatttg gctaactcgc    2820
ttctagtatg tttcactggg cggaccgaac gagcctcggg tcgttctgcg caagttcgac    2880
cgaatcttcc tggctcctgg ggagcaaaag gtttggacca cgactcttaa ccgtcgtgat    2940
ctcgccaatt gggatgtgga ggctcaggac tgggtcatca caaagtaccc caagaaagtg    3000
cacgtcggca gctcctcgcg taagctgcct ctgagagcgc tctgccccg tgtctactag    3060
```

<210> SEQ ID NO 10
<211> LENGTH: 863
<212> TYPE: PRT
<213> ORGANISM: Aspergillus fumigatus

<400> SEQUENCE: 10

Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
    130                 135                 140

Ala Ala Gly Pro Leu Gly Lys Tyr Pro Asp Gly Gly Arg Ile Trp Glu
145                 150                 155                 160

```
Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Leu Asn Glu Gln Glu His Phe Arg Gln Val Gly Glu Ala Gln Gly
        195                 200                 205

Tyr Gly Tyr Asn Ile Thr Glu Thr Ile Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
            260                 265                 270

Gly Phe Gln Gly Phe Val Met Ser Asp Trp Ser Ala His His Ser Gly
        275                 280                 285

Val Gly Ala Ala Leu Ala Gly Leu Asp Met Ser Met Pro Gly Asp Ile
    290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
            340                 345                 350

Pro Pro Asn Phe Ser Ser Trp Thr Arg Asp Glu Tyr Gly Trp Glu His
        355                 360                 365

Ser Ala Val Ser Glu Gly Ala Trp Thr Lys Val Asn Asp Phe Val Asn
    370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
            420                 425                 430

Ala Asn Gly Cys Pro Asp Arg Gly Cys Asp Asn Gly Thr Leu Ala Met
        435                 440                 445

Ala Trp Gly Ser Gly Thr Ala Asn Phe Pro Tyr Leu Val Thr Pro Glu
    450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
                485                 490                 495

Ser Ser Val Ser Leu Val Phe Val Asn Ala Asp Ser Gly Glu Gly Phe
            500                 505                 510

Ile Ser Val Asp Gly Asn Glu Gly Asp Arg Lys Asn Leu Thr Leu Trp
        515                 520                 525

Lys Asn Gly Glu Ala Val Ile Asp Thr Val Val Ser His Cys Asn Asn
    530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575
```

| | | | | | | | | | | | |
|---|---|---|---|---|---|---|---|---|---|---|---|
|Gln|Glu|Ser|Gly|Asn|Ser|Leu|Val|Asp|Val|Leu|Tyr|Gly|Arg|Val|Asn|
| | | |580| | | |585| | | |590| | | | |

Gln Glu Ser Gly Asn Ser Leu Val Asp Val Leu Tyr Gly Arg Val Asn
                580                 585                 590

Pro Ser Ala Lys Thr Pro Phe Thr Trp Gly Lys Thr Arg Glu Ser Tyr
        595                 600                 605

Gly Ala Pro Leu Leu Thr Glu Pro Asn Asn Gly Asn Gly Ala Pro Gln
    610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
        675                 680                 685

Gly Glu Ile Gly Ser Ala Ala Asp Tyr Leu Tyr Pro Glu Gly Leu Lys
    690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
            740                 745                 750

Gly Ala Pro Gly Gly Asn Pro Thr Leu Tyr Gln Asp Leu Val Arg Val
        755                 760                 765

Ser Ala Thr Ile Thr Asn Thr Gly Asn Val Ala Gly Tyr Glu Val Pro
    770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
        835                 840                 845

Ser Ser Arg Lys Leu Pro Leu Arg Ala Pro Leu Pro Arg Val Tyr
    850                 855                 860

<210> SEQ ID NO 11
<211> LENGTH: 835
<212> TYPE: DNA
<213> ORGANISM: Penicillium sp.

<400> SEQUENCE: 11

```
atgctgtctt cgacgactcg caccctcgcc tttacaggcc ttgcgggcct tctgtccgct        60
cccctggtca aggcccatgg ctttgtccag ggcattgtca tcggtgacca attgtaagtc       120
cctctcttgc agttctgtcg attaactgct ggactgcttg cttgactccc tgctgactcc       180
caacagctac agcgggtaca tcgtcaactc gttcccctac gaatccaacc caccccccgt       240
catcggctgg gccacgaccg ccaccgacct gggcttcgtc gacggcacag gataccaagg       300
cccggacatc atctgccacc ggaatgcgac gcccgcgccg ctgacagccc ccgtggccgc       360
cggcggcacc gtcgagctgc agtggacgcc gtggccggac agccaccacg gacccgtcat       420
cacctacctg gcgccgtgca acggcaactg ctcgaccgtc gacaagacga cgctggagtt       480
cttcaagatc gaccagcagg gcctgatcga cgacacgagc ccgccgggca cctgggcgtc       540
```

-continued

```
ggacaacctc atcgccaaca acaatagctg daccgtcacc attcccaaca gcgtcgcccc      600
cggcaactac gtcctgcgcc acgagatcat cgccctgcac tcggccaaca acaaggacgg      660
cgcccagaac taccccagt gcatcaacat cgaggtcacg gcggcggct ccgacgcgcc        720 tgagggtact ctgggcgagg atctctacca tgacaccgac ccgggcattc tggtcgacat      780
ttacgagccc attgcgacgt ataccattcc ggggccgcct gagccgacgt tctag           835
```

```
<210> SEQ ID NO 12
<211> LENGTH: 253
<212> TYPE: PRT
<213> ORGANISM: Penicillium sp.
<220> FEATURE:
<221> NAME/KEY: SIGNAL
<222> LOCATION: (1)..(25)
<220> FEATURE:
<221> NAME/KEY: SIGNAL
<222> LOCATION: (26)..(253)

<400> SEQUENCE: 12
```

Met Leu Ser Ser Thr Thr Arg Thr Leu Ala Phe Thr Gly Leu Ala Gly
1               5                   10                  15

Leu Leu Ser Ala Pro Leu Val Lys Ala His Gly Phe Val Gln Gly Ile
            20                  25                  30

Val Ile Gly Asp Gln Phe Tyr Ser Gly Tyr Ile Val Asn Ser Phe Pro
        35                  40                  45

Tyr Glu Ser Asn Pro Pro Val Ile Gly Trp Ala Thr Thr Ala Thr
    50                  55                  60

Asp Leu Gly Phe Val Asp Gly Thr Gly Tyr Gln Gly Pro Asp Ile Ile
65                  70                  75                  80

Cys His Arg Asn Ala Thr Pro Ala Pro Leu Thr Ala Pro Val Ala Ala
                85                  90                  95

Gly Gly Thr Val Glu Leu Gln Trp Thr Pro Trp Pro Asp Ser His His
            100                 105                 110

Gly Pro Val Ile Thr Tyr Leu Ala Pro Cys Asn Gly Asn Cys Ser Thr
        115                 120                 125

Val Asp Lys Thr Thr Leu Glu Phe Phe Lys Ile Asp Gln Gln Gly Leu
    130                 135                 140

Ile Asp Asp Thr Ser Pro Pro Gly Thr Trp Ala Ser Asp Asn Leu Ile
145                 150                 155                 160

Ala Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
        195                 200                 205

Thr Gly Gly Gly Ser Asp Ala Pro Glu Gly Thr Leu Gly Glu Asp Leu
    210                 215                 220

Tyr His Asp Thr Asp Pro Gly Ile Leu Val Asp Ile Tyr Glu Pro Ile
225                 230                 235                 240

Ala Thr Tyr Thr Ile Pro Gly Pro Pro Glu Pro Thr Phe
                245                 250

```
<210> SEQ ID NO 13
<211> LENGTH: 618
<212> TYPE: PRT
<213> ORGANISM: Talaromyces emersonii
<220> FEATURE:
```

```
<221> NAME/KEY: SIGNAL
<222> LOCATION: (1)..(20)
<220> FEATURE:
<221> NAME/KEY: mat_peptide
<222> LOCATION: (21)..(618)

<400> SEQUENCE: 13

Met Ala Ser Leu Val Ala Gly Ala Leu Cys Ile Leu Gly Leu Thr Pro
-20                 -15                 -10                  -5

Ala Ala Phe Ala Arg Ala Pro Val Ala Arg Ala Thr Gly Ser Leu
         -1  1              5                   10

Asp Ser Phe Leu Ala Thr Glu Thr Pro Ile Ala Leu Gln Gly Val Leu
             15                  20                  25

Asn Asn Ile Gly Pro Asn Gly Ala Asp Val Ala Gly Ala Ser Ala Gly
 30                  35                  40

Ile Val Val Ala Ser Pro Ser Arg Ser Asp Pro Asn Tyr Phe Tyr Ser
 45                  50                  55                  60

Trp Thr Arg Asp Ala Ala Leu Thr Ala Lys Tyr Leu Val Asp Ala Phe
                 65                  70                  75

Ile Ala Gly Asn Lys Asp Leu Glu Gln Thr Ile Gln Gln Tyr Ile Ser
             80                  85                  90

Ala Gln Ala Lys Val Gln Thr Ile Ser Asn Pro Ser Gly Asp Leu Ser
         95                 100                 105

Thr Gly Gly Leu Gly Glu Pro Lys Phe Asn Val Asn Glu Thr Ala Phe
110                 115                 120

Thr Gly Pro Trp Gly Arg Pro Gln Arg Asp Gly Pro Ala Leu Arg Ala
125                 130                 135                 140

Thr Ala Leu Ile Ala Tyr Ala Asn Tyr Leu Ile Asp Asn Gly Glu Ala
                145                 150                 155

Ser Thr Ala Asp Glu Ile Ile Trp Pro Ile Val Gln Asn Asp Leu Ser
                160                 165                 170

Tyr Ile Thr Gln Tyr Trp Asn Ser Thr Phe Asp Leu Trp Glu Glu
            175                 180                 185

Val Glu Gly Ser Ser Phe Phe Thr Thr Ala Val Gln His Arg Ala Leu
190                 195                 200

Val Glu Gly Asn Ala Leu Ala Thr Arg Leu Asn His Thr Cys Ser Asn
205                 210                 215                 220

Cys Val Ser Gln Ala Pro Gln Val Leu Cys Phe Leu Gln Ser Tyr Trp
                225                 230                 235

Thr Gly Ser Tyr Val Leu Ala Asn Phe Gly Gly Ser Gly Arg Ser Gly
                240                 245                 250

Lys Asp Val Asn Ser Ile Leu Gly Ser Ile His Thr Phe Asp Pro Ala
                255                 260                 265

Gly Gly Cys Asp Asp Ser Thr Phe Gln Pro Cys Ser Ala Arg Ala Leu
270                 275                 280

Ala Asn His Lys Val Val Thr Asp Ser Phe Arg Ser Ile Tyr Ala Ile
285                 290                 295                 300

Asn Ser Gly Ile Ala Glu Gly Ser Ala Val Ala Val Gly Arg Tyr Pro
                305                 310                 315

Glu Asp Val Tyr Gln Gly Gly Asn Pro Trp Tyr Leu Ala Thr Ala Ala
                320                 325                 330

Ala Ala Glu Gln Leu Tyr Asp Ala Ile Tyr Gln Trp Lys Lys Ile Gly
            335                 340                 345

Ser Ile Ser Ile Thr Asp Val Ser Leu Pro Phe Phe Gln Asp Ile Tyr
            350                 355                 360
```

```
Pro Ser Ala Ala Val Gly Thr Tyr Asn Ser Gly Ser Thr Thr Phe Asn
365                 370                 375                 380

Asp Ile Ile Ser Ala Val Gln Thr Tyr Gly Asp Gly Tyr Leu Ser Ile
            385                 390                 395

Val Glu Lys Tyr Thr Pro Ser Asp Gly Ser Leu Thr Glu Gln Phe Ser
        400                 405                 410

Arg Thr Asp Gly Thr Pro Leu Ser Ala Ser Ala Leu Thr Trp Ser Tyr
        415                 420                 425

Ala Ser Leu Leu Thr Ala Ser Ala Arg Arg Gln Ser Val Val Pro Ala
        430                 435                 440

Ser Trp Gly Glu Ser Ser Ala Ser Ser Val Pro Ala Val Cys Ser Ala
445                 450                 455                 460

Thr Ser Ala Thr Gly Pro Tyr Ser Thr Ala Thr Asn Thr Val Trp Pro
                465                 470                 475

Ser Ser Gly Ser Gly Ser Ser Thr Thr Ser Ser Ala Pro Cys Thr
                480                 485                 490

Thr Pro Thr Ser Val Ala Val Thr Phe Asp Glu Ile Val Ser Thr Ser
        495                 500                 505

Tyr Gly Glu Thr Ile Tyr Leu Ala Gly Ser Ile Pro Glu Leu Gly Asn
        510                 515                 520

Trp Ser Thr Ala Ser Ala Ile Pro Leu Arg Ala Asp Ala Tyr Thr Asn
525                 530                 535                 540

Ser Asn Pro Leu Trp Tyr Val Thr Val Asn Leu Pro Pro Gly Thr Ser
                545                 550                 555

Phe Glu Tyr Lys Phe Lys Asn Gln Thr Asp Gly Thr Ile Val Trp
                560                 565                 570

Glu Asp Asp Pro Asn Arg Ser Tyr Thr Val Pro Ala Tyr Cys Gly Gln
                575                 580                 585

Thr Thr Ala Ile Leu Asp Asp Ser Trp Gln
    590                 595

<210> SEQ ID NO 14
<211> LENGTH: 574
<212> TYPE: PRT
<213> ORGANISM: Trametes cingulata
<220> FEATURE:
<221> NAME/KEY: SIGNAL
<222> LOCATION: (1)..(18)
<220> FEATURE:
<221> NAME/KEY: mat_peptide
<222> LOCATION: (19)..(574)

<400> SEQUENCE: 14

Met Arg Phe Thr Leu Leu Thr Ser Leu Leu Gly Leu Ala Leu Gly Ala
                -15                 -10                 -5

Phe Ala Gln Ser Ser Ala Ala Asp Ala Tyr Val Ala Ser Glu Ser Pro
 -1   1             5                  10

Ile Ala Lys Ala Gly Val Leu Ala Asn Ile Gly Pro Ser Gly Ser Lys
 15              20                  25                  30

Ser Asn Gly Ala Lys Ala Gly Ile Val Ile Ala Ser Pro Ser Thr Ser
                35                  40                  45

Asn Pro Asn Tyr Leu Tyr Thr Trp Thr Arg Asp Ser Ser Leu Val Phe
            50                  55                  60

Lys Ala Leu Ile Asp Gln Phe Thr Thr Gly Glu Asp Thr Ser Leu Arg
 65                  70                  75

Thr Leu Ile Asp Glu Phe Thr Ser Ala Glu Ala Ile Leu Gln Gln Val
```

```
            80                  85                  90
Pro Asn Pro Ser Gly Thr Val Ser Thr Gly Gly Leu Gly Glu Pro Lys
 95                 100                 105                 110

Phe Asn Ile Asp Glu Thr Ala Phe Thr Asp Ala Trp Gly Arg Pro Gln
            115                 120                 125

Arg Asp Gly Pro Ala Leu Arg Ala Thr Ala Ile Ile Thr Tyr Ala Asn
                130                 135                 140

Trp Leu Leu Asp Asn Lys Asn Thr Thr Tyr Val Thr Asn Thr Leu Trp
            145                 150                 155

Pro Ile Ile Lys Leu Asp Leu Asp Tyr Val Ala Ser Asn Trp Asn Gln
            160                 165                 170

Ser Thr Phe Asp Leu Trp Glu Glu Ile Asn Ser Ser Phe Phe Thr
175                 180                 185                 190

Thr Ala Val Gln His Arg Ala Leu Arg Glu Gly Ala Thr Phe Ala Asn
                195                 200                 205

Arg Ile Gly Gln Thr Ser Val Val Ser Gly Tyr Thr Thr Gln Ala Asn
                210                 215                 220

Asn Leu Leu Cys Phe Leu Gln Ser Tyr Trp Asn Pro Thr Gly Gly Tyr
            225                 230                 235

Ile Thr Ala Asn Thr Gly Gly Arg Ser Gly Lys Asp Ala Asn Thr
240                 245                 250

Val Leu Thr Ser Ile His Thr Phe Asp Pro Ala Ala Gly Cys Asp Ala
255                 260                 265                 270

Val Thr Phe Gln Pro Cys Ser Asp Lys Ala Leu Ser Asn Leu Lys Val
                275                 280                 285

Tyr Val Asp Ala Phe Arg Ser Ile Tyr Ser Ile Asn Ser Gly Ile Ala
                290                 295                 300

Ser Asn Ala Ala Val Ala Thr Gly Arg Tyr Pro Glu Asp Ser Tyr Met
            305                 310                 315

Gly Gly Asn Pro Trp Tyr Leu Thr Thr Ser Ala Val Ala Glu Gln Leu
            320                 325                 330

Tyr Asp Ala Leu Ile Val Trp Asn Lys Leu Gly Ala Leu Asn Val Thr
335                 340                 345                 350

Ser Thr Ser Leu Pro Phe Gln Gln Phe Ser Ser Gly Val Thr Val
                355                 360                 365

Gly Thr Tyr Ala Ser Ser Ser Thr Phe Lys Thr Leu Thr Ser Ala
                370                 375                 380

Ile Lys Thr Phe Ala Asp Gly Phe Leu Ala Val Asn Ala Lys Tyr Thr
            385                 390                 395

Pro Ser Asn Gly Gly Leu Ala Glu Gln Tyr Ser Arg Ser Asn Gly Ser
400                 405                 410

Pro Val Ser Ala Val Asp Leu Thr Trp Ser Tyr Ala Ala Leu Thr
415                 420                 425                 430

Ser Phe Ala Ala Arg Ser Gly Lys Thr Tyr Ala Ser Trp Gly Ala Ala
                435                 440                 445

Gly Leu Thr Val Pro Thr Thr Cys Ser Gly Ser Gly Gly Ala Gly Thr
            450                 455                 460

Val Ala Val Thr Phe Asn Val Gln Ala Thr Thr Val Phe Gly Glu Asn
            465                 470                 475

Ile Tyr Ile Thr Gly Ser Val Pro Ala Leu Gln Asn Trp Ser Pro Asp
            480                 485                 490

Asn Ala Leu Ile Leu Ser Ala Ala Asn Tyr Pro Thr Trp Ser Ile Thr
495                 500                 505                 510
```

```
Val Asn Leu Pro Ala Ser Thr Thr Ile Glu Tyr Lys Tyr Ile Arg Lys
            515                 520                 525

Phe Asn Gly Ala Val Thr Trp Glu Ser Asp Pro Asn Asn Ser Ile Thr
        530                 535                 540

Thr Pro Ala Ser Gly Thr Phe Thr Gln Asn Asp Thr Trp Arg
        545                 550                 555

<210> SEQ ID NO 15
<211> LENGTH: 583
<212> TYPE: PRT
<213> ORGANISM: Rhizomucor pusillus
<220> FEATURE:
<221> NAME/KEY: misc_feature
<223> OTHER INFORMATION: Rhizomucor pusillus alpha-amylase with
      Aspergillus niger glucoamylase linker and SBD

<400> SEQUENCE: 15

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
    50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
        115                 120                 125

Asp Ala Ser Leu Tyr His Pro Lys Cys Thr Ile Asp Tyr Asn Asp Gln
    130                 135                 140

Thr Ser Ile Glu Gln Cys Trp Val Ala Asp Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
            180                 185                 190

His Ile Arg Lys Asp Phe Trp Thr Gly Tyr Ala Glu Ala Ala Gly Val
        195                 200                 205

Phe Ala Thr Gly Glu Val Phe Asn Gly Asp Pro Ala Tyr Val Gly Pro
    210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270

Thr Thr Phe Val Asp Asn His Asp Asn Pro Arg Phe Leu Asn Ser Gln
        275                 280                 285

Ser Asp Lys Ala Leu Phe Lys Asn Ala Leu Thr Tyr Val Leu Leu Gly
    290                 295                 300
```

```
Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
            325                 330                 335

Thr Ser Ser Asp Leu Tyr Gln Phe Ile Lys Thr Val Asn Ser Val Arg
        340                 345                 350

Met Lys Ser Asn Lys Ala Val Tyr Met Asp Ile Tyr Val Gly Asp Asn
    355                 360                 365

Ala Tyr Ala Phe Lys His Gly Asp Ala Leu Val Val Leu Asn Asn Tyr
370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
            405                 410                 415

Val Ser Ser Asp Gly Thr Val Thr Phe Asn Leu Lys Asp Gly Leu Pro
        420                 425                 430

Ala Ile Phe Thr Ser Ala Thr Gly Gly Thr Thr Thr Thr Ala Thr Pro
    435                 440                 445

Thr Gly Ser Gly Ser Val Thr Ser Thr Ser Lys Thr Thr Ala Thr Ala
450                 455                 460

Ser Lys Thr Ser Thr Ser Thr Ser Ser Thr Ser Cys Thr Thr Pro Thr
465                 470                 475                 480

Ala Val Ala Val Thr Phe Asp Leu Thr Ala Thr Thr Thr Tyr Gly Glu
            485                 490                 495

Asn Ile Tyr Leu Val Gly Ser Ile Ser Gln Leu Gly Asp Trp Glu Thr
        500                 505                 510

Ser Asp Gly Ile Ala Leu Ser Ala Asp Lys Tyr Thr Ser Ser Asp Pro
    515                 520                 525

Leu Trp Tyr Val Thr Val Thr Leu Pro Ala Gly Glu Ser Phe Glu Tyr
530                 535                 540

Lys Phe Ile Arg Ile Glu Ser Asp Asp Ser Val Glu Trp Glu Ser Asp
545                 550                 555                 560

Pro Asn Arg Glu Tyr Thr Val Pro Gln Ala Cys Gly Thr Ser Thr Ala
            565                 570                 575

Thr Val Thr Asp Thr Trp Arg
        580

<210> SEQ ID NO 16
<211> LENGTH: 661
<212> TYPE: PRT
<213> ORGANISM: Trichoderma reesei
<220> FEATURE:
<221> NAME/KEY: mat_peptide
<222> LOCATION: (1)..(661)

<400> SEQUENCE: 16

Leu Tyr Ile Asn Gly Ser Val Ile Ala Pro Cys Asp Ser Pro Ile Tyr
1               5                   10                  15

Cys His Gly Asp Ile Leu Arg Glu Ile Glu Leu Ala His Pro Phe Ser
            20                  25                  30

Asp Ser Lys Thr Phe Val Asp Met Pro Ala Lys Arg Pro Leu Ser Glu
        35                  40                  45

Ile Gln Thr Ala Phe Ala Asn Leu Pro Lys Pro Leu Arg Asn Asp Ser
    50                  55                  60

Ser Leu Gln Thr Phe Leu Ala Ser Tyr Phe Ala Asp Ala Gly Gly Glu
65                  70                  75                  80
```

```
Leu Ile Gln Val Pro Arg Ala Asn Leu Thr Thr Asn Pro Thr Phe Leu
                85                  90                  95

Ser Lys Ile Asn Asp Thr Val Ile Glu Gln Phe Val Thr Gln Val Ile
            100                 105                 110

Asp Ile Trp Pro Asp Leu Thr Arg Arg Tyr Ala Gly Asp Ala Ala Val
        115                 120                 125

Lys Asn Cys Ser Ser Cys Pro Asn Ser Phe Ile Pro Val Asn Arg Thr
    130                 135                 140

Phe Val Val Ala Gly Gly Arg Phe Arg Glu Pro Tyr Tyr Trp Asp Ser
145                 150                 155                 160

Tyr Trp Ile Val Glu Gly Leu Leu Arg Thr Gly Gly Ala Phe Val Gly
                165                 170                 175

Ile Ala Arg Asn Thr Ile Asp Asn Phe Leu Asp Phe Ile Glu Arg Phe
            180                 185                 190

Gly Phe Val Pro Asn Gly Ala Arg Leu Tyr Tyr Leu Asn Arg Ser Gln
        195                 200                 205

Pro Pro Leu Leu Ser Arg Met Val Lys Val Tyr Ile Asp His Thr Asn
    210                 215                 220

Asp Thr Ala Ile Leu Arg Arg Ala Leu Pro Leu Leu Val Lys Glu His
225                 230                 235                 240

Glu Phe Trp Thr Arg Asn Arg Thr Val Asp Val Arg Val Asn Asn Lys
                245                 250                 255

Thr Tyr Val Leu Asn Gln Tyr Ala Val Gln Asn Thr Gln Pro Arg Pro
            260                 265                 270

Glu Ser Phe Arg Glu Asp Phe Gln Thr Ala Asn Asn Arg Ser Tyr Tyr
        275                 280                 285

Ala Ala Ser Gly Ile Ile Tyr Pro Ala Thr Lys Pro Leu Asn Glu Ser
    290                 295                 300

Gln Ile Glu Glu Leu Tyr Ala Asn Leu Ala Ser Gly Ala Glu Ser Gly
305                 310                 315                 320

Asn Asp Tyr Thr Ala Arg Trp Leu Ala Asp Pro Ser Asp Ala Met Arg
                325                 330                 335

Asp Val Tyr Phe Pro Leu Arg Ser Leu Asn Asn Lys Asp Ile Val Pro
            340                 345                 350

Val Asp Leu Asn Ser Ile Leu Tyr Gly Asn Glu Leu Ala Ile Ala Gln
        355                 360                 365

Phe Tyr Asn Gln Thr Gly Asn Thr Thr Ala Ala Arg Glu Trp Ser Ser
    370                 375                 380

Leu Ala Ala Asn Arg Ser Ala Ser Ile Gln Ala Val Phe Trp Asn Glu
385                 390                 395                 400

Thr Leu Phe Ser Tyr Phe Asp Tyr Asn Leu Thr Ser Ser Ser Gln Asn
                405                 410                 415

Ile Tyr Val Pro Leu Asp Lys Asp Ala Val Ala Leu Asp Arg Gln Thr
            420                 425                 430

Ala Pro Pro Gly Lys Gln Val Leu Phe His Val Gly Gln Phe Tyr Pro
        435                 440                 445

Phe Trp Thr Gly Ala Ala Pro Glu Tyr Leu Arg Asn Asn Pro Phe Ala
    450                 455                 460

Val Thr Arg Ile Phe Asp Arg Val Lys Ser Tyr Leu Asp Thr Arg Pro
465                 470                 475                 480

Gly Gly Ile Pro Ala Ser Asn Val Asn Thr Gly Gln Gln Trp Asp Gln
                485                 490                 495
```

```
Pro Asn Val Trp Pro Pro His Met His Ile Leu Met Glu Ser Leu Asn
                500             505                 510

Ser Val Pro Ala Thr Phe Ser Glu Ala Asp Pro Ala Tyr Gln Asp Val
            515                 520                 525

Arg Asn Leu Ser Leu Arg Leu Gly Gln Arg Tyr Leu Asp Phe Thr Phe
        530                 535                 540

Cys Thr Trp Arg Ala Thr Gly Gly Ser Thr Ser Glu Thr Pro Lys Leu
545                 550                 555                 560

Gln Gly Leu Thr Asp Gln Asp Val Gly Ile Met Phe Glu Lys Tyr Asn
                565                 570                 575

Asp Asn Ser Thr Asn Ala Ala Gly Gly Gly Glu Tyr Gln Val Val
            580                 585                 590

Glu Gly Phe Gly Trp Thr Asn Gly Val Leu Leu Trp Thr Ala Asp Thr
        595                 600                 605

Phe Gly Ser Gln Leu Lys Arg Pro Gln Cys Gly Asn Ile Met Ala Gly
    610                 615                 620

His Pro Ala Pro Ser Lys Arg Ser Ala Val Gln Leu Asp Met Trp Asp
625                 630                 635                 640

Ala Ser Arg Val Lys Lys Phe Gly Arg Arg Ala Glu Gly Arg Met Gly
                645                 650                 655

Thr Leu His Ala Trp
                660

<210> SEQ ID NO 17
<211> LENGTH: 177
<212> TYPE: PRT
<213> ORGANISM: Thermoascus aurantiacus

<400> SEQUENCE: 17

Thr Arg Ile Ser Ser Cys Ser Gly Ser Arg Gln Ser Ala Leu Thr Thr
1               5                   10                  15

Ala Leu Arg Asn Ala Ala Ser Leu Ala Asn Ala Ala Asp Ala Ala
            20                  25                  30

Gln Ser Gly Ser Ala Ser Lys Phe Ser Glu Tyr Phe Lys Thr Thr Ser
        35                  40                  45

Ser Ser Thr Arg Gln Thr Val Ala Ala Arg Leu Arg Ala Val Ala Arg
    50                  55                  60

Glu Ala Ser Ser Ser Ser Gly Ala Thr Thr Tyr Tyr Cys Asp Asp
65                  70                  75                  80

Pro Tyr Gly Tyr Cys Ser Ser Asn Val Leu Ala Tyr Thr Leu Pro Ser
                85                  90                  95

Tyr Asn Ile Ile Ala Asn Cys Asp Ile Phe Tyr Thr Tyr Leu Pro Ala
                100                 105                 110

Leu Thr Ser Thr Cys His Ala Gln Asp Gln Ala Thr Thr Ala Leu His
            115                 120                 125

Glu Phe Thr His Ala Pro Gly Val Tyr Ser Pro Gly Thr Asp Asp Leu
        130                 135                 140

Ala Tyr Gly Tyr Gln Ala Ala Met Gly Leu Ser Ser Ser Gln Ala Val
145                 150                 155                 160

Met Asn Ala Asp Thr Tyr Ala Leu Tyr Ala Asn Ala Ile Tyr Leu Gly
                165                 170                 175

Cys

<210> SEQ ID NO 18
<211> LENGTH: 515
```

```
<212> TYPE: PRT
<213> ORGANISM: Bacillus stearothermophilus

<400> SEQUENCE: 18

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400
```

```
Asp Tyr Leu Asp His Ser Asp Ile Ile Gly Trp Thr Arg Glu Gly Val
            405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
            485                 490                 495

Arg Pro Trp Thr Gly Glu Phe Val Arg Trp Thr Glu Pro Arg Leu Val
            500                 505                 510

Ala Trp Pro
       515

<210> SEQ ID NO 19
<211> LENGTH: 573
<212> TYPE: PRT
<213> ORGANISM: Gloeophyllum sepiarium

<400> SEQUENCE: 19

Met Tyr Arg Phe Leu Val Cys Ala Leu Gly Leu Ala Ala Ser Val Leu
1               5                   10                  15

Ala Gln Ser Val Asp Ser Tyr Val Ser Ser Glu Gly Pro Ile Ala Lys
            20                  25                  30

Ala Gly Val Leu Ala Asn Ile Gly Pro Asn Gly Ser Lys Ala Ser Gly
        35                  40                  45

Ala Ser Ala Gly Val Val Ala Ser Pro Ser Thr Ser Asp Pro Asp
50                  55                  60

Tyr Trp Tyr Thr Trp Thr Arg Asp Ser Ser Leu Val Phe Lys Ser Leu
65                  70                  75                  80

Ile Asp Gln Tyr Thr Thr Gly Ile Asp Ser Thr Ser Ser Leu Arg Thr
            85                  90                  95

Leu Ile Asp Asp Phe Val Thr Ala Glu Ala Asn Leu Gln Gln Val Ser
            100                 105                 110

Asn Pro Ser Gly Thr Leu Thr Thr Gly Gly Leu Gly Glu Pro Lys Phe
        115                 120                 125

Asn Val Asp Glu Thr Ala Phe Thr Gly Ala Trp Gly Arg Pro Gln Arg
    130                 135                 140

Asp Gly Pro Ala Leu Arg Ser Thr Ala Leu Ile Thr Tyr Gly Asn Trp
145                 150                 155                 160

Leu Leu Ser Asn Gly Asn Thr Ser Tyr Val Thr Ser Asn Leu Trp Pro
            165                 170                 175

Ile Ile Gln Asn Asp Leu Gly Tyr Val Val Ser Tyr Trp Asn Gln Ser
        180                 185                 190

Thr Tyr Asp Leu Trp Glu Glu Val Asp Ser Ser Phe Phe Thr Thr
    195                 200                 205

Ala Val Gln His Arg Ala Leu Arg Glu Gly Ala Ala Phe Ala Thr Ala
        210                 215                 220

Ile Gly Gln Thr Ser Gln Val Ser Ser Tyr Thr Thr Gln Ala Asp Asn
225                 230                 235                 240

Leu Leu Cys Phe Leu Gln Ser Tyr Trp Asn Pro Ser Gly Gly Tyr Ile
```

```
                245                 250                 255
Thr Ala Asn Thr Gly Gly Arg Ser Gly Lys Asp Ala Asn Thr Leu
            260                 265                 270

Leu Ala Ser Ile His Thr Tyr Asp Pro Ser Ala Gly Cys Asp Ala Ala
            275                 280                 285

Thr Phe Gln Pro Cys Ser Asp Lys Ala Leu Ser Asn Leu Lys Val Tyr
290                 295                 300

Val Asp Ser Phe Arg Ser Val Tyr Ser Ile Asn Ser Gly Val Ala Ser
305                 310                 315                 320

Asn Ala Ala Val Ala Thr Gly Arg Tyr Pro Glu Asp Ser Tyr Gln Gly
                325                 330                 335

Gly Asn Pro Trp Tyr Leu Thr Thr Phe Ala Val Ala Glu Gln Leu Tyr
            340                 345                 350

Asp Ala Leu Asn Val Trp Glu Ser Gln Gly Ser Leu Glu Val Thr Ser
            355                 360                 365

Thr Ser Leu Ala Phe Phe Gln Gln Phe Ser Ser Gly Val Thr Ala Gly
        370                 375                 380

Thr Tyr Ser Ser Ser Ser Ser Thr Tyr Ser Thr Leu Thr Ser Ala Ile
385                 390                 395                 400

Lys Asn Phe Ala Asp Gly Phe Val Ala Ile Asn Ala Lys Tyr Thr Pro
                405                 410                 415

Ser Asn Gly Gly Leu Ala Glu Gln Tyr Ser Lys Ser Asp Gly Ser Pro
            420                 425                 430

Leu Ser Ala Val Asp Leu Thr Trp Ser Tyr Ala Ser Ala Leu Thr Ala
            435                 440                 445

Phe Glu Ala Arg Asn Asn Thr Gln Phe Ala Gly Trp Gly Ala Ala Gly
        450                 455                 460

Leu Thr Val Pro Ser Ser Cys Ser Gly Asn Ser Gly Gly Pro Thr Val
465                 470                 475                 480

Ala Val Thr Phe Asn Val Asn Ala Glu Thr Val Trp Gly Glu Asn Ile
                485                 490                 495

Tyr Leu Thr Gly Ser Val Asp Ala Leu Glu Asn Trp Ser Ala Asp Asn
            500                 505                 510

Ala Leu Leu Leu Ser Ser Ala Asn Tyr Pro Thr Trp Ser Ile Thr Val
            515                 520                 525

Asn Leu Pro Ala Ser Thr Ala Ile Glu Tyr Lys Tyr Ile Arg Lys Asn
        530                 535                 540

Asn Gly Ala Val Thr Trp Glu Ser Asp Pro Asn Asn Ser Ile Thr Thr
545                 550                 555                 560

Pro Ala Ser Gly Ser Thr Thr Glu Asn Asp Thr Trp Arg
                565                 570

<210> SEQ ID NO 20
<211> LENGTH: 559
<212> TYPE: PRT
<213> ORGANISM: Gloephyllum trabeum

<400> SEQUENCE: 20

Gln Ser Val Asp Ser Tyr Val Gly Ser Glu Gly Pro Ile Ala Lys Ala
1               5                   10                  15

Gly Val Leu Ala Asn Ile Gly Pro Asn Gly Ser Lys Ala Ser Gly Ala
            20                  25                  30

Ala Ala Gly Val Val Val Ala Ser Pro Ser Lys Ser Asp Pro Asp Tyr
        35                  40                  45
```

```
Trp Tyr Thr Trp Thr Arg Asp Ser Ser Leu Val Phe Lys Ser Leu Ile
    50              55                  60
Asp Gln Tyr Thr Thr Gly Ile Asp Ser Thr Ser Ser Leu Arg Ser Leu
65              70                  75                  80
Ile Asp Ser Phe Val Ile Ala Glu Ala Asn Ile Gln Gln Val Ser Asn
                85                  90                  95
Pro Ser Gly Thr Leu Thr Thr Gly Gly Leu Gly Glu Pro Lys Phe Asn
            100                 105                 110
Val Asp Glu Thr Ala Phe Thr Gly Ala Trp Gly Arg Pro Gln Arg Asp
            115                 120                 125
Gly Pro Ala Leu Arg Ala Thr Ala Leu Ile Thr Tyr Gly Asn Trp Leu
        130                 135                 140
Leu Ser Asn Gly Asn Thr Thr Trp Val Thr Ser Thr Leu Trp Pro Ile
145                 150                 155                 160
Ile Gln Asn Asp Leu Asn Tyr Val Val Gln Tyr Trp Asn Gln Thr Thr
                165                 170                 175
Phe Asp Leu Trp Glu Glu Val Asn Ser Ser Phe Phe Thr Thr Ala
            180                 185                 190
Val Gln His Arg Ala Leu Arg Glu Gly Ala Ala Phe Ala Thr Lys Ile
        195                 200                 205
Gly Gln Thr Ser Ser Val Ser Ser Tyr Thr Thr Gln Ala Ala Asn Leu
    210                 215                 220
Leu Cys Phe Leu Gln Ser Tyr Trp Asn Pro Thr Ser Gly Tyr Ile Thr
225                 230                 235                 240
Ala Asn Thr Gly Gly Gly Arg Ser Gly Lys Asp Ala Asn Thr Leu Leu
                245                 250                 255
Ala Ser Ile His Thr Tyr Asp Pro Ser Ala Gly Cys Asp Ala Thr Thr
            260                 265                 270
Phe Gln Pro Cys Ser Asp Lys Ala Leu Ser Asn Leu Lys Val Tyr Val
            275                 280                 285
Asp Ser Phe Arg Ser Val Tyr Ser Ile Asn Ser Gly Ile Ala Ser Asn
        290                 295                 300
Ala Ala Val Ala Thr Gly Arg Tyr Pro Glu Asp Ser Tyr Gln Gly Gly
305                 310                 315                 320
Asn Pro Trp Tyr Leu Thr Thr Phe Ala Val Ala Glu Gln Leu Tyr Asp
                325                 330                 335
Ala Leu Asn Val Trp Ala Ala Gln Gly Ser Leu Asn Val Thr Ser Ile
            340                 345                 350
Ser Leu Pro Phe Phe Gln Gln Phe Ser Ser Ser Val Thr Ala Gly Thr
            355                 360                 365
Tyr Ala Ser Ser Ser Thr Thr Tyr Thr Thr Leu Thr Ser Ala Ile Lys
    370                 375                 380
Ser Phe Ala Asp Gly Phe Val Ala Ile Asn Ala Gln Tyr Thr Pro Ser
385                 390                 395                 400
Asn Gly Gly Leu Ala Glu Gln Phe Ser Arg Ser Asn Gly Ala Pro Val
                405                 410                 415
Ser Ala Val Asp Leu Thr Trp Ser Tyr Ala Ser Ala Leu Thr Ala Phe
            420                 425                 430
Glu Ala Arg Asn Asn Thr Gln Phe Ala Gly Trp Gly Ala Val Gly Leu
        435                 440                 445
Thr Val Pro Thr Ser Cys Ser Ser Asn Ser Gly Gly Gly Gly Ser
    450                 455                 460
Thr Val Ala Val Thr Phe Asn Val Asn Ala Gln Thr Val Trp Gly Glu
```

```
                465                 470                 475                 480
Asn Ile Tyr Ile Thr Gly Ser Val Asp Ala Leu Ser Asn Trp Ser Pro
                    485                 490                 495

Asp Asn Ala Leu Leu Ser Ser Ala Asn Tyr Pro Thr Trp Ser Ile
                500                 505                 510

Thr Val Asn Leu Pro Ala Ser Thr Ala Ile Gln Tyr Lys Tyr Ile Arg
                    515                 520                 525

Lys Asn Asn Gly Ala Val Thr Trp Glu Ser Asp Pro Asn Asn Ser Ile
                530                 535                 540

Thr Thr Pro Ala Ser Gly Ser Val Thr Glu Asn Asp Thr Trp Arg
545                 550                 555

<210> SEQ ID NO 21
<211> LENGTH: 250
<212> TYPE: PRT
<213> ORGANISM: Thermoascus aurantiacus

<400> SEQUENCE: 21

Met Ser Phe Ser Lys Ile Ile Ala Thr Ala Gly Val Leu Ala Ser Ala
1               5                   10                  15

Ser Leu Val Ala Gly His Gly Phe Val Gln Asn Ile Val Ile Asp Gly
                20                  25                  30

Lys Lys Tyr Tyr Gly Gly Tyr Leu Val Asn Gln Tyr Pro Tyr Met Ser
            35                  40                  45

Asn Pro Pro Glu Val Ile Ala Trp Ser Thr Thr Ala Thr Asp Leu Gly
        50                  55                  60

Phe Val Asp Gly Thr Gly Tyr Gln Thr Pro Asp Ile Ile Cys His Arg
65                  70                  75                  80

Gly Ala Lys Pro Gly Ala Leu Thr Ala Pro Val Ser Pro Gly Gly Thr
                85                  90                  95

Val Glu Leu Gln Trp Thr Pro Trp Pro Asp Ser His His Gly Pro Val
                100                 105                 110

Ile Asn Tyr Leu Ala Pro Cys Asn Gly Asp Cys Ser Thr Val Asp Lys
            115                 120                 125

Thr Gln Leu Glu Phe Phe Lys Ile Ala Glu Ser Gly Leu Ile Asn Asp
        130                 135                 140

Asp Asn Pro Pro Gly Ile Trp Ala Ser Asp Asn Leu Ile Ala Ala Asn
145                 150                 155                 160

Asn Ser Trp Thr Val Thr Ile Pro Thr Thr Ile Ala Pro Gly Asn Tyr
                165                 170                 175

Val Leu Arg His Glu Ile Ile Ala Leu His Ser Ala Gln Asn Gln Asp
            180                 185                 190

Gly Ala Gln Asn Tyr Pro Gln Cys Ile Asn Leu Gln Val Thr Gly Gly
        195                 200                 205

Gly Ser Asp Asn Pro Ala Gly Thr Leu Gly Thr Ala Leu Tyr His Asp
    210                 215                 220

Thr Asp Pro Gly Ile Leu Ile Asn Ile Tyr Gln Lys Leu Ser Ser Tyr
225                 230                 235                 240

Ile Ile Pro Gly Pro Pro Leu Tyr Thr Gly
                245                 250

<210> SEQ ID NO 22
<211> LENGTH: 413
<212> TYPE: PRT
<213> ORGANISM: Pyrococcus furiosus
```

```
<400> SEQUENCE: 22

Ala Glu Leu Glu Gly Leu Asp Glu Ser Ala Gln Val Met Ala Thr
1               5                   10                  15

Tyr Val Trp Asn Leu Gly Tyr Asp Gly Ser Gly Ile Thr Ile Gly Ile
            20                  25                  30

Ile Asp Thr Gly Ile Asp Ala Ser His Pro Asp Leu Gln Gly Lys Val
                35                  40                  45

Ile Gly Trp Val Asp Phe Val Asn Gly Arg Ser Tyr Pro Tyr Asp Asp
    50                  55                  60

His Gly His Gly Thr His Val Ala Ser Ile Ala Ala Gly Thr Gly Ala
65              70                  75                  80

Ala Ser Asn Gly Lys Tyr Lys Gly Met Ala Pro Gly Ala Lys Leu Ala
                85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
            115                 120                 125

Lys Val Ile Asn Leu Ser Leu Gly Ser Ser Gln Ser Ser Asp Gly Thr
130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                165                 170                 175

Ser Pro Ala Ala Ala Ser Lys Val Ile Thr Val Gly Ala Val Asp Lys
            180                 185                 190

Tyr Asp Val Ile Thr Ser Phe Ser Ser Arg Gly Pro Thr Ala Asp Gly
    195                 200                 205

Arg Leu Lys Pro Glu Val Val Ala Pro Gly Asn Trp Ile Ile Ala Ala
210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

Thr Ala Leu Ile Glu Thr Ala Asp Ile Val Lys Pro Asp Glu Ile Ala
            275                 280                 285

Asp Ile Ala Tyr Gly Ala Gly Arg Val Asn Ala Tyr Lys Ala Ile Asn
    290                 295                 300

Tyr Asp Asn Tyr Ala Lys Leu Val Phe Thr Gly Tyr Val Ala Asn Lys
305                 310                 315                 320

Gly Ser Gln Thr His Gln Phe Val Ile Ser Gly Ala Ser Phe Val Thr
                325                 330                 335

Ala Thr Leu Tyr Trp Asp Asn Ala Asn Ser Asp Leu Asp Leu Tyr Leu
            340                 345                 350

Tyr Asp Pro Asn Gly Asn Gln Val Asp Tyr Ser Tyr Thr Ala Tyr Tyr
    355                 360                 365

Asp Phe Glu Lys Val Gly Tyr Tyr Asn Pro Thr Asp Gly Thr Trp Thr
370                 375                 380

Ile Lys Val Val Ser Tyr Ser Gly Ser Ala Asn Tyr Gln Val Asp Val
385                 390                 395                 400

Val Ser Asp Gly Ser Leu Ser Gln Pro Gly Ser Ser Pro
                405                 410
```

<210> SEQ ID NO 23
<211> LENGTH: 595
<212> TYPE: PRT
<213> ORGANISM: Penicillium oxalicum

<400> SEQUENCE: 23

```
Arg Pro Asp Pro Lys Gly Gly Asn Leu Thr Pro Phe Ile His Lys Glu
1               5                   10                  15

Gly Glu Arg Ser Leu Gln Gly Ile Leu Asp Asn Leu Gly Gly Arg Gly
            20                  25                  30

Lys Lys Thr Pro Gly Thr Ala Ala Gly Leu Phe Ile Ala Ser Pro Asn
        35                  40                  45

Thr Glu Asn Pro Asn Tyr Tyr Tyr Thr Trp Thr Arg Asp Ser Ala Leu
50                  55                  60

Thr Ala Lys Cys Leu Ile Asp Leu Phe Glu Asp Ser Arg Ala Lys Phe
65                  70                  75                  80

Pro Ile Asp Arg Lys Tyr Leu Glu Thr Gly Ile Arg Asp Tyr Lys Ser
                85                  90                  95

Ser Gln Ala Ile Leu Gln Ser Val Ser Asn Pro Ser Gly Thr Leu Lys
            100                 105                 110

Asp Gly Ser Gly Leu Gly Glu Pro Lys Phe Glu Ile Asp Leu Asn Pro
        115                 120                 125

Phe Ser Gly Ala Trp Gly Arg Pro Gln Arg Asp Gly Pro Ala Leu Arg
130                 135                 140

Ala Thr Ala Met Ile Thr Tyr Ala Asn Tyr Leu Ile Ser His Gly Gln
145                 150                 155                 160

Lys Ser Asp Val Ser Gln Val Met Trp Pro Ile Ile Ala Asn Asp Leu
                165                 170                 175

Ala Tyr Val Gly Gln Tyr Trp Asn Asn Thr Gly Phe Asp Leu Trp Glu
            180                 185                 190

Glu Val Asp Gly Ser Ser Phe Phe Thr Ile Ala Val Gln His Arg Ala
        195                 200                 205

Leu Val Glu Gly Ser Gln Leu Ala Lys Lys Leu Gly Lys Ser Cys Asp
210                 215                 220

Ala Cys Asp Ser Gln Pro Pro Gln Ile Leu Cys Phe Leu Gln Ser Phe
225                 230                 235                 240

Trp Asn Gly Lys Tyr Ile Thr Ser Asn Ile Asn Thr Gln Ala Ser Arg
                245                 250                 255

Ser Gly Ile Asp Leu Asp Ser Val Leu Gly Ser Ile His Thr Phe Asp
            260                 265                 270

Pro Glu Ala Ala Cys Asp Asp Ala Thr Phe Gln Pro Cys Ser Ala Arg
        275                 280                 285

Ala Leu Ala Asn His Lys Val Tyr Val Asp Ser Phe Arg Ser Ile Tyr
290                 295                 300

Lys Ile Asn Ala Gly Leu Ala Glu Gly Ser Ala Ala Asn Val Gly Arg
305                 310                 315                 320

Tyr Pro Glu Asp Val Tyr Gln Gly Gly Asn Pro Trp Tyr Leu Ala Thr
                325                 330                 335

Leu Gly Ala Ser Glu Leu Leu Tyr Asp Ala Leu Tyr Gln Trp Asp Arg
            340                 345                 350

Leu Gly Lys Leu Glu Val Ser Glu Thr Ser Leu Ser Phe Phe Lys Asp
        355                 360                 365

Phe Asp Ala Thr Val Lys Ile Gly Ser Tyr Ser Arg Asn Ser Lys Thr
```

```
           370                375                380
Tyr Lys Lys Leu Thr Gln Ser Ile Lys Ser Tyr Ala Asp Gly Phe Ile
385                 390                395                400

Gln Leu Val Gln Gln Tyr Thr Pro Ser Asn Gly Ser Leu Ala Glu Gln
                405                410                415

Tyr Asp Arg Asn Thr Ala Ala Pro Leu Ser Ala Asn Asp Leu Thr Trp
            420                425                430

Ser Phe Ala Ser Phe Leu Thr Ala Thr Gln Arg Arg Asp Ala Val Val
        435                440                445

Pro Pro Ser Trp Gly Ala Lys Ser Ala Asn Lys Val Pro Thr Thr Cys
    450                455                460

Ser Ala Ser Pro Val Val Gly Thr Tyr Lys Ala Pro Thr Ala Thr Phe
465                470                475                480

Ser Ser Lys Thr Lys Cys Val Pro Ala Lys Asp Ile Val Pro Ile Thr
                485                490                495

Phe Tyr Leu Ile Glu Asn Thr Tyr Tyr Gly Glu Asn Val Phe Met Ser
                500                505                510

Gly Asn Ile Thr Ala Leu Gly Asn Trp Asp Ala Lys Lys Gly Phe Pro
            515                520                525

Leu Thr Ala Asn Leu Tyr Thr Gln Asp Gln Asn Leu Trp Phe Ala Ser
530                535                540

Val Glu Phe Ile Pro Ala Gly Thr Pro Phe Glu Tyr Lys Tyr Tyr Lys
545                550                555                560

Val Glu Pro Asn Gly Asp Ile Thr Trp Glu Lys Gly Pro Asn Arg Val
                565                570                575

Phe Val Ala Pro Thr Gly Cys Pro Val Gln Pro His Ser Asn Asp Val
                580                585                590

Trp Gln Phe
        595

<210> SEQ ID NO 24
<211> LENGTH: 39
<212> TYPE: DNA
<213> ORGANISM: Artificial Sequence
<220> FEATURE:
<223> OTHER INFORMATION: Primer KKSC0334-F

<400> SEQUENCE: 24
acacaactgg ggatccacca tgacgctccg acacctcgg                              39

<210> SEQ ID NO 25
<211> LENGTH: 38
<212> TYPE: DNA
<213> ORGANISM: Artificial Sequence
<220> FEATURE:
<223> OTHER INFORMATION: Primer KKSC0334-R

<400> SEQUENCE: 25
ctagatctcg agaagctttc acgacctcct ccctaccc                               38

<210> SEQ ID NO 26
<211> LENGTH: 39
<212> TYPE: DNA
<213> ORGANISM: Artificial Sequence
<220> FEATURE:
<223> OTHER INFORMATION: Promer KKSC0335-F

<400> SEQUENCE: 26
acacaactgg ggatccacca tggcgctacg acacatcgc                              39
```

<210> SEQ ID NO 27
<211> LENGTH: 41
<212> TYPE: DNA
<213> ORGANISM: Artificial Sequence
<220> FEATURE:
<223> OTHER INFORMATION: Primer KKSC0335-R

<400> SEQUENCE: 27
ctagatctcg agaagctttt acgagacgga gacactaaac a                                  41

<210> SEQ ID NO 28
<211> LENGTH: 573
<212> TYPE: PRT
<213> ORGANISM: Pycnoporus sanguineus
<220> FEATURE:
<221> NAME/KEY: SIGNAL
<222> LOCATION: (1)..(18)

<400> SEQUENCE: 28

Met Arg Phe Thr Leu Leu Ala Ser Leu Ile Gly Leu Ala Val Gly Ala
1               5                   10                  15

Phe Ala Gln Ser Ser Ala Val Asp Ala Tyr Val Ala Ser Glu Ser Pro
            20                  25                  30

Ile Ala Lys Gln Gly Val Leu Asn Asn Ile Gly Pro Asn Gly Ser Lys
        35                  40                  45

Ala His Gly Ala Lys Ala Gly Ile Val Val Ala Ser Pro Ser Thr Glu
    50                  55                  60

Asn Pro Asp Tyr Leu Tyr Thr Trp Thr Arg Asp Ser Ser Leu Val Phe
65                  70                  75                  80

Lys Leu Leu Ile Asp Gln Phe Thr Ser Gly Asp Asp Thr Ser Leu Arg
                85                  90                  95

Gly Leu Ile Asp Asp Phe Thr Ser Ala Glu Ala Ile Leu Gln Gln Val
            100                 105                 110

Ser Asn Pro Ser Gly Thr Val Ser Thr Gly Gly Leu Gly Glu Pro Lys
        115                 120                 125

Phe Asn Ile Asp Glu Thr Ala Phe Thr Gly Ala Trp Gly Arg Pro Gln
    130                 135                 140

Arg Asp Gly Pro Ala Leu Arg Ala Thr Ser Ile Ile Arg Tyr Ala Asn
145                 150                 155                 160

Trp Leu Leu Asp Asn Gly Asn Thr Thr Tyr Val Ser Asn Thr Leu Trp
                165                 170                 175

Pro Val Ile Gln Leu Asp Leu Asp Tyr Val Ala Asp Asn Trp Asn Gln
            180                 185                 190

Ser Thr Phe Asp Leu Trp Glu Glu Val Asp Ser Ser Phe Phe Thr
        195                 200                 205

Thr Ala Val Gln His Arg Ala Leu Arg Glu Gly Ala Thr Phe Ala Ser
    210                 215                 220

Arg Ile Gly Gln Ser Ser Val Val Ser Gly Tyr Thr Thr Gln Ala Asp
225                 230                 235                 240

Asn Leu Leu Cys Phe Leu Gln Ser Tyr Trp Asn Pro Ser Gly Gly Tyr
                245                 250                 255

Val Thr Ala Asn Thr Gly Gly Gly Arg Ser Gly Lys Asp Ser Asn Thr
            260                 265                 270

Val Leu Thr Ser Ile His Thr Phe Asp Pro Ala Ala Gly Cys Asp Ala
        275                 280                 285

Ala Thr Phe Gln Pro Cys Ser Asp Lys Ala Leu Ser Asn Leu Lys Val

```
                290                 295                 300
Tyr Val Asp Ala Phe Arg Ser Ile Tyr Thr Ile Asn Asn Gly Ile Ala
305                 310                 315                 320

Ser Asn Ala Ala Val Ala Thr Gly Arg Tyr Pro Glu Asp Ser Tyr Met
                325                 330                 335

Gly Gly Asn Pro Trp Tyr Leu Thr Thr Ser Ala Val Ala Glu Gln Leu
            340                 345                 350

Tyr Asp Ala Leu Tyr Val Trp Asp Gln Leu Gly Gly Leu Asn Val Thr
        355                 360                 365

Ser Thr Ser Leu Ala Phe Phe Gln Gln Phe Ala Ser Gly Leu Ser Thr
370                 375                 380

Gly Thr Tyr Ser Ala Ser Ser Thr Tyr Ala Thr Leu Thr Ser Ala
385                 390                 395                 400

Ile Arg Ser Phe Ala Asp Gly Phe Leu Ala Ile Asn Ala Lys Tyr Thr
                405                 410                 415

Pro Ala Asp Gly Gly Leu Ala Glu Gln Tyr Ser Arg Asn Asp Gly Thr
            420                 425                 430

Pro Leu Ser Ala Val Asp Leu Thr Trp Ser Tyr Ala Ala Ala Leu Thr
        435                 440                 445

Ala Phe Ala Ala Arg Glu Gly Lys Thr Tyr Gly Ser Trp Gly Ala Ala
450                 455                 460

Gly Leu Thr Val Pro Ala Ser Cys Ser Gly Gly Gly Ala Thr Val
465                 470                 475                 480

Ala Val Thr Phe Asn Val Gln Ala Thr Val Phe Gly Glu Asn Ile
                485                 490                 495

Tyr Ile Thr Gly Ser Val Ala Ala Leu Gln Asn Trp Ser Pro Asp Asn
            500                 505                 510

Ala Leu Ile Leu Ser Ala Asn Tyr Pro Thr Trp Ser Ile Thr Val
        515                 520                 525

Asn Leu Pro Ala Asn Thr Val Val Gln Tyr Lys Tyr Ile Arg Lys Phe
530                 535                 540

Asn Gly Gln Val Thr Trp Glu Ser Asp Pro Asn Asn Gln Ile Thr Thr
545                 550                 555                 560

Pro Ser Gly Gly Ser Phe Thr Gln Asn Asp Val Trp Arg
                565                 570

<210> SEQ ID NO 29
<211> LENGTH: 2829
<212> TYPE: DNA
<213> ORGANISM: Myceliophthora sepedonium
<220> FEATURE:
<221> NAME/KEY: misc_signal
<222> LOCATION: (40)..(100)
<220> FEATURE:
<221> NAME/KEY: CDS
<222> LOCATION: (101)..(279)
<220> FEATURE:
<221> NAME/KEY: Intron
<222> LOCATION: (280)..(365)
<220> FEATURE:
<221> NAME/KEY: CDS
<222> LOCATION: (366)..(1025)
<220> FEATURE:
<221> NAME/KEY: Intron
<222> LOCATION: (1026)..(1083)
<220> FEATURE:
<221> NAME/KEY: CDS
<222> LOCATION: (1084)..(2326)

<400> SEQUENCE: 29
```

```
tgccctcctc ggggccttcc tcgttctctc ccatccttcg ggtacaacag accatcatcg         60
taagcgcaag acagcaccac cgcgtgctga agctacaca atg gcg cta cga cac           115
                                            Met Ala Leu Arg His
                                             1               5 atc gcg gcg gcg gcg atc gcc ggt ctt gcc tca agg act gca gcg ctg          163
Ile Ala Ala Ala Ala Ile Ala Gly Leu Ala Ser Arg Thr Ala Ala Leu
                10                  15                  20 tac atc aat ggc tca gtc aca gcg ccg tgc gac tcg ccc att tac tgc          211
Tyr Ile Asn Gly Ser Val Thr Ala Pro Cys Asp Ser Pro Ile Tyr Cys
            25                  30                  35 caa ggc gag ctt cta aaa gcg gtt gaa ctg gcg cgt cct ttc gtt gac          259
Gln Gly Glu Leu Leu Lys Ala Val Glu Leu Ala Arg Pro Phe Val Asp
        40                  45                  50 agc aag aca ttt gtg gac at  gtaagtcatg atcggccagc caggtgggaa             309
Ser Lys Thr Phe Val Asp Met
    55                  60 tgcagccggc gggcagattc gtggtgacac actgactgac ttggattccc gcccag g          366 ccc acg atc aag cca gtg gat gaa gtg ctt gca gca ttc agc aag ctt          414
Pro Thr Ile Lys Pro Val Asp Glu Val Leu Ala Ala Phe Ser Lys Leu
                65                  70                  75 agc cta cca ctt tcc aat aac tca gag ctc aac gcc ttc ttg tat gag          462
Ser Leu Pro Leu Ser Asn Asn Ser Glu Leu Asn Ala Phe Leu Tyr Glu
            80                  85                  90 aac ttc gcc cag gct ggc cac gag ctc gaa gaa gtg ccc gac agt gag          510
Asn Phe Ala Gln Ala Gly His Glu Leu Glu Glu Val Pro Asp Ser Glu
        95                  100                 105 cta gag acg gac gca aag ttc ctc gac aag ctc gag gat cgc acc atc          558
Leu Glu Thr Asp Ala Lys Phe Leu Asp Lys Leu Glu Asp Arg Thr Ile
    110                 115                 120 aag gag ttc gtc ggc aag gtg atc gac atc tgg ccc gac ttg acc agg          606
Lys Glu Phe Val Gly Lys Val Ile Asp Ile Trp Pro Asp Leu Thr Arg
125                 130                 135                 140 cgc tat gcc ggc ccc agc aac tgc acc gag tgc gcc aac agc ttc att          654
Arg Tyr Ala Gly Pro Ser Asn Cys Thr Glu Cys Ala Asn Ser Phe Ile
                145                 150                 155 ccc gtg aac cgc acg ttc gtc gtg gct ggc ggt cgc ttc cga gag ccc          702
Pro Val Asn Arg Thr Phe Val Val Ala Gly Gly Arg Phe Arg Glu Pro
            160                 165                 170 tac tat tgg gat tcg tac tgg atc gtc gaa ggt ctc ctg cgc act ggc          750
Tyr Tyr Trp Asp Ser Tyr Trp Ile Val Glu Gly Leu Leu Arg Thr Gly
        175                 180                 185 ggt gcc ttc acc cat atc tcc aag aac atc att gag aac ttc ctg gac          798
Gly Ala Phe Thr His Ile Ser Lys Asn Ile Ile Glu Asn Phe Leu Asp
    190                 195                 200 ttt gtc gac acg att ggc ttc att ccc aat ggc gcc agg atc tac tac          846
Phe Val Asp Thr Ile Gly Phe Ile Pro Asn Gly Ala Arg Ile Tyr Tyr
205                 210                 215                 220 ctg aac agg tca cag ccc cct ctc ctg aca ttg atg gtg aag agc tac          894
Leu Asn Arg Ser Gln Pro Pro Leu Leu Thr Leu Met Val Lys Ser Tyr
                225                 230                 235 gtc gac tac acc aac gac acg agc atc ctg gac agg gcc ttg ccg ctg          942
Val Asp Tyr Thr Asn Asp Thr Ser Ile Leu Asp Arg Ala Leu Pro Leu
            240                 245                 250 ctg atc aag gag cac gag ttc ttc atg aat aac cgg acg gtg tcc atc          990
Leu Ile Lys Glu His Glu Phe Phe Met Asn Asn Arg Thr Val Ser Ile
        255                 260                 265 acg gga tcg aac ggc aag gag tac act ctg aac ag gtaagcgagg               1035
Thr Gly Ser Asn Gly Lys Glu Tyr Thr Leu Asn Arg
    270                 275                 280
```

```
tggacaggca ggcctcggcg accatgcgct tattgttgta tctggcag g tat cac        1090
                                                    Tyr His gtt gaa aac aac caa cca cgc cca gag tcg ttc cgg gag gat tac att      1138
Val Glu Asn Asn Gln Pro Arg Pro Glu Ser Phe Arg Glu Asp Tyr Ile
            285                 290                 295 acc gct aac aac ggc tcc tac tac gcg tct tcg gga ata ata tat ccc      1186
Thr Ala Asn Asn Gly Ser Tyr Tyr Ala Ser Ser Gly Ile Ile Tyr Pro
300                 305                 310 gtt aag acg ccc ctc aac gag acg gaa aag gcc gcg ctc tac tcg aac      1234
Val Lys Thr Pro Leu Asn Glu Thr Glu Lys Ala Ala Leu Tyr Ser Asn
315                 320                 325                 330 cta gca acc ggc gcc gag tcc ggc tgg gac tac acc tcc cga tgg ctt      1282
Leu Ala Thr Gly Ala Glu Ser Gly Trp Asp Tyr Thr Ser Arg Trp Leu
            335                 340                 345 ggg gtc ccc agc gac gct gcg agg gac gtc tat ttc ccg ctc cgc tcg      1330
Gly Val Pro Ser Asp Ala Ala Arg Asp Val Tyr Phe Pro Leu Arg Ser
            350                 355                 360 ctt aat gtc cgc gac ata gtc ccc gtc gat ctc aac tcc atc ctc tac      1378
Leu Asn Val Arg Asp Ile Val Pro Val Asp Leu Asn Ser Ile Leu Tyr
            365                 370                 375 cag aac gag gtg atc att gcc gag tac ctc gag aag gcc ggt aac tcc      1426
Gln Asn Glu Val Ile Ile Ala Glu Tyr Leu Glu Lys Ala Gly Asn Ser
380                 385                 390 tcc gcg gcc aag cgc ttc gcc act gct gcc gaa cag cgc agc gag gcc      1474
Ser Ala Ala Lys Arg Phe Ala Thr Ala Ala Glu Gln Arg Ser Glu Ala
395                 400                 405                 410 atg tac tcc ctc atg tgg aac gcc acg cac tgg tct tac ttt gac tac      1522
Met Tyr Ser Leu Met Trp Asn Ala Thr His Trp Ser Tyr Phe Asp Tyr
            415                 420                 425 aat ctg acc gat aac acg caa cac atc ttc gtc cca gcc gac gag gac      1570
Asn Leu Thr Asp Asn Thr Gln His Ile Phe Val Pro Ala Asp Glu Asp
            430                 435                 440 acc gcc ccc cag gac cgg atc gag gcc ccc ccc ggt caa caa gtc ttc      1618
Thr Ala Pro Gln Asp Arg Ile Glu Ala Pro Pro Gly Gln Gln Val Phe
            445                 450                 455 ttc cac att gcg cag ctc tat cca ttc tgg acg ggc gcg gcc ccc gcc      1666
Phe His Ile Ala Gln Leu Tyr Pro Phe Trp Thr Gly Ala Ala Pro Ala
460                 465                 470 agc ctt aag gct aac ccc ctc gcg gtg cag caa gcc tac gcc cgt gtg      1714
Ser Leu Lys Ala Asn Pro Leu Ala Val Gln Gln Ala Tyr Ala Arg Val
475                 480                 485                 490 gcg cgc atg ctc gat atc aag aag ggc gcc atc ccc gcc acc aac tac      1762
Ala Arg Met Leu Asp Ile Lys Lys Gly Ala Ile Pro Ala Thr Asn Tyr
            495                 500                 505 cgc acc ggc caa caa tgg gac cag ccc aac gtc tgg ccg ccg ctg caa      1810
Arg Thr Gly Gln Gln Trp Asp Gln Pro Asn Val Trp Pro Pro Leu Gln
            510                 515                 520 cat atc ctg atg aag ggc ctg ctt aac acc ccg gca acc ttt ggc aag      1858
His Ile Leu Met Lys Gly Leu Leu Asn Thr Pro Ala Thr Phe Gly Lys
            525                 530                 535 tcc gac cct gcg tac cag agc gtg caa aac ctc gcc ctg cgt ctc gcc      1906
Ser Asp Pro Ala Tyr Gln Ser Val Gln Asn Leu Ala Leu Arg Leu Ala
540                 545                 550 cag cgc tac ctc gat tcc acc ttt tgt acc tgg tac gcc acg ggc ggt      1954
Gln Arg Tyr Leu Asp Ser Thr Phe Cys Thr Trp Tyr Ala Thr Gly Gly
555                 560                 565                 570 tca acc agc gac ttc ccg cag ctg gag ggt gtt acc ccg ggc gct acg      2002
Ser Thr Ser Asp Phe Pro Gln Leu Glu Gly Val Thr Pro Gly Ala Thr
            575                 580                 585
```

```
ggc gtc atg ttt gag aag tac gcc gac aat gct acc aac gtt gcc ggc    2050
Gly Val Met Phe Glu Lys Tyr Ala Asp Asn Ala Thr Asn Val Ala Gly
            590                 595                 600 ggc ggc ggc gaa tac gag gtc gtc gag ggt ttc ggg tgg acc aat ggc    2098
Gly Gly Gly Glu Tyr Glu Val Val Glu Gly Phe Gly Trp Thr Asn Gly
        605                 610                 615 gta ctg atc tgg gcg gcc gac gtc ttt ggt aac aag ctc aag cgc ccg    2146
Val Leu Ile Trp Ala Ala Asp Val Phe Gly Asn Lys Leu Lys Arg Pro
    620                 625                 630 gac tgc ggc aac atc acg gcc gca cat acc cac tct agt gcc aag aga    2194
Asp Cys Gly Asn Ile Thr Ala Ala His Thr His Ser Ser Ala Lys Arg
635                 640                 645                 650 ggt ctg gaa gag aat aag ctg ccg agg agg gcg gtg gag ctc gac ccg    2242
Gly Leu Glu Glu Asn Lys Leu Pro Arg Arg Ala Val Glu Leu Asp Pro
                655                 660                 665 tgg gat gcc gcg tgg acc aag atg ttt ggg cgg agt aag ctc cgg aga    2290
Trp Asp Ala Ala Trp Thr Lys Met Phe Gly Arg Ser Lys Leu Arg Arg
            670                 675                 680 aga gag gca gaa gat gtg cgg aag cgg tgg atg agc taaggtccta         2336
Arg Glu Ala Glu Asp Val Arg Lys Arg Trp Met Ser
        685                 690 atccatatgc ttaatgaagg gtggttcgtt gtgcttcgct ttcaagttgg taacttagtg  2396
tttagtgtct ccgtctcgta agcgatggca aactttgcga gggaagtcgg tcgatgaaga  2456
ggtaatccgc atcctggcgc cctatctagg tcggtagcta cctgggcgga tatcgagctt  2516
acattaatac ctactagta atttccagag agatgatcac ctggattgcg gctgcaaatg  2576
gttaacacac acaataagat aagaatgtta ttgctgccca tgtacagaca cggttgtaga  2636
atgagcttga taaagctgac aacggaaaac tggacccccc ggtttgcgca taaatgtccc  2696
gccaacgcca aaagttcaac cctccaaccg ccaccgtagc aacgccgata caaatgcaac  2756
cgtgtatttt ctccgtcatg ccgccgtagc ccctattcac acactcggct caaaccgctg  2816
tcgtcaccgg cgt                                                    2829

<210> SEQ ID NO 30
<211> LENGTH: 694
<212> TYPE: PRT
<213> ORGANISM: Myceliophthora sepedonium

<400> SEQUENCE: 30

Met Ala Leu Arg His Ile Ala Ala Ala Ile Ala Gly Leu Ala Ser
1               5                   10                  15

Arg Thr Ala Ala Leu Tyr Ile Asn Gly Ser Val Thr Ala Pro Cys Asp
            20                  25                  30

Ser Pro Ile Tyr Cys Gln Gly Glu Leu Leu Lys Ala Val Glu Leu Ala
        35                  40                  45

Arg Pro Phe Val Asp Ser Lys Thr Phe Val Asp Met Pro Thr Ile Lys
    50                  55                  60

Pro Val Asp Glu Val Leu Ala Ala Phe Ser Lys Leu Ser Leu Pro Leu
65                  70                  75                  80

Ser Asn Asn Ser Glu Leu Asn Ala Phe Leu Tyr Glu Asn Phe Ala Gln
                85                  90                  95

Ala Gly His Glu Leu Glu Glu Val Pro Asp Ser Glu Leu Glu Thr Asp
            100                 105                 110

Ala Lys Phe Leu Asp Lys Leu Glu Asp Arg Thr Ile Lys Glu Phe Val
        115                 120                 125

Gly Lys Val Ile Asp Ile Trp Pro Asp Leu Thr Arg Arg Tyr Ala Gly
```

```
              130                 135                 140
Pro Ser Asn Cys Thr Glu Cys Ala Asn Ser Phe Ile Pro Val Asn Arg
145                 150                 155                 160

Thr Phe Val Val Ala Gly Gly Arg Phe Arg Glu Pro Tyr Tyr Trp Asp
                165                 170                 175

Ser Tyr Trp Ile Val Glu Gly Leu Leu Arg Thr Gly Gly Ala Phe Thr
            180                 185                 190

His Ile Ser Lys Asn Ile Ile Glu Asn Phe Leu Asp Phe Val Asp Thr
            195                 200                 205

Ile Gly Phe Ile Pro Asn Gly Ala Arg Ile Tyr Tyr Leu Asn Arg Ser
            210                 215                 220

Gln Pro Pro Leu Leu Thr Leu Met Val Lys Ser Tyr Val Asp Tyr Thr
225                 230                 235                 240

Asn Asp Thr Ser Ile Leu Asp Arg Ala Leu Pro Leu Leu Ile Lys Glu
                245                 250                 255

His Glu Phe Phe Met Asn Asn Arg Thr Val Ser Ile Thr Gly Ser Asn
                260                 265                 270

Gly Lys Glu Tyr Thr Leu Asn Arg Tyr His Val Glu Asn Asn Gln Pro
            275                 280                 285

Arg Pro Glu Ser Phe Arg Glu Asp Tyr Ile Thr Ala Asn Asn Gly Ser
            290                 295                 300

Tyr Tyr Ala Ser Ser Gly Ile Ile Tyr Pro Val Lys Thr Pro Leu Asn
305                 310                 315                 320

Glu Thr Glu Lys Ala Ala Leu Tyr Ser Asn Leu Ala Thr Gly Ala Glu
                325                 330                 335

Ser Gly Trp Asp Tyr Thr Ser Arg Trp Leu Gly Val Pro Ser Asp Ala
                340                 345                 350

Ala Arg Asp Val Tyr Phe Pro Leu Arg Ser Leu Asn Val Arg Asp Ile
            355                 360                 365

Val Pro Val Asp Leu Asn Ser Ile Leu Tyr Gln Asn Glu Val Ile Ile
            370                 375                 380

Ala Glu Tyr Leu Glu Lys Ala Gly Asn Ser Ser Ala Ala Lys Arg Phe
385                 390                 395                 400

Ala Thr Ala Ala Glu Gln Arg Ser Glu Ala Met Tyr Ser Leu Met Trp
                405                 410                 415

Asn Ala Thr His Trp Ser Tyr Phe Asp Tyr Asn Leu Thr Asp Asn Thr
            420                 425                 430

Gln His Ile Phe Val Pro Ala Asp Glu Asp Thr Ala Pro Gln Asp Arg
            435                 440                 445

Ile Glu Ala Pro Pro Gly Gln Gln Val Phe Phe His Ile Ala Gln Leu
450                 455                 460

Tyr Pro Phe Trp Thr Gly Ala Ala Pro Ala Ser Leu Lys Ala Asn Pro
465                 470                 475                 480

Leu Ala Val Gln Gln Ala Tyr Ala Arg Val Ala Arg Met Leu Asp Ile
                485                 490                 495

Lys Lys Gly Ala Ile Pro Ala Thr Asn Tyr Arg Thr Gly Gln Gln Trp
            500                 505                 510

Asp Gln Pro Asn Val Trp Pro Leu Gln His Ile Leu Met Lys Gly
            515                 520                 525

Leu Leu Asn Thr Pro Ala Thr Phe Gly Lys Ser Asp Pro Ala Tyr Gln
            530                 535                 540

Ser Val Gln Asn Leu Ala Leu Arg Leu Ala Gln Arg Tyr Leu Asp Ser
545                 550                 555                 560
```

```
Thr Phe Cys Thr Trp Tyr Ala Thr Gly Gly Ser Thr Ser Asp Phe Pro
                565                 570                 575

Gln Leu Glu Gly Val Thr Pro Gly Ala Thr Gly Val Met Phe Glu Lys
            580                 585                 590

Tyr Ala Asp Asn Ala Thr Asn Val Ala Gly Gly Gly Tyr Glu
            595                 600                 605

Val Val Glu Gly Phe Gly Trp Thr Asn Gly Val Leu Ile Trp Ala Ala
        610                 615                 620

Asp Val Phe Gly Asn Lys Leu Lys Arg Pro Asp Cys Gly Asn Ile Thr
625                 630                 635                 640

Ala Ala His Thr His Ser Ser Ala Lys Arg Gly Leu Glu Glu Asn Lys
                645                 650                 655

Leu Pro Arg Arg Ala Val Glu Leu Asp Pro Trp Asp Ala Ala Trp Thr
                660                 665                 670

Lys Met Phe Gly Arg Ser Lys Leu Arg Arg Glu Ala Glu Asp Val
                675                 680                 685

Arg Lys Arg Trp Met Ser
    690

<210> SEQ ID NO 31
<211> LENGTH: 1079
<212> TYPE: PRT
<213> ORGANISM: Trichoderma reesei
<220> FEATURE:
<221> NAME/KEY: SIGNAL
<222> LOCATION: (1)..(23)
<220> FEATURE:
<221> NAME/KEY: mat_peptide
<222> LOCATION: (24)..(1079)

<400> SEQUENCE: 31

Met Arg Ser Thr Val Thr Ser Ala Ala Ala Leu Leu Ser Leu Leu Gln
            -20                 -15                 -10

Leu Val Ser Pro Val His Gly Thr Thr Leu Val Asp Arg Val Thr Lys
        -5                  -1  1                   5

Cys Leu Ser Arg His Asp Gly Ser Asp Ala Glu Ser His Phe Ser Lys
10                  15                  20                  25

Asn Val Tyr Lys Thr Asp Phe Ala Gly Val Thr Trp Asp Glu Asp Asn
                30                  35                  40

Trp Leu Leu Ser Thr Thr Gln Leu Lys Gln Gly Ala Phe Glu Ala Arg
            45                  50                  55

Gly Ser Val Ala Asn Gly Tyr Leu Gly Ile Asn Val Ala Ser Val Gly
        60                  65                  70

Pro Phe Phe Glu Val Asp Thr Glu Glu Asp Gly Asp Val Ile Ser Gly
    75                  80                  85

Trp Pro Leu Phe Ser Arg Arg Gln Ser Phe Ala Thr Val Ala Gly Phe
90                  95                  100                 105

Trp Asp Ala Gln Pro Gln Met Asn Gly Thr Asn Phe Pro Trp Leu Ser
                110                 115                 120

Gln Tyr Gly Ser Asp Thr Ala Ile Ser Gly Ile Pro His Trp Ser Gly
            125                 130                 135

Leu Val Leu Asp Leu Gly Gly Thr Tyr Leu Asp Ala Thr Val Ser
        140                 145                 150

Asn Lys Thr Ile Ser His Phe Arg Ser Thr Tyr Asp Tyr Lys Ala Gly
    155                 160                 165

Val Leu Ser Trp Ser Tyr Lys Trp Thr Pro Lys Gly Asn Lys Gly Ser
```

```
                170             175             180             185
        Phe Asp Ile Ser Tyr Arg Leu Phe Ala Asn Lys Leu His Val Asn Gln
                        190             195             200
        Ala Val Val Asp Met Gln Val Thr Ala Ser Lys Asn Val Gln Ala Ser
                        205             210             215
        Ile Val Asn Val Leu Asp Gly Phe Ala Ala Val Arg Thr Asp Phe Val
                        220             225             230
        Glu Ser Gly Glu Asp Gly Ser Ala Ile Phe Ala Ala Val Arg Pro Asn
                        235             240             245
        Gly Val Ala Asn Val Thr Ala Tyr Val Tyr Ala Asp Ile Thr Gly Ser
        250             255             260             265
        Gly Gly Val Asn Leu Ser Ser Arg Lys Ile Val His Asn Lys Pro Tyr
                        270             275             280
        Val His Ala Asn Ala Ser Ser Ile Ala Gln Ala Val Pro Val Lys Phe
                        285             290             295
        Ala Ala Gly Arg Thr Val Arg Val Thr Lys Phe Val Gly Ala Ala Ser
                        300             305             310
        Ser Asp Ala Phe Lys Asn Pro Lys Gln Val Ala Lys Lys Ala Ala Ala
                        315             320             325
        Ala Gly Leu Ser Asn Gly Tyr Thr Lys Ser Leu Lys Ala His Val Glu
        330             335             340             345
        Glu Trp Ala Thr Val Met Pro Glu Ser Ser Val Asp Ser Phe Ala Asp
                        350             355             360
        Pro Lys Thr Gly Lys Leu Pro Ala Asp Ser His Ile Val Asp Ser Ala
                        365             370             375
        Ile Ile Ala Val Thr Asn Thr Tyr Tyr Leu Leu Gln Asn Thr Val Gly
                        380             385             390
        Lys Asn Gly Ile Lys Ala Val Asp Gly Ala Pro Val Asn Val Asp Ser
                        395             400             405
        Ile Ser Val Gly Gly Leu Thr Ser Asp Ser Tyr Ala Gly Gln Ile Phe
        410             415             420             425
        Trp Asp Ala Asp Leu Trp Met Gln Pro Gly Leu Val Ala Ala His Pro
                        430             435             440
        Glu Ala Ala Glu Arg Ile Thr Asn Tyr Arg Leu Ala Arg Tyr Gly Gln
                        445             450             455
        Ala Lys Glu Asn Val Lys Thr Ala Tyr Ala Gly Ser Gln Asn Glu Thr
                        460             465             470
        Phe Phe Ser Ala Ser Ala Ala Val Phe Pro Trp Thr Ser Gly Arg Tyr
                        475             480             485
        Gly Asn Cys Thr Ala Thr Gly Pro Cys Trp Asp Tyr Glu Tyr His Leu
        490             495             500             505
        Asn Gly Asp Ile Gly Ile Ser Leu Val Asn Gln Trp Val Val Asn Gly
                        510             515             520
        Asp Thr Lys Asp Phe Glu Lys Asn Leu Phe Pro Val Tyr Asp Ser Val
                        525             530             535
        Ala Gln Leu Tyr Gly Asn Leu Leu Arg Pro Asn Lys Thr Ser Trp Thr
                        540             545             550
        Leu Thr Asn Met Thr Asp Pro Asp Glu Tyr Ala Asn His Val Asp Ala
                        555             560             565
        Gly Gly Tyr Thr Met Pro Leu Ile Ala Glu Thr Leu Gln Lys Ala Asn
        570             575             580             585
        Ser Phe Arg Gln Gln Phe Gly Ile Glu Gln Asn Lys Thr Trp Asn Asp
                        590             595             600
```

```
Met Ala Ser Asn Val Leu Val Leu Arg Glu Asn Gly Val Thr Leu Glu
            605                 610                 615

Phe Thr Ala Met Asn Gly Thr Ala Val Val Lys Gln Ala Asp Val Ile
            620                 625                 630

Met Leu Thr Tyr Pro Leu Ser Tyr Gly Thr Asn Tyr Ser Ala Gln Asp
            635                 640                 645

Ala Leu Asn Asp Leu Asp Tyr Tyr Ala Asn Lys Gln Ser Pro Asp Gly
650                 655                 660                 665

Pro Ala Met Thr Tyr Ala Phe Phe Ser Ile Val Ala Asn Glu Ile Ser
            670                 675                 680

Pro Ser Gly Cys Ser Ala Tyr Thr Tyr Ala Gln Asn Ala Phe Lys Pro
            685                 690                 695

Tyr Val Arg Ala Pro Phe Tyr Gln Ile Ser Glu Gln Leu Ile Asp Asp
            700                 705                 710

Ala Ser Val Asn Gly Gly Thr His Pro Ala Tyr Pro Phe Leu Thr Gly
            715                 720                 725

His Gly Gly Ala His Gln Val Val Leu Phe Gly Tyr Leu Gly Leu Arg
730                 735                 740                 745

Leu Val Pro Asp Asp Val Ile His Ile Glu Pro Asn Leu Pro Pro Gln
            750                 755                 760

Ile Pro Tyr Leu Arg Tyr Arg Thr Phe Tyr Trp Arg Gly Trp Pro Ile
            765                 770                 775

Ser Ala Trp Ser Asn Tyr Thr His Thr Thr Leu Ser Arg Ala Ala Gly
            780                 785                 790

Val Ala Ala Leu Glu Gly Ala Asp Gln Arg Phe Ala Arg Lys Pro Ile
            795                 800                 805

Thr Ile His Ala Gly Pro Glu Gln Asp Pro Thr Ala Tyr Arg Leu Pro
810                 815                 820                 825

Val Lys Gly Ser Val Ile Pro Asn Lys Gln Ile Gly Ser Gln Gln
            830                 835                 840

Thr Tyr Ala Gly Asn Leu Val Gln Cys His Ala Ala Ser Ser Pro Asn
            845                 850                 855

Asp Tyr Val Pro Gly Gln Phe Pro Ile Ala Ala Val Asp Gly Ala Thr
            860                 865                 870

Ser Thr Lys Trp Gln Pro Ala Ser Ala Asp Lys Val Ser Ser Ile Thr
            875                 880                 885

Val Ser Leu Asp Lys Glu Asp Val Gly Ser Leu Val Ser Gly Phe His
890                 895                 900                 905

Phe Asp Trp Ala Gln Ala Pro Pro Val Asn Ala Thr Val Ile Phe His
            910                 915                 920

Asp Glu Ala Leu Ala Asp Pro Ala Thr Ala Leu Ala Ser Ala His Lys
            925                 930                 935

His Asn Ser Lys Tyr Thr Thr Val Thr Ser Leu Thr Asn Ile Glu Leu
            940                 945                 950

Ser Asp Pro Tyr Val Ser Thr Lys Asp Leu Asn Ala Ile Ala Ile Pro
            955                 960                 965

Ile Gly Asn Thr Thr Asn Val Thr Leu Ser His Pro Val Ala Ala Ser
970                 975                 980                 985

Arg Tyr Ala Ser Leu Leu Ile Val Gly Asn Gln Gly Leu Asp Pro Val
                990                 995                 1000

Asp Val Lys Ala Lys Asn Gly Thr Gly Ala Thr Val Ala Glu Trp
            1005                1010                1015
```

-continued

```
Ala Ile Phe Gly His Gly Lys Glu His Ser Gly Lys Pro Ser Ser
            1020            1025            1030

His Ser Lys Arg Arg Leu Asn Val Arg Thr Ala Ala Thr Leu Ser
        1035            1040            1045

Asn Pro Arg Ser Phe Met Arg Arg Arg Leu
        1050            1055

<210> SEQ ID NO 32
<211> LENGTH: 564
<212> TYPE: PRT
<213> ORGANISM: Meripilus giganteus
<220> FEATURE:
<221> NAME/KEY: SIGNAL
<222> LOCATION: (1)..(17)
<220> FEATURE:
<221> NAME/KEY: mat_peptide
<222> LOCATION: (18)..(564)

<400> SEQUENCE: 32

Met Val Ala Thr Ser Leu Leu Val Ala Ser Leu Phe Thr Leu Ala Leu
        -15             -10                 -5

Gly Thr Pro Thr Gly Arg Asn Leu Lys Leu His Glu Ala Arg Glu Asp
-1   1              5                   10                  15

Leu Pro Ala Gly Phe Ser Leu Arg Gly Ala Ala Ser Pro Asp Thr Thr
                20                  25                  30

Leu Lys Leu Arg Ile Ala Leu Val Gln Asn Asn Phe Ala Glu Leu Glu
            35                  40                  45

Asp Lys Leu Tyr Asp Val Ser Thr Pro Ser Ser Ala Asn Tyr Gly Asn
        50                  55                  60

His Leu Ser Lys Glu Glu Val Glu Gln Tyr Ile Ala Pro Ala Pro Glu
65                  70                  75

Ser Val Lys Ala Val Asn Ala Trp Leu Thr Glu Asn Gly Leu Asp Ala
80                  85                  90                  95

His Thr Ile Ser Pro Ala Gly Asp Trp Leu Ala Phe Glu Val Pro Val
                100                 105                 110

Ser Lys Ala Asn Glu Leu Phe Asp Ala Asp Phe Ser Val Phe Thr His
            115                 120                 125

Asp Glu Ser Gly Leu Glu Ala Ile Arg Thr Leu Ala Tyr Ser Ile Pro
        130                 135                 140

Ala Glu Leu Gln Gly His Leu Asp Leu Val His Pro Thr Val Thr Phe
            145                 150                 155

Pro Asn Pro Asn Ala His Leu Pro Val Val Arg Ser Thr Gln Pro Ile
160                 165                 170                 175

Arg Asn Leu Thr Gly Arg Ala Ile Pro Ala Ser Cys Ala Ser Thr Ile
                180                 185                 190

Thr Pro Ala Cys Leu Gln Ala Ile Tyr Gly Ile Pro Thr Thr Lys Ala
            195                 200                 205

Thr Gln Ser Ser Asn Lys Leu Ala Val Ser Gly Phe Ile Asp Gln Phe
        210                 215                 220

Ala Asn Lys Ala Asp Leu Lys Ser Phe Leu Ala Gln Phe Arg Lys Asp
            225                 230                 235

Ile Ser Ser Ser Thr Thr Phe Ser Leu Gln Thr Leu Asp Gly Gly Glu
240                 245                 250                 255

Asn Asp Gln Ser Pro Ser Glu Ala Gly Ile Glu Ala Asn Leu Asp Ile
                260                 265                 270

Gln Tyr Thr Val Gly Leu Ala Thr Gly Val Pro Thr Thr Phe Ile Ser
            275                 280                 285
```

```
Val Gly Asp Asp Phe Gln Asp Gly Asn Leu Glu Gly Phe Leu Asp Ile
            290                 295                 300
Ile Asn Phe Leu Leu Gly Glu Ser Asn Pro Pro Gln Val Leu Thr Thr
    305                 310                 315
Ser Tyr Gly Gln Asn Glu Asn Thr Ile Ser Ala Lys Leu Ala Asn Gln
320                 325                 330                 335
Leu Cys Asn Ala Tyr Ala Gln Leu Gly Ala Arg Gly Thr Ser Ile Leu
                340                 345                 350
Phe Ala Ser Gly Asp Gly Gly Val Ser Gly Ser Gln Ser Ala His Cys
                355                 360                 365
Ser Asn Phe Val Pro Thr Phe Pro Ser Gly Cys Pro Phe Met Thr Ser
            370                 375                 380
Val Gly Ala Thr Gln Gly Val Ser Pro Glu Thr Ala Ala Ala Phe Ser
385                 390                 395
Ser Gly Gly Phe Ser Asn Val Phe Gly Ile Pro Ser Tyr Gln Ala Ser
400                 405                 410                 415
Ala Val Ser Gly Tyr Leu Ser Ala Leu Gly Ser Thr Asn Ser Gly Lys
                420                 425                 430
Phe Asn Arg Ser Gly Arg Gly Phe Pro Asp Val Ser Thr Gln Gly Val
            435                 440                 445
Asp Phe Gln Ile Val Ser Gly Gly Gln Thr Ile Gly Val Asp Gly Thr
            450                 455                 460
Ser Cys Ala Ser Pro Thr Phe Ala Ser Val Ile Ser Leu Val Asn Asp
    465                 470                 475
Arg Leu Ile Ala Ala Gly Lys Ser Pro Leu Gly Phe Leu Asn Pro Phe
480                 485                 490                 495
Leu Tyr Ser Ser Ala Gly Lys Ala Ala Leu Asn Asp Val Thr Ser Gly
                500                 505                 510
Ser Asn Pro Gly Cys Ser Thr Asn Gly Phe Pro Ala Lys Ala Gly Trp
            515                 520                 525
Asp Pro Val Thr Gly Leu Gly Thr Pro Asn Phe Ala Lys Leu Leu Thr
        530                 535                 540
Ala Val Gly Leu
    545
```

POLYPEPTIDES HAVING TREHALASE ACTIVITY AND THE USE THEREOF IN PROCESS OF PRODUCING FERMENTATION PRODUCTS

CROSS-REFERENCE TO RELATED APPLICATIONS

This application is a 35 U.S.C. 371 national application of PCT/US2016/037224 filed Jun. 13, 2016, which claims priority or the benefit under 35 U.S.C. 119 of U.S. application No. 62/181,538 filed Jun. 18, 2015, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having treahalase activity and polynucleotides encoding the polypeptides. The invention also relates to nucleic acid constructs, vectors, and host cells comprising the polynucleotides as well as methods of producing the polypeptides. The invention also relates to processes of producing fermentation products using a trehalase of the invention.

Description of the Related Art

Trehalose is a stable disaccharide sugar consisting of two sugar monomers (glucose). Trehalose is accumulated in yeast as a response to stress in up to 10-15% of cell dry weight (GrBa et al. (1975) Eur. J. Appl. Microbiol. 2:29-37). Trehalose cannot be metabolized by the yeast. The enzyme trehalase cleaves trehalose into two glucose units.

Trehalases are classified in EC 3.2.1.28 (alpha,alpha-trehalase) and EC. 3.2.1.93 (alpha,alpha-phosphotrehalase). The EC classes are based on recommendations of the Nomenclature Committee of the International Union of Biochemistry and Molecular Biology (IUBMB). Description of EC classes can be found on the internet. The two enzyme classes are both referred to as "trehalases". Examples of neutral trehalases include treahalases from *Saccharomyces cerevisiae* (Londesborouh et al. (1984) Characterization of two trehalases from baker's yeast" Biochem J 219, 511-518; *Mucor roxii* (Dewerchin et al (1984), "Trehalase activity and cyclic AMP content during early development of *Mucor rouxii* spores", J. Bacteriol. 158, 575-579); *Phycomyces blakesleeanus* (Thevelein et al (1983), "Glucose-induced trehalase activation and trehalose mobilization during early germination of *Phycomyces blakesleeanus* spores" J. Gen Microbiol. 129, 719-726); *Fusarium oxysporium* (Amaral et al (1996), "Comparative study of two trehalase activities from *Fusarium oxysporium* var *Linii*" Can. J Microbiol. 41, 1057-1062). Examples of neutral trehalases include, but are not limited to, trehalases from *Saccharomyces cerevisiae* (Parvaeh et al. (1996) Purification and biochemical characterization of the ATH1 gene product, vacuolar acid trehalase from *Saccharomyces cerevisae*" FEBS Lett. 391, 273-278); *Neorospora crassa* (Hecker et al (1973), "Location of trehalase in the ascospores of *Neurospora*: Relation to ascospore dormancy and germination". J. Bacteriol. 115, 592-599); *Chaetomium aureum* (Sumida et al. (1989), "Purification and some properties of trehalase from *Chaetomium aureum* MS-27. J. Ferment. Bioeng. 67, 83-86); *Aspergillus nidulans* (d'Enfert et al. (1997), "Molecular characterization of the *Aspergillus nidulans* treA gene encoding an acid trehalase required for growth on trehalose. Mol. Microbiol. 24, 203-216); *Humicola grisea* (Zimmermann et al. (1990)." Purification and properties of an extracellular conidial trehalase from *Humicola grisea* var. *thermoidea*", Biochim. Acta 1036, 41-46); *Humicola grisea* (Cardello et al. (1994), "A cytosolic trehalase from the thermophilhilic fungus *Humicola grisea* var. *thermoidea*, Microbiology UK 140, 1671-1677; *Scytalidium thermophilum* (Kadowaki et al. (1996), "Characterization of the trehalose system from the thermophilic fungus *Scytalidium thermophilum*" Biochim. Biophys. Acta 1291, 199-205); and *Fusarium oxysporium* (Amaral et al (1996), "Comparative study of two trehalase activities from *Fusarium oxysporium* var *Linii*" Can. J Microbiol. 41, 1057-1062).

A trehalase is also know from soybean (Aeschbachet et al (1999) "Purification of the trehalase GmTRE1 from soybean nodules and cloning of its cDNA", Plant Physiol 119, 489-496).

Trehalases are also present in small intestine and kidney of mammals.

WO 2009/121058 (Novozymes) concerns a method of fermenting sugars derived from plant material into a fermentation product, such as ethanol, using a fermenting organism by adding one or more trehalase into in the fermentation medium.

WO 2012/027374 (Dyadic) discloses a trehalase from *Myceliophthora thermophila* which can be used in an enzyme mixture for degrading lignocellulosic biomass to fermentable sugars.

WO 2013/148993 (Novozymes) discloses a process of producing a fermentation product, such as ethanol, from starch-containing material by liquefying, saccharifying and fermenting the starch-containing material wherein wherein a carbohydrate-source generating enzyme, a cellulolytic composition and a trehalase is present in fermentation. A trehalase from *Trichoderma reesei* is disclosed.

WO 2015/065978 (Danisco US Inc.) discloses a method of increasing the production of ethanol from a liquefact in a fermentation reaction including fermenting the liquefact with a glucoamylase, a fermenting organism and a trehalase and recovering the ethanol and other fermentation products at the end of the fermentation.

There is still a need for providing enzymes or enzyme composition suitable for use in processes for producing fermentation products, such as ethanol, in increased yields.

SUMMARY OF THE INVENTION

The present invention relates to polypeptides having treahalase activity and polynucleotides encoding the polypeptides. The invention also relates to processes of producing fermentation products using a trehalase of the invention. The trehalases concerned are E.C. 3.2.1.28 and further belong to Family 37 Glucoside Hydrolases ("GH37") as defined by CAZY (available on the world wide web).

The inventors have found, purified and characterized two trehalases (shown in SEQ ID NO: 30 herein and 4 herein, respectively) having high thermostability and a broad pH range. It was also found that an increased ethanol yield can be obtained when adding a trehalase of the invention in fermentation in a process of the invention.

A trehalase of the invention can be used in any yeast fermentation product production process, in particular ethanol production process. The treahalase can be used as an exogenous enzyme or can be expressed in a fermentation product producing organism, in particular a yeast strain producing ethanol, especially a strain of *Sacchariomyces*, in particular a *Saccharomyces cerevisiae* strain.

Accordingly, in the first aspect the present invention relates to polypeptides having trehalase activity selected from the group consisting of:
(a) a polypeptide having at least 90% sequence identity to the mature polypeptide of SEQ ID NO: 30 or SEQ ID NO: 2 or at least 80% sequence identity to the mature polypeptide of SEQ ID NO: 4;
(b) a polypeptide encoded by a polynucleotide that hybridizes under very high stringency conditions with (i) the mature polypeptide coding sequence of SEQ ID NO: 29, SEQ ID NO: 1 or SEQ ID NO: 3, (ii) the cDNA sequence thereof, or (iii) the full-length complement of (i) or (ii);
(c) a polypeptide encoded by a polynucleotide having at least 90% sequence identity to the mature polypeptide coding sequence of SEQ ID NO: 29 or SEQ ID NO: 1 or at least 80% sequence identity to the mature polypeptide coding sequence of SEQ ID NO: 3 or the cDNA sequence thereof;
(d) a variant of the mature polypeptide of SEQ ID NO: 30, SEQ ID NO: 2 or SEQ ID NO: 4 comprising a substitution, deletion, and/or insertion at one or more (e.g., several) positions; and
(e) a fragment of the polypeptide of (a), (b), (c), or (d) that has trehalase activity.

The mature polypeptide of SEQ ID NO: 30 is shown as amino acids 21-694. The mature polypeptide of SEQ ID NO: 2 is shown as amino acids 21-697. The mature polypeptide of SEQ ID NO: 4 is shown as amino acids 21-690. The signal of SEQ ID NO: 30 is shown as amino acids 1-20. The signal of SEQ ID NO: 2 is shown as amino acids 1-20. The signal of SEQ ID NO: 4 is shown as amino acids 21-690.

The present invention also relates to polynucleotides encoding the polypeptides having trehalase activity of the present invention; nucleic acid constructs; recombinant expression vectors; recombinant host cells comprising the polynucleotides; and methods of producing the polypeptides.

In an aspect the present invention also relates to processes of producing a fermentation product, in particular ethanol, comprising
(a) liquefying a starch-containing material with an alpha-amylase;
optionally pre-saccharifying the liquefied material before step (b);
(b) saccharifying the liquefied material;
(c) fermenting using a fermentation organism;
wherein
  i) a glucoamylase;
  ii) a trehalase of the invention;
  iii) optionally a cellulolytic enzyme composition and/or a protease;
are present and/or added during
  saccharification step (b);
  fermentation step (c);
  simultaneous saccharification and fermentation;
  optionally the presaccharification step before step (b).
Liquefaction in step (a) may be carried out at a temperature above the initial gelatinization temperature, in particular between 80° C.-90° C.

In an embodiment the invention relates to processes of producing fermentation products from starch-containing material comprising:
(i) saccharifying a starch-containing material at a temperature below the initial gelatinization temperature; and
(ii) fermenting using a fermentation organism;
wherein saccharification and/or fermentation is done in the presence of the following enzymes: glucoamylase, alpha-amylase, trehalase of the invention, and optionally a cellulolytic enzyme composition and/or a protease.

In an embodiment the invention relates to processes of producing a fermentation product from pretreated cellulosic material, comprising:
(a) hydrolyzing said pretreated cellulosic material with a cellulolytic enzyme composition;
(b) fermenting using a fermenting organism; and
(c) optionally recovering the fermentation product;
wherein a trehalase of the invention is added and/or present in hydrolysis step (a) and/or fermentation step (b).

In an embodiment the trehalase may be added to the thin stillage, i.e., at the backend of a starch based or a cellulosic material based process.

A trehalase of the invention may be present and/or added in saccharification/hydrolysis and/or fermentation in a fermentation product producing process of the invention in any suitable amount. In a preferred embodiment the trehalase is present and/or added in an amount between 0.01-20 ug EP trehalase/g DS, such as between 0.05-15 ug EP terhalase/g DS, such as between 0.5 and 10 ug EP trehalase/g DS.

DEFINITIONS

Figure 1:
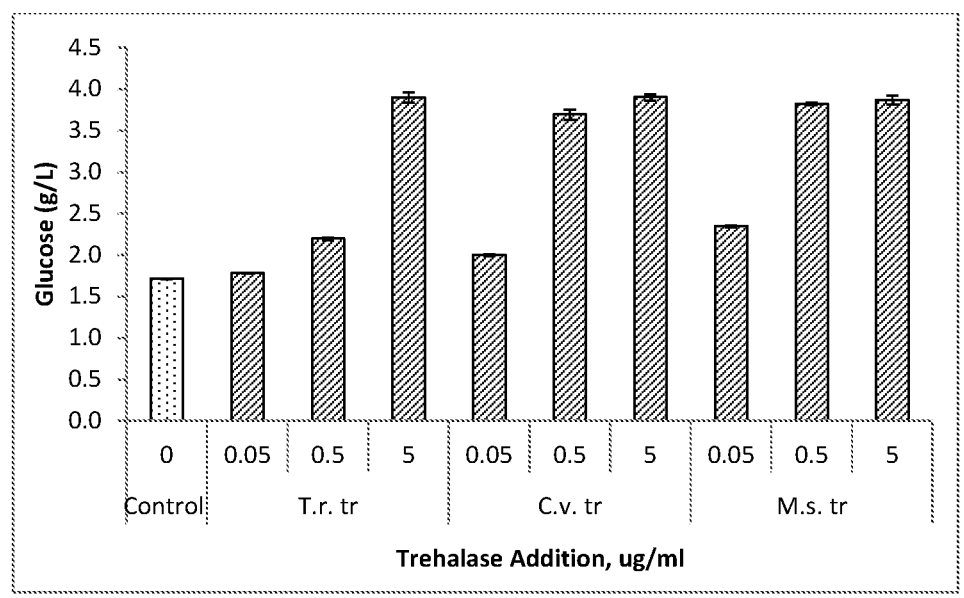
FIG. 1 shows the glucose production by trehalase addition in supernatant of ferm drop.

Trehalase: The term "trehalase" means an enzyme which degrades trehalose into its unit monosaccharides (i.e., glucose). Trehalases are classified in EC 3.2.1.28 (alpha,alpha-trehalase) and EC. 3.2.1.93 (alpha,alpha-phosphotrehalase). The EC classes are based on recommendations of the Nomenclature Committee of the International Union of Biochemistry and Molecular Biology (IUBMB). Description of EC classes can be found on the internet. Trehalases are enzymes that catalyze the following reactions:
EC 3.2.1.28:

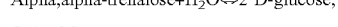
Alpha,alpha-trehalose+$H_2O \Leftrightarrow$ 2 D-glucose;

EC 3.2.1. 93:

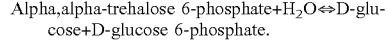
Alpha,alpha-trehalose 6-phosphate+$H_2O \Leftrightarrow$ D-glucose+D-glucose 6-phosphate.

For purposes of the present invention, trehalase activity may be determined according to "Trehalase Assay" procedure described in the "Materials & Methods"-section. In one aspect, the polypeptides of the present invention have at least 20%, e.g., at least 40%, at least 50%, at least 60%, at least 70%, at least 80%, at least 90%, at least 95%, or at least 100% of the trehalase activity of the mature polypeptide of SEQ ID NO: 30, SEQ ID NO: 2 or SEQ ID NO: 4, respectively. In a preferred embodiment a trehalase of the invention is a Family 37 Glycoside Hydrolase ("GH37 trehalase").

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (e.g., several) amino acids absent from the amino and/or carboxyl terminus of a mature polypeptide or domain; wherein the fragment has trehalase activity. In one aspect, a fragment contains at least 592 amino acid residues, at least 627 amino acid residues, or at least 662 amino acid residues of SEQ ID NO: 2. In another aspect, a fragment contains at least 587 amino acid residues, at least 621 amino acid residues, or at least 655 amino acid residues of SEQ ID NO: 4.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the invention. The fermentation broth from that host cell will comprise the isolated polypeptide.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 21 to 694 of SEQ ID NO: 30. Amino acids 1 to 20 of SEQ ID NO: 30 are the signal peptide. In one aspect, the mature polypeptide is amino acids 21 to 697 of SEQ ID NO: 2. Amino acids 1 to 20 of SEQ ID NO: 2 are a signal peptide. In another aspect, the mature polypeptide is amino acids 21 to 690 of SEQ ID NO: 4. Amino acids 1 to 20 of SEQ ID NO: 4 are a signal peptide. The signal peptides are determined using the SignalP program (Nielsen et al., 1997, Protein Engineering 10: 1-6). It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having trehalase activity.

In one aspect, the mature polypeptide coding sequence is nucleotides (101) . . . (2326) of SEQ ID NO: 29 or the cDNA sequence thereof shown as nucleotides 501-679, 366-1025, 1084-2326.

In one aspect, the mature polypeptide coding sequence is nucleotides (501) . . . (2814) of SEQ ID NO: 1 or the cDNA sequence thereof shown as nucleotides 501-679, 766-1425, 1484-2676 and 2756-2814. Nucleotides 501 to 560 of SEQ ID NO: 1 encode a signal peptide. In another aspect, the mature polypeptide coding sequence is nucleotides 501-2701 of SEQ ID NO: 3 or the cDNA sequence thereof shown as nucleotides 501-679, 752-1411, and 1471-2701. Nucleotides 501 to 560 of SEQ ID NO: 3 encode a signal peptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−
Total Number of Gaps in Alignment)

Stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.]

Subsequence: The term "subsequence" means a polynucleotide having one or more (e.g., several) nucleotides absent from the 5' and/or 3' end of a mature polypeptide coding sequence; wherein the subsequence encodes a fragment having trehalase activity. In one aspect, a subsequence contains at least 1776 nucleotides, at least 1881 nucleotides, or at least 1962 nucleotides of SEQ ID NO: 29 or SEQ ID NO: 1. In one aspect, a subsequence contains at least 1761 nucleotides, at least 1863 nucleotides, or at least 1965 nucleotides of SEQ ID NO: 3.

Variant: The term "variant" means a polypeptide having trehalase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

DETAILED DESCRIPTION OF THE INVENTION

Polypeptides Having Trehalase Activity

In an embodiment, the present invention relates to polypeptides having a sequence identity to the mature polypeptide of SEQ ID NO: 30 of at least 80, at least 85, at least 90%, at least 91%, at least 92%, at least 93%, at least 94%, at least 95%, at least 96%, at least 97%, at least 98%, at least 99%, or 100%, which have trehalase activity. In one aspect, the polypeptides differ by up to 10 amino acids, e.g., 1, 2, 3, 4, 5, 6, 7, 8, 9, or 10, from the mature polypeptide of SEQ ID NO: 30.

In an embodiment, the present invention relates to polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, which have trehalase activity. In one aspect, the polypeptides differ by up to 10 amino acids, e.g., 1, 2, 3, 4, 5, 6, 7, 8, 9, or 10, from the mature polypeptide of SEQ ID NO: 2.

In a particular embodiment the invention relates to polypeptides having a sequence identity to the mature polypeptide of SEQ ID NO: 30 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the trehalase activity of the mature polypeptide of SEQ ID NO: 30.

In a particular embodiment the invention relates to polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the trehalase activity of the mature polypeptide ofSEQ ID NO: 2.

In a particular embodiment the invention relates to polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 75% of the trehalase activity of the mature polypeptide of SEQ ID NO: 30 or SEQ ID NO: 2.

In a particular embodiment the invention relates to polypeptides having a sequence identity to the mature polypeptide of SEQ ID NO: 30 or SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the trehalase activity of the mature polypeptide of SEQ ID NO: 30 or SEQ ID NO: 2.

In a particular embodiment the invention relates to polypeptides having a sequence identity to the mature polypeptide of SEQ ID NO: 30 or SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the trehalase activity of the mature polypeptide of SEQ ID NO: 30 or SEQ ID NO: 2.

In a particular embodiment the invention relates to polypeptides having a sequence identity to the mature polypeptide of SEQ ID NO: 30 or SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the trehalase activity of the mature polypeptide of SEQ ID NO: 30 or SEQ ID NO: 2.

In a particular embodiment the invention relates to polypeptides having a sequence identity to the mature polypeptide of SEQ ID NO: 30 or SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 95% of the trehalase activity of the mature polypeptide of SEQ ID NO: 30 or SEQ ID NO: 2.

In a particular embodiment the invention relates to polypeptides having a sequence identity to the mature polypeptide of SEQ ID NO: 30 or SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 100% of the trehalase activity of the mature polypeptide of SEQ ID NO: 30 or SEQ ID NO: 2.

In an embodiment, the present invention relates to polypeptides having a sequence identity to the mature polypeptide of SEQ ID NO: 4 of at least 80%, at least 85%, at least 90%, at least 91%, at least 92%, at least 93%, at least 94%, at least 95%, at least 96%, at least 97%, at least 98%, at least 99%, or 100%, which have trehalase activity. In one aspect, the polypeptides differ by up to 10 amino acids, e.g., 1, 2, 3, 4, 5, 6, 7, 8, 9, or 10, from the mature polypeptide of SEQ ID NO: 4.

In a particular embodiment the invention relates to polypeptides having a sequence identity to the mature polypeptide of SEQ ID NO: 4 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the trehalase activity of the mature polypeptide of SEQ ID NO: 4.

In a particular embodiment the invention relates to polypeptides having a sequence identity to the mature polypeptide of SEQ ID NO: 4 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the trehalase activity of the mature polypeptide of SEQ ID NO: 4.

In a particular embodiment the invention relates to polypeptides having a sequence identity to the mature polypeptide of SEQ ID NO: 4 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 80% of the trehalase activity of the mature polypeptide of SEQ ID NO: 4.

In a particular embodiment the invention relates to polypeptides having a sequence identity to the mature polypeptide of SEQ ID NO: 4 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 85% of the trehalase activity of the mature polypeptide of SEQ ID NO: 4.

In a particular embodiment the invention relates to polypeptides having a sequence identity to the mature polypeptide of SEQ ID NO: 4 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the trehalase activity of the mature polypeptide of SEQ ID NO: 4.

In a particular embodiment the invention relates to polypeptides having a sequence identity to the mature polypeptide of SEQ ID NO: 4 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 95% of the trehalase activity of the mature polypeptide of SEQ ID NO: 4.

In a particular embodiment the invention relates to polypeptides having a sequence identity to the mature polypeptide of SEQ ID NO: 4 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 100% of the trehalase activity of the mature polypeptide of SEQ ID NO: 4.

In an embodiment, the polypeptide has been isolated. A polypeptide of the present invention preferably comprises or consists of the amino acid sequence of SEQ ID NO: 30 or SEQ ID NO: 2 or an allelic variant thereof; or is a fragment thereof having trehalase activity. In another aspect, the polypeptide comprises or consists of the mature polypeptide of SEQ ID NO: 30 or SEQ ID NO: 2. In another aspect, the polypeptide comprises or consists of amino acids 21 to 694 of SEQ ID NO: 30 or amino acids 21 to 697 of SEQ ID NO: 2.

In an embodiment, the polypeptide has been isolated. A polypeptide of the present invention preferably comprises or consists of the amino acid sequence of SEQ ID NO: 4 or an allelic variant thereof; or is a fragment thereof having trehalase activity. In another aspect, the polypeptide comprises or consists of the mature polypeptide of SEQ ID NO: 4. In another aspect, the polypeptide comprises or consists of amino acids 21 to 690 of SEQ ID NO: 4.

In another embodiment, the present invention relates to a polypeptide having trehalase activity encoded by a polynucleotide that hybridizes under high stringency conditions or very high stringency conditions with (i) the mature polypeptide coding sequence of SEQ ID NO: 29 or SEQ ID NO: 1, (ii) the cDNA sequence thereof, or (iii) the full-length complement of (i) or (ii) (Sambrook et al., 1989, *Molecular Cloning, A Laboratory Manual*, 2d edition, Cold Spring Harbor, N.Y.). In an embodiment, the polypeptide has been isolated.

In another embodiment, the present invention relates to a polypeptide having trehalase activity encoded by a polynucleotide that hybridizes under high stringency conditions or very high stringency conditions with (i) the mature polypeptide coding sequence of SEQ ID NO: 3, (ii) the cDNA sequence thereof, or (iii) the full-length complement of (i) or (ii) (Sambrook et al., 1989, Molecular Cloning, A Laboratory Manual, 2d edition, Cold Spring Harbor, N.Y.). In an embodiment, the polypeptide has been isolated.

The polynucleotide of SEQ ID NO: 29 or SEQ ID NO: 1 or a subsequence thereof, as well as the polypeptide of SEQ ID NO: 30 or SEQ ID NO: 2 or a fragment thereof may be used to design nucleic acid probes to identify and clone DNA encoding polypeptides having trehalase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

The polynucleotide of SEQ ID NO: 3 or a subsequence thereof, as well as the polypeptide of SEQ ID NO: 4 or a fragment thereof may be used to design nucleic acid probes to identify and clone DNA encoding polypeptides having trehalase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having trehalase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof or SEQ ID NO: 3 or a subsequence thereof, the carrier material is used in a Southern blot.

For purposes of the present invention, hybridization indicates that the polynucleotide hybridizes to a labeled nucleic acid probe corresponding to (i) SEQ ID NO: 29 or SEQ ID NO: 1; (ii) the mature polypeptide coding sequence of SEQ ID NO: 29 or SEQ ID NO: 1; (iii) the cDNA sequence thereof; (iv) the full-length complement thereof; or (v) a subsequence thereof; under high to very high stringency conditions.

For purposes of the present invention, hybridization indicates that the polynucleotide hybridizes to a labeled nucleic acid probe corresponding to (i) SEQ ID NO: 3; (ii) the mature polypeptide coding sequence of SEQ ID NO: 3; (iii) the cDNA sequence thereof; (iv) the full-length complement thereof; or (v) a subsequence thereof; under high to very high stringency conditions.

Molecules to which the nucleic acid probe hybridizes under these conditions can be detected using, for example, X-ray film or any other detection means known in the art.

In another embodiment, the present invention relates to a polypeptide having trehalase activity encoded by a polynucleotide having a sequence identity to the mature polypeptide coding sequence of SEQ ID NO: 29 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to a polypeptide having trehalase activity encoded by a polynucleotide having a sequence identity to the mature polypeptide coding sequence of SEQ ID NO: 1 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to a polypeptide having trehalase activity encoded by a polynucleotide having a sequence identity to the mature polypeptide coding sequence of SEQ ID NO: 3 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to variants of the mature polypeptide of SEQ ID NO: 30 comprising a substitution, deletion, and/or insertion at one or more (e.g., several) positions. In an embodiment, the number of amino acid substitutions, deletions and/or insertions introduced into the mature polypeptide of SEQ ID NO: 30 is up to 10, e.g., 1, 2, 3, 4, 5, 6, 7, 8, 9, or 10.

In another embodiment, the present invention relates to variants of the mature polypeptide of SEQ ID NO: 2 comprising a substitution, deletion, and/or insertion at one or more (e.g., several) positions. In an embodiment, the number of amino acid substitutions, deletions and/or insertions introduced into the mature polypeptide of SEQ ID NO: 2 is up to 10, e.g., 1, 2, 3, 4, 5, 6, 7, 8, 9, or 10.

In another embodiment, the present invention relates to variants of the mature polypeptide of SEQ ID NO: 4 comprising a substitution, deletion, and/or insertion at one or more (e.g., several) positions. In an embodiment, the number of amino acid substitutions, deletions and/or insertions introduced into the mature polypeptide of SEQ ID NO: 4 is up to 10, e.g., 1, 2, 3, 4, 5, 6, 7, 8, 9, or 10.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant molecules are tested for trehalase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Trehalase Activity

A polypeptide having trehalase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In another aspect, the polypeptide is a *Myceliophthora sepedonium* polypeptide having trehalase or a *Chaetomium virescens* polypeptide having trehalase activity.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to polynucleotides encoding a polypeptide of the present invention, as described herein. In an embodiment, the polynucleotide encoding the polypeptide of the present invention has been isolated.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Myceliophthora*, or a related organism or *Chaetomium*, or a related organism and thus, for example, may be an allelic or species variant of the polypeptide encoding region of the polynucleotide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus triose* phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are Bacillus licheniformis or Bacillus subtilis dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoim idazole-succinocarboxamide synthase), adeB (phosphoribosyl-aminoimidazole synthase), amdS (acetamidase), argB (ornithine carbamoyl-transferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an Aspergillus cell are Aspergillus nidulans or Aspergillus oryzae amdS and pyrG genes and a Streptomyces hygroscopicus bar gene. Preferred for use in a Trichoderma cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in E. coli, and pUB110, pE194, pTA1060, and pAMß1 permitting replication in Bacillus.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, Gene 98: 61-67; Cullen et al., 1987, Nucleic Acids Res. 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, Bacillus, Clostridium, Enterococcus, Geobacillus, Lactobacillus, Lactococcus, Oceanobacillus, Staphylococcus, Streptococcus, and Streptomyces. Gram-negative bacteria include, but are not limited to, Campylobacter, E. coli, Flavobacterium, Fusobacterium, Helicobacter, Ilyobacter, Neisseria, Pseudomonas, Salmonella, and Ureaplasma.

The bacterial host cell may be any Bacillus cell including, but not limited to, Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis, and Bacillus thuringiensis cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (*Praha*) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (*Endomycetales*), basidiosporogenous yeast, and yeast belonging to the *Fungi Imperfecti* (*Blastomycetes*). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida*, *Hansenula*, *Kluyveromyces*, *Pichia*, *Saccharomyces*, *Schizosaccharomyces*, or *Yarrowia* cell, such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

For example, the filamentous fungal host cell may be an *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Bjerkandera adusta*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Coprinus cinereus*, *Coriolus hirsutus*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide. In one aspect, the cell is a *Myceliophthora* cell. In another aspect, the cell is a *Myceliophthora sepedonium* cell. In one aspect, the cell is a *Chaetomium* cell. In another aspect, the cell is a *Chaetomium virescens* cell.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered. The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Production in Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn). Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems.

Plant cells and specific plant cell compartments, such as chloroplasts, apoplasts, mitochondria, vacuoles, peroxisomes and cytoplasm are also considered to be a plant part.

Also included within the scope of the present invention are the progeny of such plants, plant parts, and plant cells.

The transgenic plant or plant cell expressing the polypeptide or domain may be constructed in accordance with methods known in the art.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a polypeptide having trehalase activity of the present invention. Preferably, the compositions are enriched in such a polypeptide. The term "enriched" indicates that the trehalase activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

In an embodiment the composition comprises a trehalase of the invention and a glucoamylase. In an embodiment the composition comprises a trehalase of the invention and a glucoamylase derived from *Talaromyces emersonii* (e.g., SEQ ID NO: 13). In an embodiment the composition comprises a trehalase of the invention and a glucoamylase derived from *Gloeophyllum*, such as *G. serpiarium* (e.g., SEQ ID NO: 19) or *G. trabeum* (e.g., SEQ ID NO: 20). In an embodiment the composition comprises a trehalase of the invention, a glucoamylase and an alpha-amylase. In an embodiment the composition comprises a trehalase of the invention, a glucoamylase and an alpha-amylase derived from *Rhizomucor*, preferably a strain the *Rhizomucor pusillus*, such as a *Rhizomucor pusillus* alpha-amylase hybrid having an linker (e.g., from *Aspergillus niger*) and starch-bonding domain (e.g., from *Aspergillus niger*). In an embodiment the composition comprises a trehalase of the invention, a glucoamylase, an alpha-amylase and a cellulolytic enzyme composition. In an embodiment the composition comprises a trehalase of the invention, a glucoamylase, an alpha-amylase and a cellulolytic enzyme composition, wherein the cellulolytic composition is derived from *Trichoderma reesei*. In an embodiment the composition comprises a trehalase of the invention, a glucoamylase, an alpha-amylase and a protease. In an embodiment the composition comprises a trehalase of the invention, a glucoamylase, an alpha-amylase and a protease. The protease may be derived from *Thermoascus aurantiacus*. In an embodiment the composition comprises a trehalase of the invention, a glucoamylase, an alpha-amylase, a cellulolytic enzyme composition and a protease. In an embodiment the composition comprises a trehalase of the invention, a glucoamylase, e.g., derived from *Talaromyces emersonii, Gloeophyllum serpiarium* or *Gloephyllum trabeum*, an alpha-amylase, e.g., derived from *Rhizomucor pusillus*, in particular one having a linker and starch-binding domain, in particular derived from *Aspergillus niger*, in particular one having the following substitutions: G128D+D143N (using SEQ ID NO: 15 for numbering); a cellulolytic enzyme composition derived from *Trichoderma reesei*, and a protease, e.g., derived from *Thermoascus aurantiacus*.

Examples of specifically contemplated secondary enzymes, e.g., a glucoamylase from *Talaromyces emersonii* shown in SEQ ID NO: 13 herein or a glucoamylase having, e.g., at least 60%, at least 70%, at least 80%, at least 90%, at least 95%, at least 96%, at least 97%, at least 98%, at least 99% identity to SEQ ID NO: 13 herein can be found in the "Enzymes" section below.

The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Processes of the Invention

Producing a Fermentation Product from Gelatinized Starch Material Using a Trehalase of the Invention In this aspect the present invention relates to producing a fermentation product, in particular ethanol, from gelatinized and/or ungelatinized starch-containing material or cellulosic material. Fermentable sugars generated during saccharification/hydrolysis are converted to the desired fermentation in question, in particular ethanol, during fermentation by a fermenting organism, in particular yeast.

In an embodiment the invention relates to processes of producing a fermentation product, in particular ethanol, comprising
   (a) liquefying a starch-containing material with an alpha-amylase;
   optionally pre-saccharifying the liquefied material before step (b);
   (b) saccharifying the liquefied material;
   (c) fermenting using a fermentation organism;
   wherein
     i) a glucoamylase;
     ii) a trehalase of the invention;
     iii) optionally a cellulolytic enzyme composition and/or a protease;
are present and/or added during
   saccharification step (b);
   fermentation step (c);
   simultaneous saccharification and fermentation;
   optionally presaccharification step before step (b).

Liquefaction Step (a)

According to processes of the invention, liquefaction in step (a) is carried out by subjecting starch-containing material at a temperature above the initial gelatinization temperature, in particular at a temperature between 80-90° C., to an alpha-amylase and optionally a protease and other enzymes, such as a glucoamylase, a pullulanase and/or a phytase.

The term "initial gelatinization temperature" means the lowest temperature at which gelatinization of the starch-containing material commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material may be determined as the temperature at which birefringence is lost in 5% of the starch granules using the method described by Gorinstein and Lii, 1992, *Starch/Starke* 44(12): 461-466.

According to the invention liquefaction in step (a) is typically carried out at a temperature in the range from 70-100° C. In an embodiment the temperature in liquefaction is between 75-95° C., such as between 75-90° C., preferably between 80-90° C., such as 82-88° C., such as around 85° C.

The pH in liquefaction may be in the range between 3 and 7, preferably from 4 to 6, or more preferably from 4.5 to 5.5.

According to the invention a jet-cooking step may be carried out prior to liquefaction in step (a). The jet-cooking may be carried out at a temperature between 110-145° C., preferably 120-140° C., such as 125-135° C., preferably around 130° C. for about 1-15 minutes, preferably for about 3-10 minutes, especially around about 5 minutes.

In an embodiment, the process of the invention further comprises, prior to the liquefaction step (a), the steps of:

x) reducing the particle size of the starch-containing material, preferably by dry milling;

z) forming a slurry comprising the starch-containing material and water.

According to the invention the dry solid content (DS) in liquefaction lies in the range from 20-55 wt.-%, preferably 25-45 wt.-%, more preferably 30-40 wt.-% or 30-45 wt.-%.

The starch-containing starting material, such as whole grains, may be reduced in particle size, e.g., by milling, in order to open up the structure, to increase surface area, and allowing for further processing. Generally there are two types of processes: wet and dry milling. In dry milling whole kernels are milled and used. Wet milling gives a good separation of germ and meal (starch granules and protein). Wet milling is often applied at locations where the starch hydrolysate is used in production of, e.g., syrups. Both dry milling and wet milling are well known in the art of starch processing. According to the present invention dry milling is preferred.

In an embodiment the particle size is reduced to between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen. In another embodiment at least 50%, preferably at least 70%, more preferably at least 80%, especially at least 90% of the starch-containing material fit through a sieve with #6 screen.

Liquefaction in step (a) may be carried out for 0.5-5 hours, such as 1-3 hours, such as typically around 2 hours.

The alpha-amylase and other optional enzymes, such as protease, may initially be added to the aqueous slurry to initiate liquefaction (thinning). In an embodiment only a portion of the enzymes (e.g., about ⅓) is added to the aqueous slurry, while the rest of the enzymes (e.g., about ⅔) are added in liquefaction step (a).

A non-exhaustive list of examples of alpha-amylases can be found below in the "Alpha-Amylase Present and/or Added In Liquefaction"-section. In a preferred embodiment the alpha-amylase is a bacterial alpha-amylase. Bacterial alpha-amylases are typically thermostable. In a preferred embodiment the alpha-amylase is derived from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 18 herein.

In an embodiment the alpha-amylase used in liquefaction step (a) is a variant of the *Bacillus stearothermophilus* alpha-amylase shown in SEQ ID NO: 18 herein, in particular with the double deletions in I181*+G182*, and optionally with a N193F substitution, and truncated to be around 491 amino acids long, e.g., from 480-495 amino acids long.

Examples of suitable *Bacillus stearothermophilus* alpha-amylase variants can be found below in the "Thermostable Alpha-Amylase"-section and include one from the following group of *Bacillus stearothermophilus* alpha-amylase variants with double deletions I181*+G182*, and optionally substitution N193F, and additionally the following substitutions:

E129V+K177L+R179E;
V59A+Q89R+E129V+K177L+R179E+H208Y+K220P+N224L+Q254S;
V59A+Q89R+E129V+K177L+R179E+Q254S+M284V;
V59A+E129V+K177L+R179E+Q254S+M284V; and
E129V+K177L+R179E+K220P+N224L+S242Q+Q254S
(using SEQ ID NO: 18 for numbering).

According to processes of the invention, liquefaction in step (a) may be carried out using a combination of alpha-amylase (e.g., *Bacillus stearothermophilus* alpha-amylase shown in SEQ ID NO: 18) and protease (e.g., *Pyrococcus furiosus* (pfu protease) shown in SEQ ID NO: 22). A glucoamylase may also be present, such as the one derived from *Penicillium oxalicum* shown in SEQ ID NO: 23 herein (see the "Glucoamylase Present and/or Added In Liquefaction Step (a)"-section below.

Saccharification and Fermentation

A trehalase of the invention, a glucoamylase and optionally a protease and/or a cellulolytic enzyme composition may be present and/or added in saccharification step (b); fermentation step (c); simultaneous saccharification and fermentation (SSF); optionally a presaccharification step before step (b).

In a preferred embodiment the glucoamylase is added together with a fungal alpha-amylase, in particular acid fungal alpha-amylase. Examples of glucoamylases can be found in the "Glucoamylases Present and/or Added In Saccharification and/or Fermentation"-section below.

When doing sequential saccharification and fermentation, saccharification step (b) may be carried out at conditions well-known in the art, i.e., suitable for enzyme saccharification. For instance, the saccharification step (b) may last up to from about 24 to about 72 hours.

In an embodiment pre-saccharification is done before saccharification in step (b). Pre-saccharification is typically done for 40-90 minutes at a temperature between 30-65° C., typically about 60° C. Pre-saccharification is in an embodiment followed by saccharification during fermentation in simultaneous saccharification and fermentation (SSF). Saccharification is typically carried out at temperatures from 20-75° C., preferably from 40-70° C., typically around 60° C., and at a pH between 4 and 5, normally at about pH 4.5.

Simultaneous saccharification and fermentation ("SSF") is widely used in industrial scale fermentation product production processes, especially ethanol production processes. When doing SSF the saccharification step (b) and the fermentation step (c) are carried out simultaneously. There is no holding stage for the saccharification, meaning that a fermenting organism, in particular yeast, and enzymes, may be added together. However, it is also contemplated to add the fermenting organism and enzymes separately. SSF is according to the invention typically carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours. In an embodiment the pH is between 4-5.

In an embodiment of the invention a cellulolytic composition is present and/or added in saccharification step (b), fermentation step (c) or simultaneous saccharification and fermentation (SSF) or pre-saccharification before step (b). Examples of such cellulolytic compositions can be found in the "Cellulolytic Enzyme Composition present and/or added during Saccharification and/or Fermentation"-section below. The optional cellulolytic enzyme composition may be present and/or added together with the glucoamylase and trehalase of the invention. Examples of proteases can be found in the "Proteases Present and/or Added In Saccharification and/or Fermentation"-section below.

In a preferred embodiment the trehalase is present and/or added in an amount between 0.01-20 ug EP trehalase/g DS, such as between 0.05-15 ug EP terhalase/g DS, such as between 0.5 and 10 ug EP trehalase/g DS.

Starch-Containing Materials

According to the invention any suitable starch-containing starting material may be used. The starting material is generally selected based on the desired fermentation product, in particular ethanol. Examples of starch-containing starting materials, suitable for use in processes of the present invention, include cereal, tubers or grains. Specifically the starch-containing material may be corn, wheat, barley, rye, milo, sago, cassava, tapioca, sorghum, oat, rice, peas, beans, or sweet potatoes, or mixtures thereof. Contemplated are also waxy and non-waxy types of corn and barley.

In a preferred embodiment the starch-containing starting material is corn.

In a preferred embodiment the starch-containing starting material is wheat.

In a preferred embodiment the starch-containing starting material is barley.

In a preferred embodiment the starch-containing starting material is rye.

In a preferred embodiment the starch-containing starting material is milo.

In a preferred embodiment the starch-containing starting material is sago.

In a preferred embodiment the starch-containing starting material is cassava.

In a preferred embodiment the starch-containing starting material is tapioca.

In a preferred embodiment the starch-containing starting material is sorghum.

In a preferred embodiment the starch-containing starting material is rice,

In a preferred embodiment the starch-containing starting material is peas.

In a preferred embodiment the starch-containing starting material is beans.

In a preferred embodiment the starch-containing starting material is sweet potatoes.

In a preferred embodiment the starch-containing starting material is oats.

Producing a Fermentation Product from Ungelatinized Starch Material Using a Trehalase of the Invention A trehalase of the invention may suitably be used in a raw starch hydrolysis (RSH) process for producing desired fermentation products, in particular ethanol. In RSH processes the starch does not gelatinize as the process is carried out at temperatures below the initial gelatinization temperature of the starch in question (defined above).

The desired fermentation product may in an embodiment be ethanol produced from ungelatinized (i.e., uncooked), preferably milled, grains, such as corn, or small grains such as wheat, oats, barley, rye, rice, or cereals such as sorghum. Examples of suitable starch-containing starting materials are listed in the section "Starch-Containing Materials"-section above.

Accordingly, in this aspect the invention relates to processes of producing fermentation products from starch-containing material comprising:

(a) saccharifying a starch-containing material at a temperature below the initial gelatinization temperature; and (b) fermenting using a fermentation organism; and (c) optionally recovering the fermentation product;

wherein saccharification and/or fermentation is done in the presence of the following enzymes: glucoamylase, alpha-amylase, trehalase of the invention, and optionally a cellulolytic enzyme composition and/or a protease.

Before step (a) an aqueous slurry of starch-containing material, such as granular starch, having 10-55 wt.-% dry solids (DS), preferably 25-45 wt.-% dry solids, more preferably 30-40% dry solids of starch-containing material may be prepared. The slurry may include water and/or process waters, such as stillage (backset), scrubber water, evaporator condensate or distillate, side-stripper water from distillation, or process water from other fermentation product plants.

Because a raw starch hydrolysis process of the invention is carried out below the initial gelatinization temperature, and thus no significant viscosity increase takes place, high levels of stillage may be used, if desired. In an embodiment the aqueous slurry contains from about 1 to about 70 vol.-%, preferably 15-60% vol.-%, especially from about 30 to 50 vol.-% water and/or process waters, such as stillage (backset), scrubber water, evaporator condensate or distillate, side-stripper water from distillation, or process water from other fermentation product plants, or combinations thereof, or the like.

In an embodiment backset, or another recycled stream, is added to the slurry before step (a), or to the saccharification (step (a)), or to the simultaneous saccharification and fermentation steps (combined step (a) and step (b)).

A RSH process of the invention is conducted at a temperature below the initial gelatinization temperature, which means that the temperature at which a separate step (a) is carried out typically lies in the range between 25-75° C., such as between 30-70° C., or between 45-60° C.

In a preferred embodiment the temperature during fermentation in step (b) or simultaneous saccharification and fermentation in steps (a) and (b) is between 25° C. and 40°

C., preferably between 28° C. and 36° C., such as between 28° C. and 35° C., such as between 28° C. and 34° C., such as around 32° C.

In an embodiment of the invention fermentation is carried out for 30 to 150 hours, preferably 48 to 96 hours. 66.

In an embodiment fermentation is carried out so that the sugar level, such as glucose level, is kept at a low level, such as below 6 wt.-%, such as below about 3 wt.-%, such as below about 2 wt.-%, such as below about 1 wt.-%, such as below about 0.5%, or below 0.25% wt.-%, such as below about 0.1 wt.-%. Such low levels of sugar can be accomplished by simply employing adjusted quantities of enzymes and fermenting organism. A skilled person in the art can easily determine which doses/quantities of enzyme and fermenting organism to use. The employed quantities of enzyme and fermenting organism may also be selected to maintain low concentrations of maltose in the fermentation broth. For instance, the maltose level may be kept below about 0.5 wt.-%, such as below about 0.2 wt.-%.

The process of the invention may be carried out at a pH from 3 and 7, preferably from 3 to 6, or more preferably from 3.5 to 5.0.

The term "granular starch" means raw uncooked starch, i.e., starch in its natural form found in, e.g., cereal, tubers or grains. Starch is formed within plant cells as tiny granules insoluble in water. When put in cold water, the starch granules may absorb a small amount of the liquid and swell. At temperatures up to around 50° C. to 75° C. the swelling may be reversible. However, at higher temperatures an irreversible swelling called "gelatinization" begins. The granular starch may be a highly refined starch, preferably at least 90%, at least 95%, at least 97% or at least 99.5% pure, or it may be a more crude starch-containing materials comprising (e.g., milled) whole grains including non-starch fractions such as germ residues and fibers.

The raw material, such as whole grains, may be reduced in particle size, e.g., by milling, in order to open up the structure and allowing for further processing. Examples of suitable particle sizes are disclosed in U.S. Pat. No. 4,514,496 and WO2004/081193 (both references are incorporated by reference). Two processes are preferred according to the invention: wet and dry milling. In dry milling whole kernels are milled and used. Wet milling gives a good separation of germ and meal (starch granules and protein) and is often applied at locations where the starch hydrolysate is used in production of, e.g., syrups. Both dry and wet milling is well known in the art of starch processing.

In an embodiment the particle size is reduced to between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen. In a preferred embodiment starch-containing material is prepared by reducing the particle size of the starch-containing material, preferably by milling, such that at least 50% of the starch-containing material has a particle size of 0.1-0.5 mm.

In a preferred embodiment the trehalase is present and/or added in an amount between 0.01-20 ug EP trehalase/g DS, such as between 0.05-15 ug EP terhalase/g DS, such as between 0.5 and 10 ug EP trehalase/g DS.

According to the invention the enzymes are added so that the glucoamylase is present in an amount of 0.001 to 10 AGU/g DS, preferably from 0.01 to 5 AGU/g DS, especially 0.1 to 0.5 AGU/g DS.

According to the invention the enzymes are added so that the alpha-amylase is present or added in an amount of 0.001 to 10 AFAU/g DS, preferably from 0.01 to 5 AFAU/g DS, especially 0.3 to 2 AFAU/g DS or 0.001 to 1 FAU-F/g DS, preferably 0.01 to 1 FAU-F/g DS.

According to the invention the enzymes are added so that the cellulolytic enzyme composition is present or added in an amount 1-10,000 micro grams EP/g DS, such as 2-5,000, such as 3 and 1,000, such as 4 and 500 micro grams EP/g DS.

According to the invention the enzymes are added so that the cellulolytic enzyme composition is present or added in an amount in the range from 0.1-100 FPU per gram total solids (TS), preferably 0.5-50 FPU per gram TS, especially 1-20 FPU per gram TS.

In an embodiment of the invention the enzymes are added so that the protease is present in an amount of 0.0001-1 mg enzyme protein per g DS, preferably 0.001 to 0.1 mg enzyme protein per g DS. Alternatively, the protease is present and/or added in an amount of 0.0001 to 1 LAPU/g DS, preferably 0.001 to 0.1 LAPU/g DS and/or 0.0001 to 1 mAU-RH/g DS, preferably 0.001 to 0.1 mAU-RH/g DS.

In an embodiment of the invention the enzymes are added so that the protease is present or added in an amount in the range 1-1,000 μg EP/g DS, such as 2-500 μg EP/g DS, such as 3-250 μg EP/g DS.

In a preferred embodiment ratio between glucoamylase and alpha-amylase is between 99:1 and 1:2, such as between 98:2 and 1:1, such as between 97:3 and 2:1, such as between 96:4 and 3:1, such as 97:3, 96:4, 95:5, 94:6, 93:7, 90:10, 85:15, 83:17 or 65:35 (mg EP glucoamylase: mg EP alpha-amylase).

In a preferred embodiment the total dose of glucoamylase and alpha-amylase is according to the invention from 10-1,000 μg/g DS, such as from 50-500 μg/g DS, such as 75-250 μg/g DS.

In a preferred embodiment the total dose of cellulolytic enzyme composition added is from 10-500 μg/g DS, such as from 20-400 μg/g DS, such as 20-300 μg/g DS.

In an embodiment the glucoamylase, such as one derived from *Trametes cingulata*, used in fermentation or SSF exhibits at least 60%, such as at least 70%, at least 75%, at least 80%, at least 85%, at least 90%, at least 95%, at least 96%, at least 97%, at least 98%, at least 99% or even 100% identity to the mature part of SEQ ID NO: 14.

In an embodiment the glucoamylase, such as one derived from *Pycnoporus sanguineus*, used in fermentation or SSF exhibits at least 60%, such as at least 70%, at least 75%, at least 80%, at least 85%, at least 90%, at least 95%, at least 96%, at least 97%, at least 98%, at least 99% or even 100% identity to the mature part of SEQ ID NO: 28.

In an embodiment the alpha-amylase used in fermentation or SSF exhibits at least 60%, such as at least 70%, at least 75%, at least 80%, at least 85%, at least 90%, at least 95%, at least 96%, at least 97%, at least 98%, at least 99% or even 100% identity to the mature part of SEQ ID NO: 15.

In a preferred embodiment the invention relates to processes of producing fermentation products from starch-containing material comprising:
  (a) saccharifying a starch-containing material at a temperature below the initial gelatinization temperature; and
  (b) fermenting using a fermentation organism;
wherein saccharification and/or fermentation is done in the presence of the following enzymes:
  i) glucoamylase;
  ii) alpha-amylase;
  iii) trehalse of the invention;
  iii) optionally a cellulolytic enzyme composition and/or a protease.

In a preferred embodiment the enzymes may be added as an enzyme composition of the invention. In a preferred embodiment steps (a) and (b) are carried out simultaneously (i.e., one-step fermentation). However, step (a) and (b) may also be carried our sequentially.

Fermentation

Fermentation is carried out in a fermentation medium. The fermentation medium includes the fermentation substrate, that is, the carbohydrate source that is metabolized by the fermenting organism. According to the invention the fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Fermenting Organisms for Starch Based Fermentation

The term "fermenting organism" refers to any organism, including bacterial and fungal organisms, especially yeast, suitable for use in a fermentation process and capable of producing the desired fermentation product. Especially suitable fermenting organisms are able to ferment, i.e., convert, sugars, such as glucose or maltose, directly or indirectly into the desired fermentation product, such as in particular ethanol. Examples of fermenting organisms include fungal organisms, such as in particular yeast. Preferred yeast includes strains of *Saccharomyces* spp., in particular, *Saccharomyces cerevisiae*.

Suitable concentrations of the viable fermenting organism during fermentation, such as SSF, are well known in the art or can easily be determined by the skilled person in the art. In one embodiment the fermenting organism, such as ethanol fermenting yeast, (e.g., *Saccharomyces cerevisiae*) is added to the fermentation medium so that the viable fermenting organism, such as yeast, count per mL of fermentation medium is in the range from $10^5$ to $10^{12}$, preferably from $10^7$ to $10^{10}$, especially about $5 \times 10^7$.

Examples of commercially available yeast includes, e.g., RED START™ and ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

Recovery

Subsequent to fermentation, e.g., SSF, the fermentation product, in particular ethanol may be separated from the fermentation medium. The slurry may be distilled to recover/extract the desired fermentation product (i.e., ethanol). Alternatively the desired fermentation product (i.e., ethanol) may be extracted from the fermentation medium by micro or membrane filtration techniques. The fermentation product (i.e., ethanol) may also be recovered by stripping or other method well known in the art.

Alpha-Amylase Present and/or Added in Liquefaction

According to the invention an alpha-amylase is present and/or added in liquefaction optionally together with other enzymes such as a protease, a glucoamylase, phytase and/or pullulanase.

The alpha-amylase added in liquefaction step (a) may be any alpha-amylase. Preferred are bacterial alpha-amylases, which typically are stable at temperatures used in liquefaction.

Bacterial Alpha-Amylase

The term "bacterial alpha-amylase" means any bacterial alpha-amylase classified under EC 3.2.1.1. A bacterial alpha-amylase used according to the invention may, e.g., be derived from a strain of the genus *Bacillus*, which is sometimes also referred to as the genus *Geobacillus*. In an embodiment the *Bacillus* alpha-amylase is derived from a strain of *Bacillus amyloliquefaciens*, *Bacillus licheniformis*, *Bacillus stearothermophilus*, or *Bacillus subtilis*, but may also be derived from other *Bacillus* sp.

Specific examples of bacterial alpha-amylases include the *Bacillus stearothermophilus* alpha-amylase of SEQ ID NO: 3 in WO 99/19467 or SEQ ID NO: 18 herein, the *Bacillus amyloliquefaciens* alpha-amylase of SEQ ID NO: 5 in WO 99/19467, and the *Bacillus licheniformis* alpha-amylase of SEQ ID NO: 4 in WO 99/19467 (all sequences are hereby incorporated by reference). In an embodiment the alpha-amylase may be an enzyme having a degree of identity of at least 60%, e.g., at least 70%, at least 80%, at least 90%, at least 95%, at least 96%, at least 97%, at least 98% or at least 99% to any of the sequences shown in SEQ ID NOS: 3, 4 or 5, respectively, in WO 99/19467.

In an embodiment the alpha-amylase may be an enzyme having a degree of identity of at least 60%, e.g., at least 70%, at least 80%, at least 90%, at least 91%, at least 92%, at least 93%, at least 94%, at least 95%, at least 96%, at least 97%, at least 98% or at least 99% to any of the sequences shown in SEQ ID NO: 3 in WO 99/19467 or SEQ ID NO: 18 herein.

In a preferred embodiment the alpha-amylase is derived from *Bacillus stearothermophilus*. The *Bacillus stearothermophilus* alpha-amylase may be a mature wild-type or a mature variant thereof. The mature *Bacillus stearothermophilus* alpha-amylases may naturally be truncated during recombinant production. For instance, the *Bacillus stearothermophilus* alpha-amylase may be a truncated so it has around 491 amino acids, e.g., so that it is between 480-495 amino acids long, so it lacks a functional starch binding domain (compared to SEQ ID NO: 3 in WO 99/19467) or SEQ ID NO: 18 herein.

The *Bacillus* alpha-amylase may also be a variant and/or hybrid. Examples of such a variant can be found in any of WO 96/23873, WO 96/23874, WO 97/41213, WO 99/19467, WO 00/60059, and WO 02/10355 (all documents are hereby incorporated by reference). Specific alpha-amylase variants are disclosed in U.S. Pat. Nos. 6,093,562, 6,187,576, 6,297,038, and 7,713,723 (hereby incorporated by reference) and include *Bacillus stearothermophilus* alpha-amylase (often referred to as BSG alpha-amylase) variants having a deletion of one or two amino acids at positions R179, G180, 1181 and/or G182, preferably a double deletion disclosed in WO 96/23873—see, e.g., page 20, lines 1-10 (hereby incorporated by reference), preferably corresponding to deletion of positions 1181 and G182 compared to the amino acid sequence of *Bacillus stearothermophilus* alpha-amylase set forth in SEQ ID NO: 3 disclosed in WO 99/19467 or SEQ ID NO: 1 herein or the deletion of amino acids R179 and G180 using SEQ ID NO: 3 in WO 99/19467 or SEQ ID NO: 1 herein for numbering (which reference is hereby incorporated by reference). Even more preferred are *Bacillus* alpha-amylases, especially *Bacillus stearothermophilus* alpha-amylases, which have a double deletion corresponding to a deletion of positions 181 and 182 and further comprise a N193F substitution (also denoted I181*+G182*+N193F) compared to the wild-type BSG alpha-amylase amino acid sequence set forth in SEQ ID NO: 3 disclosed in WO 99/19467 or SEQ ID NO: 18 herein. The bacterial alpha-amylase may also have a substitution in a position corresponding to S239 in the *Bacillus licheniformis* alpha-amylase shown in SEQ ID NO: 4 in WO 99/19467, or a S242 and/or E188P variant of the *Bacillus stearothermophilus* alpha-amylase of SEQ ID NO: 3 in WO 99/19467 or SEQ ID NO: 18 herein.

In an embodiment the variant is a S242A, E or Q variant, preferably a S242Q variant, of the *Bacillus stearothermophilus* alpha-amylase (using SEQ ID NO: 18 herein for numbering).

In an embodiment the variant is a position E188 variant, preferably E188P variant of the *Bacillus stearothermophilus* alpha-amylase (using SEQ ID NO: 18 herein for numbering).

The bacterial alpha-amylase may in an embodiment be a truncated *Bacillus* alpha-amylase. Especially the truncation is so that, e.g., the *Bacillus stearothermophilus* alpha-amylase shown in SEQ ID NO: 3 in WO 99/19467 or SEQ ID NO: 18 herein, is around 491 amino acids long, such as from 480 to 495 amino acids long, or so it lack a functional starch binding domain.

Bacterial Hybrid Alpha-Amylases

The bacterial alpha-amylase may also be a hybrid bacterial alpha-amylase, e.g., an alpha-amylase comprising 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467). In a preferred embodiment this hybrid has one or more, especially all, of the following substitutions:

G48A+T49I+G107A+H156Y+A181T+N190F+I201F+A209V+Q264S (using the *Bacillus licheniformis* numbering in SEQ ID NO: 4 of WO 99/19467). Also preferred are variants having one or more of the following mutations (or corresponding mutations in other *Bacillus* alpha-amylases): H154Y, A181T, N190F, A209V and Q264S and/or the deletion of two residues between positions 176 and 179, preferably the deletion of E178 and G179 (using SEQ ID NO: 5 of WO 99/19467 for position numbering).

In an embodiment the bacterial alpha-amylase is the mature part of the chimeric alpha-amylase disclosed in Richardson et al. (2002), The Journal of Biological Chemistry, Vol. 277, No 29, Issue 19 July, pp. 267501-26507, referred to as BD5088 or a variant thereof. This alpha-amylase is the same as the one shown in SEQ ID NO: 2 in WO 2007134207. The mature enzyme sequence starts after the initial "Met" amino acid in position 1.

Thermostable Alpha-Amylase

The alpha-amylase may be a thermostable alpha-amylase, such as a thermostable bacterial alpha-amylase, preferably from *Bacillus stearothermophilus*.

In an embodiment of the invention the alpha-amylase is an bacterial alpha-amylase, preferably derived from the genus *Bacillus*, especially a strain of *Bacillus stearothermophilus*, in particular the *Bacillus stearothermophilus* as disclosed in WO 99/019467 as SEQ ID NO: 3 (SEQ ID NO: 18 herein) with one or two amino acids deleted at positions R179, G180, I181 and/or G182, in particular with R179 and G180 deleted, or with I181 and G182 deleted, with mutations in below list of mutations.

In preferred embodiments the *Bacillus stearothermophilus* alpha-amylases have double deletion I181+G182, and optionally substitution N193F, further comprising mutations selected from below list:

V59A+Q89R+G112D+E129V+K177L+R179E+K220P+N224L+Q254S;
V59A+Q89R+E129V+K177L+R179E+H208Y+K220P+N224L+Q254S;
V59A+Q89R+E129V+K177L+R179E+K220P+N224L+Q254S+D269E+D281N;
V59A+Q89R+E129V+K177L+R179E+K220P+N224L+Q254S+I270L;
V59A+Q89R+E129V+K177L+R179E+K220P+N224L+Q254S+H274K;
V59A+Q89R+E129V+K177L+R179E+K220P+N224L+Q254S+Y276F;
V59A+E129V+R157Y+K177L+R179E+K220P+N224L+S242Q+Q254S;
V59A+E129V+K177L+R179E+H208Y+K220P+N224L+S242Q+Q254S;
59A+E129V+K177L+R179E+K220P+N224L+S242Q+Q254S;
V59A+E129V+K177L+R179E+K220P+N224L+S242Q+Q254S+H274K;
V59A+E129V+K177L+R179E+K220P+N224L+S242Q+Q254S+Y276F;
V59A+E129V+K177L+R179E+K220P+N224L+S242Q+Q254S+D281N;
V59A+E129V+K177L+R179E+K220P+N224L+S242Q+Q254S+M284T;
V59A+E129V+K177L+R179E+K220P+N224L+S242Q+Q254S+G416V;
V59A+E129V+K177L+R179E+K220P+N224L+Q254S;
V59A+E129V+K177L+R179E+K220P+N224L+Q254S+M284T;
A91 L+M961+E129V+K177L+R179E+K220P+N224L+S242Q+Q254S;
E129V+K177L+R179E;
E129V+K177L+R179E+K220P+N224L+S242Q+Q254S;
E129V+K177L+R179E+K220P+N224L+S242Q+Q254S+Y276F+L427M;
E129V+K177L+R179E+K220P+N224L+S242Q+Q254S+M284T;
E129V+K177L+R179E+K220P+N224L+S242Q+Q254S+N376*+I377*;
E129V+K177L+R179E+K220P+N224L+Q254S;
E129V+K177L+R179E+K220P+N224L+Q254S+M284T;
E129V+K177L+R179E+S242Q;
E129V+K177L+R179V+K220P+N224L+S242Q+Q254S;
K220P+N224L+S242Q+Q254S;
M284V;
V59A+Q89R+E129V+K177L+R179E+Q254S+M284V.
V59A+E129V+K177L+R179E+Q254S+M284V;

Specific information about the thermostability of above alpha-amylases variants can be found in WO12/088303 (Novozymes) which is hereby incorporated by reference.

In a preferred embodiment the alpha-amylase is selected from the group of *Bacillus stearothermophilus* alpha-amylase variants having a double deletion in I181+G182, and optionally a substitution in N193F, and substitutions from the following list E129V+K177L+R179E;
V59A+Q89R+E129V+K177L+R179E+H208Y+K220P+N224L+Q254S;
V59A+Q89R+E129V+K177L+R179E+Q254S+M284V;
V59A+E129V+K177L+R179E+Q254S+M284V; and
E129V+K177L+R179E+K220P+N224L+S242Q+Q254S
(using SEQ ID NO: 18 herein for numbering).

It should be understood that when referring to *Bacillus stearothermophilus* alpha-amylase and variants thereof they are normally produced in truncated form. In particular, the truncation may be so that the *Bacillus stearothermophilus* alpha-amylase shown in SEQ ID NO: 3 in WO 99/19467 or SEQ ID NO: 18 herein, or variants thereof, are truncated in the C-terminal and are typically around 491 amino acids long, such as from 480-495 amino acids long, or so that it lacks a functional starch binding domain.

In a preferred embodiment the alpha-amylase variant may be an enzyme having a degree of identity of at least 60%, e.g., at least 70%, at least 80%, at least 90%, at least 95%, at least 91%, at least 92%, at least 93%, at least 94%, at least 95%, at least 96%, at least 97%, at least 98% or at least 99%, but less than 100% to the sequence shown in SEQ ID NO: 3 in WO 99/19467 or SEQ ID NO: 18 herein.

In an embodiment the bacterial alpha-amylase, e.g., Bacillus alpha-amylase, such as especially Bacillus stearothermophilus alpha-amylase, or variant thereof, is dosed to liquefaction in a concentration between 0.01-10 KNU-A/g DS, e.g., between 0.02 and 5 KNU-A/g DS, such as 0.03 and 3 KNU-A, preferably 0.04 and 2 KNU-A/g DS, such as especially 0.01 and 2 KNU-A/g DS. In an embodiment the bacterial alpha-amylase, e.g., Bacillus alpha-amylase, such as especially Bacillus stearothermophilus alpha-amylases, or variant thereof, is dosed to liquefaction in a concentration of between 0.0001-1 mg EP (Enzyme Protein)/g DS, e.g., 0.0005-0.5 mg EP/g DS, such as 0.001-0.1 mg EP/g DS.

Protease Present and/or Added in Liquefaction

According to the invention a protease may optionally be present and/or added in liquefaction together with the alpha-amylase, and an optional glucoamylase, phytase and/or pullulanase.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In a preferred embodiment the thermostable protease used according to the invention is a "metallo protease" defined as a protease belonging to EC 3.4.24 (metalloendopeptidases); preferably EC 3.4.24.39 (acid metallo proteinases).

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

Examples of protease substrates are casein, such as Azurine-Crosslinked Casein (AZCL-casein). Two protease assays are described below in the "Materials & Methods"-section, of which the so-called "AZCL-Casein Assay" is the preferred assay.

There are no limitations on the origin of the protease used in a process of the invention as long as it fulfills the thermostability properties defined below.

In one embodiment the protease is of fungal origin.

The protease may be a variant of, e.g., a wild-type protease as long as the protease is thermostable. In a preferred embodiment the thermostable protease is a variant of a metallo protease as defined above. In an embodiment the thermostable protease used in a process of the invention is of fungal origin, such as a fungal metallo protease, such as a fungal metallo protease derived from a strain of the genus Thermoascus, preferably a strain of Thermoascus aurantiacus, especially Thermoascus aurantiacus CGMCC No. 0670 (classified as EC 3.4.24.39).

In an embodiment the thermostable protease is a variant of the mature part of the metallo protease shown in SEQ ID NO: 2 disclosed in WO 2003/048353 or the mature part of SEQ ID NO: 1 in WO 2010/008841 and shown as SEQ ID NO: 17 herein, further with mutations selected from below list:

S5*+D79L+S87P+A112P+D142L;
D79L+S87P+A112P+T124V+D142L;
S5*+N26R+D79L+S87P+A112P+D142L;
N26R+T46R+D79L+S87P+A112P+D142L;
T46R+D79L+S87P+T116V+D142L;
D79L+P81R+S87P+A112P+D142L;
A27K+D79L+S87P+A112P+T124V+D142L;
D79L+Y82F+S87P+A112P+T124V+D142L;
D79L+S87P+A112P+T124V+A126V+D142L;
D79L+S87P+A112P+D142L;
D79L+Y82F+S87P+A112P+D142L;
S38T+D79L+S87P+A112P+A126V+D142L;
D79L+Y82F+S87P+A112P+A126V+D142L;
A27K+D79L+S87P+A112P+A126V+D142L;
D79L+S87P+N98C+A112P+G135C+D142L;
D79L+S87P+A112P+D142L+T141C+M161C;
S36P+D79L+S87P+A112P+D142L;
A37P+D79L+S87P+A112P+D142L;
S49P+D79L+S87P+A112P+D142L;
S50P+D79L+S87P+A112P+D142L;
D79L+S87P+D104P+A112P+D142L;
D79L+Y82F+S87G+A112P+D142L;
S70V+D79L+Y82F+S87G+Y97W+A112P+D142L;
D79L+Y82F+S87G+Y97W+D104P+A112P+D142L;
S70V+D79L+Y82F+S87G+A112P+D142L;
D79L+Y82F+S87G+D104P+A112P+D142L;
D79L+Y82F+S87G+A112P+A126V+D142L;
Y82F+S87G+S70V+D79L+D104P+A112P+D142L;
Y82F+S87G+D79L+D104P+A112P+A126V+D142L;
A27K+D79L+Y82F+S87G+D104P+A112P+A126V+D142L;
A27K+Y82F+S87G+D104P+A112P+A126V+D142L;
A27K+D79L+Y82F+D104P+A112P+A126V+D142L;
A27K+Y82F+D104P+A112P+A126V+D142L;
A27K+D79L+S87P+A112P+D142L;
D79L+S87P+D142L.

Specific information about the thermostability of above protease variants can be found in WO12/088303 (Novozymes), which is hereby incorporated by reference.

In an preferred embodiment the thermostable protease is a variant of the metallo protease disclosed as the mature part of SEQ ID NO: 2 disclosed in WO 2003/048353 or the mature part of SEQ ID NO: 1 in WO 2010/008841 or SEQ ID NO: 17 herein with the following mutations:

D79L+S87P+A112P+D142L;
D79L+S87P+D142L; or
A27K+D79L+Y82F+S87G+D104P+A112P+A126V+D142L.

In an embodiment the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 17 herein.

The thermostable protease may also be derived from any bacterium as long as the protease has the thermostability properties defined according to the invention.

In an embodiment the thermostable protease is derived from a strain of the bacterium *Pyrococcus*, such as a strain of *Pyrococcus furiosus* (pfu protease).

In an embodiment the protease is one shown as SEQ ID NO: 1 in U.S. Pat. No. 6,358,726-B1 (Takara Shuzo Company), or SEQ ID NO: 22 herein.

In another embodiment the thermostable protease is one disclosed in SEQ ID NO: 22 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 22 herein. *Pyroccus furiosus* protease can be purchased from Takara Bio, Japan.

Glucoamylase Present and/or Added in Liquefaction

According to the invention a glucoamylase may optionally be present and/or added in liquefaction step (a). In a preferred embodiment the glucoamylase is added together with or separately from the alpha-amylase and optional protease, phytase and/or pullulanase.

In a specific and preferred embodiment the glucoamylase, preferably of fungal origin, preferably a filamentous fungi, is from a strain of the genus *Penicillium*, especially a strain of *Penicillium oxalicum*, in particular the *Penicillium oxalicum* glucoamylase disclosed as SEQ ID NO: 2 in WO 2011/127802 (which is hereby incorporated by reference) and shown in SEQ ID NO: 23 herein.

In an embodiment the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NO: 23 herein.

In a preferred embodiment the glucoamylase is a variant of the *Penicillium oxalicum* glucoamylase disclosed as SEQ ID NO: 2 in WO 2011/127802 and shown in SEQ ID NO: 23 herein, having a K79V substitution (using the mature sequence shown in SEQ ID NO: 23 herein for numbering). The K79V glucoamylase variant has reduced sensitivity to protease degradation relative to the parent as disclosed in WO 2013/036526 (which is hereby incorporated by reference).

In an embodiment the glucoamylase is derived from *Penicillium oxalicum*.

In an embodiment the glucoamylase is a variant of the *Penicillium oxalicum* glucoamylase disclosed as SEQ ID NO: 2 in WO 2011/127802 and shown in SEQ ID NO: 23 herein. In a preferred embodiment the *Penicillium oxalicum* glucoamylase is the one disclosed as SEQ ID NO: 2 in WO 2011/127802 and shown in SEQ ID NO: 23 herein having Val (V) in position 79 (using SEQ ID NO: 23 herein for numbering).

Contemplated *Penicillium oxalicum* glucoamylase variants are disclosed in WO 2013/053801 which is hereby incorporated by reference.

In an embodiment these variants have reduced sensitivity to protease degradation. degradation.

In an embodiment these variant have improved thermostability compared to the parent.

More specifically, in an embodiment the glucoamylase has a K79V substitution (using SEQ ID NO: 23 herein for numbering), (PE001 variant), and further comprises at least one of the following substitutions or combination of substitutions:

T65A; or
Q327F; or
E501V; or
Y504T; or
Y504*; or
T65A+Q327F; or
T65A+E501V; or
T65A+Y504T; or
T65A+Y504*; or
Q327F+E501V; or
Q327F+Y504T; or
Q327F+Y504*; or
E501V+Y504T; or
E501V+Y504*; or
T65A+Q327F+E501V; or
T65A+Q327F+Y504T; or
T65A+E501V+Y504T; or
Q327F+E501V+Y504T; or
T65A+Q327F+Y504*; or
T65A+E501V+Y504*; or
Q327F+E501V+Y504*; or
T65A+Q327F+E501V+Y504T; or
T65A+Q327F+E501V+Y504*;
E501V+Y504T; or
T65A+K161S; or
T65A+Q405T; or
T65A+Q327W; or
T65A+Q327F; or
T65A+Q327Y; or
P11F+T65A+Q327F; or
R1K+D3W+K5Q+G7V+N8S+T10K+P11S+T65A+Q327F; or
P2N+P4S+P11F+T65A+Q327F; or
P11F+D26C+K330+T65A+Q327F; or
P2N+P4S+P11F+T65A+Q327W+E501V+Y504T; or
R1E+D3N+P4G+G6R+G7A+N8A+T10D+P11D+T65A+Q327F; or
P11F+T65A+Q327W; or
P2N+P4S+P11F+T65A+Q327F+E501V+Y504T; or
P11F+T65A+Q327W+E501V+Y504T; or
T65A+Q327F+E501V+Y504T; or
T65A+S105P+Q327W; or
T65A+S105P+Q327F; or
T65A+Q327W+S364P; or
T65A+Q327F+S364P; or
T65A+S103N+Q327F; or
P2N+P4S+P11F+K34Y+T65A+Q327F; or
P2N+P4S+P11F+T65A+Q327F+D445N+V447S; or
P2N+P4S+P11F+T65A+I172V+Q327F; or
P2N+P4S+P11F+T65A+Q327F+N502*; or
P2N+P4S+P11F+T65A+Q327F+N502T+P563S+K571E; or
P2N+P4S+P11F+R31S+K33V+T65A+Q327F+N564D+K571S; or
P2N+P4S+P11F+T65A+Q327F+S377T; or
P2N+P4S+P11F+T65A+V325T+Q327W; or
P2N+P4S+P11F+T65A+Q327F+D445N+V447S+E501V+Y504T; or
P2N+P4S+P11F+T65A+I172V+Q327F+E501V+Y504T; or
P2N+P4S+P11F+T65A+Q327F+S377T+E501V+Y504T; or

P2N+P4S+P11F+D26N+K34Y+T65A+Q327F; or
P2N+P4S+P11F+T65A+Q327F+I375A+E501V+Y504T; or
P2N+P4S+P11F+T65A+K218A+K221D+Q327F+E501V+Y504T; or
P2N+P4S+P11F+T65A+S103N+Q327F+E501V+Y504T; or
P2N+P4S+T10D+T65A+Q327F+E501V+Y504T; or
P2N+P4S+F12Y+T65A+Q327F+E501V+Y504T; or
K5A+P11F+T65A+Q327F+E501V+Y504T; or
P2N+P4S+T10E+E18N+T65A+Q327F+E501V+Y504T; or
P2N+T10E+E18N+T65A+Q327F+E501V+Y504T; or
P2N+P4S+P11F+T65A+Q327F+E501V+Y504T+T568N; or
P2N+P4S+P11F+T65A+Q327F+E501V+Y504T+K524T+G526A; or
P2N+P4S+P11F+K34Y+T65A+Q327F+D445N+V447S+E501V+Y504T; or
P2N+P4S+P11F+R31S+K33V+T65A+Q327F+D445N+V447S+E501V+Y504T; or
P2N+P4S+P11F+D26N+K34Y+T65A+Q327F+E501V+Y504T; or
P2N+P4S+P11F+T65A+F80*+Q327F+E501V+Y504T; or
P2N+P4S+P11F+T65A+K112S+Q327F+E501V+Y504T; or
P2N+P4S+P11F+T65A+Q327F+E501V+Y504T+T516P+K524T+G526A; or
P2N+P4S+P11F+T65A+Q327F+E501V+N502T+Y504*; or
P2N+P4S+P11F+T65A+Q327F+E501V+Y504T; or
P2N+P4S+P11F+T65A+S103N+Q327F+E501V+Y504T; or
K5A+P11F+T65A+Q327F+E501V+Y504T; or
P2N+P4S+P11F+T65A+Q327F+E501V+Y504T+T516P+K524T+G526A; or
P2N+P4S+P11F+T65A+V79A+Q327F+E501V+Y504T; or
P2N+P4S+P11F+T65A+V79G+Q327F+E501V+Y504T; or
P2N+P4S+P11F+T65A+V79I+Q327F+E501V+Y504T; or
P2N+P4S+P11F+T65A+V79L+Q327F+E501V+Y504T; or
P2N+P4S+P11F+T65A+V79S+Q327F+E501V+Y504T; or
P2N+P4S+P11F+T65A+L72V+Q327F+E501V+Y504T; or
S255N+Q327F+E501V+Y504T; or
P2N+P4S+P11F+T65A+E74N+V79K+Q327F+E501V+Y504T; or
P2N+P4S+P11F+T65A+G220N+Q327F+E501V+Y504T; or
P2N+P4S+P11F+T65A+Y245N+Q327F+E501V+Y504T; or
P2N+P4S+P11F+T65A+Q253N+Q327F+E501V+Y504T; or
P2N+P4S+P11F+T65A+D279N+Q327F+E501V+Y504T; or
P2N+P4S+P11F+T65A+Q327F+S359N+E501V+Y504T; or
P2N+P4S+P11F+T65A+Q327F+D370N+E501V+Y504T; or
P2N+P4S+P11F+T65A+Q327F+V460S+E501V+Y504T; or
P2N+P4S+P11F+T65A+Q327F+V460T+P468T+E501V+Y504T; or
P2N+P4S+P11F+T65A+Q327F+T463N+E501V+Y504T; or
P2N+P4S+P11F+T65A+Q327F+S465N+E501V+Y504T; or
P2N+P4S+P11F+T65A+Q327F+T477N+E501V+Y504T.

In a preferred embodiment the *Penicillium oxalicum* glucoamylase variant has a K79V substitution (using SEQ ID NO: 23 herein for numbering), corresponding to the PE001 variant, and further comprises one of the following mutations:
P11F+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
P2N+P4S+P11F+T65A+Q327F+E501V+Y504T; or
P11F+T65A+Q327W+E501V+Y504T.

The glucoamylase may be added in amounts from 0.1-100 micrograms EP/g, such as 0.5-50 micrograms EP/g, such as 1-25 micrograms EP/g, such as 2-12 micrograms EP/g DS.

Trehalase Present and/or Added in Saccharification and/or Fermentation

According to the process of the invention a trehalase of the invention is present and/or added during the
saccharification step (b);
fermentation step (c);
simultaneous saccharification and fermentation;
optionally presaccharification step before step (b).

In a preferred embodiment the mature trehalase disclosed in SEQ ID NO: 30 or SEQ ID NO: 2. In a preferred embodiment the mature trehalase disclosed in SEQ ID NO: 4. In a preferred embodiment the trehalase is present and/or added in an amount between 0.01-20 ug EP (Enzyme Protein) trehalase/g DS, such as between 0.05-15 ug EP terhalase/g DS, such as between 0.5 and 10 ug EP trehalase/g DS.

Glucoamylase Present and/or Added in Saccharification and/or Fermentation

The glucoamylase present and/or added during saccharification step (b); fermentation step (c); simultaneous saccharification and fermentation; or presaccharification before step (b), may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al. (1984), EMBO J. 3 (5), p. 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (Agric. Biol. Chem. (1991), 55 (4), p. 941-949), or variants or fragments thereof. Other *Aspergillus* glucoamylase variants include variants with enhanced thermal stability: G137A and G139A (Chen et al. (1996), Prot. Eng. 9, 499-505); D257E and D293E/Q (Chen et al. (1995), Prot. Eng. 8, 575-582); N182 (Chen et al. (1994), Biochem. J. 301, 275-281); disulphide bonds, A246C (Fierobe et al. (1996), Biochemistry, 35, 8698-8704; and introduction of Pro residues in position A435 and S436 (Li et al. (1997), Protein Eng. 10, 1199-1204.

Other glucoamylases include *Athelia rolfsii* (previously denoted *Corticium rolfsii*) glucoamylase (see U.S. Pat. No. 4,727,026 and (Nagasaka et al. (1998) "Purification and properties of the raw-starch-degrading glucoamylases from *Corticium rolfsii*, Appl Microbiol Biotechnol 50:323-330),

*Talaromyces* glucoamylases, in particular derived from *Talaromyces emersonii* (WO 99/28448), *Talaromyces leycettanus* (U.S. Pat. No. Re. 32,153), *Talaromyces duponti, Talaromyces thermophilus* (U.S. Pat. No. 4,587,215). In a preferred embodiment the glucoamylase used during saccharification and/or fermentation is the *Talaromyces emersonii* glucoamylase disclosed in WO 99/28448.

Bacterial glucoamylases contemplated include glucoamylases from the genus *Clostridium*, in particular *C. thermoamylolyticum* (EP 135,138), and *C. thermohydrosulfuricum* (WO 86/01831).

Contemplated fungal glucoamylases include *Trametes cingulate* (SEQ ID NO: 20), *Pachykytospora papyracea*; and *Leucopaxillus giganteus* all disclosed in WO 2006/069289; or *Peniophora rufomarginata* disclosed in WO2007/124285; or a mixture thereof. Also hybrid glucoamylase are contemplated according to the invention. Examples include the hybrid glucoamylases disclosed in WO 2005/045018. Specific examples include the hybrid glucoamylase disclosed in Table 1 and 4 of Example 1 (which hybrids are hereby incorporated by reference).

In an embodiment the glucoamylase is derived from a strain of the genus *Pycnoporus*, in particular a strain of *Pycnoporus sanguineus* as described in WO 2011/066576 (SEQ ID NOs 2, 4 or 6), in particular the one shown a SEQ ID NO: 28 herein (corresponding to SEQ ID NO: 4 in WO 2011/066576) or from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is SEQ ID NO: 2 in WO 2011/068803 or SEQ ID NO: 19 herein (i.e. *Gloeophyllum sepiarium* glucoamylase). In a preferred embodiment the glucoamylase is SEQ ID NO: 20 herein (i.e., *Gloeophyllum trabeum* glucoamylase discloses as SEQ ID NO: 3 in WO2014/177546) (all references hereby incorporated by reference).

Contemplated are also glucoamylases which exhibit a high identity to any of the above mentioned glucoamylases, i.e., at least 60%, such as at least 70%, at least 75%, at least 80%, at least 85%, at least 90%, at least 95%, at least 96%, at least 97%, at least 98%, at least 99% or even 100% identity to any one of the mature parts of the enzyme sequences mentioned above, such as any of SEQ ID NOs: 13, 14, 19, 20 or 28 herein, respectively.

In an embodiment the glucoamylase used in fermentation or SSF exhibits at least 60%, such as at least 70%, at least 75%, at least 80%, at least 85%, at least 90%, at least 95%, at least 96%, at least 97%, at least 98%, at least 99% or even 100% identity to the mature part of SEQ ID NO: 20 herein.

In an embodiment the glucoamylase used in fermentation or SSF exhibits at least 60%, such as at least 70%, at least 75%, at least 80%, at least 85%, at least 90%, at least 95%, at least 96%, at least 97%, at least 98%, at least 99% or even 100% identity to the mature part of SEQ ID NO: 28 herein.

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

Glucoamylases may in an embodiment be added to the saccharification and/or fermentation in an amount of 1-1,000 µg EP/g DS, preferably 10-500 µg/gDS, especially between 25-250 µg/g DS.

In an embodiment the glucoamylase is added as a blend further comprising an alpha-amylase. In a preferred embodiment the alpha-amylase is a fungal alpha-amylase, especially an acid fungal alpha-amylase. The alpha-amylase is typically a side activity.

In an embodiment the glucoamylase is a blend comprising *Talaromyces emersonii* glucoamylase disclosed in WO 99/28448 as SEQ ID NO: 34 or SEQ ID NO: 13 herein and *Trametes cingulata* glucoamylase disclosed as SEQ ID NO: 2 in WO 06/069289 and SEQ ID NO: 14 herein.

In an embodiment the glucoamylase is a blend comprising *Talaromyces emersonii* glucoamylase disclosed in SEQ ID NO: 13 herein, *Trametes cingulata* glucoamylase disclosed as SEQ ID NO: 14 herein, and *Rhizomucor pusillus* alpha-amylase with *Aspergillus niger* glucoamylase linker and SBD disclosed as V039 in Table 5 in WO 2006/069290 or SEQ ID NO: 15 herein.

In an embodiment the glucoamylase is a blend comprising *Gloeophyllum sepiarium* glucoamylase shown as SEQ ID NO: 19 herein and *Rhizomucor pusillus* with an *Aspergillus niger* glucoamylase linker and starch-binding domain (SBD), disclosed SEQ ID NO: 15 herein with the following substitutions: G128D+D143N.

In an embodiment the alpha-amylase may be derived from a strain of the genus *Rhizomucor*, preferably a strain the *Rhizomucor pusillus*, such as the one shown in SEQ ID NO: 3 in WO2013/006756, or the genus *Meripilus*, preferably a strain of *Meripilus giganteus*. In a preferred embodiment the alpha-amylase is derived from a *Rhizomucor pusillus* with an *Aspergillus niger* glucoamylase linker and starch-binding domain (SBD), disclosed as V039 in Table 5 in WO 2006/069290 or SEQ ID NO: 15 herein.

In an embodiment the *Rhizomucor pusillus* alpha-amylase or the *Rhizomucor pusillus* alpha-amylase with a linker and starch-binding domain (SBD), preferably *Aspergillus niger* glucoamylase linker and SBD, has at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+K192R+P219C; G128D+Y141W+D143N+K192R; or G128D+Y141W+D143N+K192R+P219C (using SEQ ID NO: 3 in WO 2013/006756 for numbering or SEQ ID NO: 15 herein).

In a preferred embodiment the glucoamylase blend comprises *Gloeophyllum sepiarium* glucoamylase (e.g., SEQ ID NO: 2 in WO 2011/068803 or SEQ ID NO: 19 herein) and *Rhizomucor pusillus* alpha-amylase.

In a preferred embodiment the glucoamylase blend comprises *Gloeophyllum sepiarium* glucoamylase shown as SEQ ID NO: 2 in WO 2011/068803 or SEQ ID NO: 19 herein and *Rhizomucor pusillus* with a linker and starch-binding domain (SBD), preferably *Aspergillus niger* glucoamylase linker and SBD, disclosed SEQ ID NO: 3 in WO 2013/006756 and SEQ ID NO: 15 herein with the following substitutions: G128D+D143N.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ EXCEL, SPIRIZYME ACHIEVE™, and AMG™ E (from Novozymes A/S); OPTIDEX™ 300, GC480, GC417 (from DuPont-Danisco);

AMIGASE™ and AMIGASE™ PLUS (from DSM); G-ZYME™ G900, G-ZYME™ and G990 ZR (from DuPont-Danisco).

Cellulolytic Enzyme Composition Present and/or Added in Saccharification and/or Fermentation According to the invention a cellulolytic enzyme composition may be present in saccharification, fermentation or simultaneous saccharification and fermentation (SSF).

The cellulolytic enzyme composition comprises a beta-glucosidase, a cellobiohydrolase and an endoglucanase.

Examples of suitable cellulolytic composition can be found in WO 2008/151079 and WO 2013/028928 which are incorporated by reference.

In preferred embodiments the cellulolytic enzyme composition is derived from a strain of *Trichoderma, Humicola,* or *Chrysosporium*.

In an embodiment the cellulolytic enzyme composition is derived from a strain of *Trichoderma reesei, Humicola insolens* and/or *Chrysosporium lucknowense*.

In an embodiment the cellulolytic enzyme composition comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637 (in particular the *Aspergillus oryzae* beta-glucosidase variant fusion protein shown in SEQ ID NOs: 73 and 74, respectively, in WO 2008/057637 or the *Aspergillus oryzae* beta-glucosidase fusion protein shown in SEQ ID NOs: 75 and 76, respectively, in WO 2008/057637—both hereby incorporated by reference), or *Aspergillus fumigatus*, such as one disclosed in WO 2005/047499 or SEQ ID NO: 10 herein or an *Aspergillus fumigatus* beta-glucosidase variant disclosed in WO 2012/044915 (Novozymes), such as one with one or more, such as all, of the following substitutions: F100D, S283G, N456E, F512Y; or a strain of the genus a strain *Penicillium*, such as a strain of the *Penicillium brasilianum* disclosed in WO 2007/019442, or a strain of the genus *Trichoderma*, such as a strain of *Trichoderma reesei*.

In an embodiment the cellulolytic enzyme composition comprises a GH61 polypeptide having cellulolytic enhancing activity such as one derived from the genus *Thermoascus*, such as a strain of *Thermoascus aurantiacus*, such as the one described in WO 2005/074656 as SEQ ID NO: 2 or SEQ ID NO: 21 herein; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397 as SEQ ID NO: 2 or SEQ ID NO: 12 herein.

In an embodiment the cellulolytic composition comprises a cellobiohydrolase I (CBH I), such as one derived from a strain of the genus *Aspergillus*, such as a strain of *Aspergillus fumigatus*, such as the Cel7a CBH I disclosed in SEQ ID NO: 2 in WO 2011/057140 or SEQ ID NO: 6 herein, or a strain of the genus *Trichoderma*, such as a strain of *Trichoderma reesei*.

In an embodiment the cellulolytic composition comprises a cellobiohydrolase II (CBH II, such as one derived from a strain of the genus *Aspergillus*, such as a strain of *Aspergillus fumigatus* disclosed as SEQ ID NO: 8 herein; or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

In an embodiment the cellulolytic enzyme composition comprises a GH61 polypeptide having cellulolytic enhancing activity and a beta-glucosidase.

In an embodiment the cellulolytic composition comprises a GH61 polypeptide having cellulolytic enhancing activity, a beta-glucosidase, and a CBH I.

In an embodiment the cellulolytic composition comprises a GH61 polypeptide having cellulolytic enhancing activity, a beta-glucosidase, a CBH I, and a CBH II.

In an embodiment the cellulolytic enzyme composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656 or SEQ ID NO: 21 herein), and *Aspergillus oryzae* beta-glucosidase fusion protein (WO 2008/057637).

In an embodiment the cellulolytic composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656 or SEQ ID NO: 21 herein) and *Aspergillus fumigatus* beta-glucosidase (SEQ ID NO: 2 of WO 2005/047499 or SEQ ID NO: 10 herein).

In an embodiment the cellulolytic enzyme composition is a *Trichoderma reesei* cellulolytic enzyme composition further comprising *Penicillium emersonii* GH61A polypeptide having cellulolytic enhancing activity disclosed as SEQ ID NO: 2 in WO 2011/041397 or SEQ ID NO: 12 herein and *Aspergillus fumigatus* beta-glucosidase (SEQ ID NO: 2 of WO 2005/047499 or SEQ ID NO: 10 herein) or a variant thereof with the following substitutions F100D, S283G, N456E, F512Y (using SEQ ID NO: 10 herein for numbering).

In a preferred embodiment the cellulolytic enzyme composition comprising one or more of the following components:

(i) an *Aspergillus fumigatus* cellobiohydrolase I;
(ii) an *Aspergillus fumigatus* cellobiohydrolase II;
(iii) an *Aspergillus fumigatus* beta-glucosidase or variant thereof; and
(iv) a *Penicillium* sp. GH61 polypeptide having cellulolytic enhancing activity; or homologs thereof.

In an preferred embodiment the cellulolytic enzyme composition is derived from *Trichoderma reesei* comprising GH61A polypeptide having cellulolytic enhancing activity derived from a strain of *Penicillium emersonii* (SEQ ID NO: 2 in WO 2011/041397 or SEQ ID NO: 12 herein), *Aspergillus fumigatus* beta-glucosidase (SEQ ID NO: 2 in WO 2005/047499 or SEQ ID NO: 10 herein) variant with the following substitutions: F100D, S283G, N456E, F512Y (disclosed in WO 2012/044915); *Aspergillus fumigatus* Cel7A CBH I disclosed as SEQ ID NO: 6 in WO2011/057140 or SEQ ID NO: 6 herein and *Aspergillus fumigatus* CBH II disclosed as SEQ ID NO: 18 in WO 2011/057140 or SEQ ID NO: 8 herein.

In an embodiment the cellulolytic composition is dosed from 0.0001-3 mg EP/g DS, preferably, 0.0005-2 mg EP/g DS, preferably 0.001-1 mg/g DS, more preferably 0.005-0.5 mg EP/g DS, and even more preferably 0.01-0.1 mg EP/g DS.

Proteases Present and/or Added in Saccharification and/or Fermentation

Any suitable protease may be added in saccharification and/or fermentation, such as SSF.

In a preferred embodiment the protease is a metallo protease or a serine protease.

In an embodiment the enzyme composition comprises a metallo protease, preferably derived from a strain of the genus *Thermoascus*, preferably a strain of *Thermoascus aurantiacus*, especially *Thermoascus aurantiacus* CGMCC No. 0670, such as the metallo protease disclosed as the mature part of SEQ ID NO: 2 disclosed in WO 2003/048353 or the mature polypeptide of SEQ ID NO: 17 herein.

In an embodiment the protease has at least 60%, such as at least 70%, such as at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, or 100% identity to the mature part of the polypeptide of SEQ ID NO: 17 herein.

In an embodiment the protease is derived from a strain of *Pyrococcus*, such as a strain of *Pyrococcus furiosus*, such as the protease shown in SEQ ID NO: 1 in U.S. Pat. No. 6,358,726 or SEQ ID NO: 22 herein.

In an embodiment the protease is the mature sequence from *Meripilus giganteus* protease 3 (peptidase family S53 protease) concerned in Example 2 in WO 2014/037438 (hereby incorporated by reference). In an embodiment the protease is the mature protease 3 sequence from a strain of *Meripilus*, in particular *Meripilus giganteus* shown as SEQ ID NO: 5 in WO 2014/037438 (hereby incorporated by reference) and SEQ ID NO: 32 herein.

In an embodiment the protease has at least 60%, such as at least 70%, such as at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, or 100% identity to the mature part of the polypeptide of SEQ ID NO: 32 herein shown as amino acids 1-547.

Alpha-Amylase Present and/or Added in Saccharification and/or Fermentation

Any suitable alpha-amylase, such as fungal acid alpha-amylase, may be present and/or added in saccharification and/or fermentation.

In a preferably embodiment the alpha-amylase is a fungal alpha-amylase, in particular one that has at least 60%, such as at least 70%, such as at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, or 100% identity to the mature part of the polypeptide of SEQ ID NO: 15. In a preferred embodiment the alpha-amylase has one or more of the following substitutions: G128D, D143N, in particular G128D+D143N.

Processes of Producing a Fermentation Product From Cellulolic Materials Using a Trehalase of the Invention In an embodiment the invention relates to processes of producing a fermentation product from pretreated cellulosic material, comprising:
(a) hydrolyzing said pretreated cellulosic material with a cellulolytic enzyme composition;
(b) fermenting using a fermenting organism; and
(c) optionally recovering the fermentation product,
wherein a trehalase of the invention is added and/or present in hydrolysis step (a) and/or fermentation step (b).

According to the process of the invention hydrolysis and fermentation may be carried out separate or simultaneous. In an embodiment the process of the invention is carried out as separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); or direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step. SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in a HHF process can be carried out at different temperatures, i.e., high temperature enzymatic hydrolysis followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product.

According to the invention the cellulosic material is plant material chips, plant stem segments and/or whole plant stems. In an embodiment cellulosic material is selected from the group comprising arundo, bagasse, bamboo, corn cob, corn fiber, corn stover, miscanthus, orange peel, rice straw, switchgrass, wheat straw. In a preferred embodiment the source of the cellulosic material is corn stover, corn cobs, and/or wheat straw.

According to the invention any pretreatment may be used. In a preferred embodiment chemical pretreatment, physical pretreatment, or chemical pretreatment and a physical pretreatment is used. In a preferred embodiment the cellulosic material is pretreated with an acid, such as dilute acid pretreatment. In an embodiment the cellulosic material is prepared by pretreating cellulosic material at high temperature, high pressure with an acid.

In an embodiment hydrolysis is carried out at a temperature between 20-70° C., such as 30-60° C., preferably 45-55° C. at a pH in the range 4-6, such as 4.5-5.5.

In an embodiment the cellulosic material is present at 1-20 (w/w) % of TS, such as 2-10 (w/w) % TS, such as around 5 (w/w) % TS during hydrolysis.

In an embodiment the hydrolysis is carried out for 1-20 days, preferably between from 5-15 days.

In an embodiment the cellulolytic enzyme composition is derived from *Trichoderma reesei, Humicola insolens* or *Chrysosporium lucknowense*.

Cellulolytic enzyme composition: The term "cellulolytic enzyme composition" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Examples of cellulolytic compositions can be found in the "Cellulolytic Enzyme Composition present and/or added during Saccharification and/or Fermentation"-section above.

Cellulosic material: The term "cellulosic material" means any material containing cellulose. The predominant polysaccharide in the primary cell wall of cellulosic material is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, N.Y.). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20 (polyoxyethylene sorbitan monolaurate).

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 μmole of p-nitrophenolate anion produced per minute at 40° C., pH 5 from 1 mM p-nitrophenyl-beta-D-xyloside as substrate in 100 mM sodium citrate containing 0.01% TWEEN® 20.

Cellobiohydrolase: The term "cellobiohydrolase" means a 1,4-beta-D-glucan cellobiohydrolase (E.C. 3.2.1.91) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581. In the present invention, the Tomme et al. method can be used to determine cellobiohydrolase activity.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of cellulose when used in conjunction with a cellulase or a mixture of cellulases.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, Microbial hemicellulases. *Current Opinion In Microbiology* 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In an aspect, a mixture of CELLUCLAST® 1.5 L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

Fermenting Organism for Cellulosic Based Fermentation

The term "fermenting organism" or 'fermenting microorganism" refers to any organism, including bacterial and fungal organisms, suitable for use in a desired fermentation process to produce a fermentation product. The fermenting organism may be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting organisms that can ferment hexose sugars include bacterial and fungal organisms, such as yeast. Preferred yeast includes strains of *Candida, Kluyveromyces*, and *Saccharomyces*, e.g., *Candida sonorensis, Kluyveromyces marxianus*, and *Saccharomyces cerevisiae*.

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans; Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis*, and *C. scehatae; Clostridium*, such as *C. acetobutylicum, C. thermocellum*, and *C. phytofermentans; E. coli*, especially *E. coli* strains that have been genetically modified to improve the yield of ethanol; *Geobacillus* sp.; *Hansenula*, such as *Hansenula anomala; Klebsiella*, such as *K. oxytoca; Kluyveromyces*, such as *K. marxianus, K. lactis, K. thermotolerans*, and *K. fragilis; Schizosaccharomyces*, such as *S. pombe; Thermoanaerobacter*, such as *Thermoanaerobacter saccharolyticum*; and *Zymomonas*, such as *Zymomonas mobilis*.

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida blankii*. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida scehatae*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*.

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacilus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered Saccharomyces yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis*, *Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the processes of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products

According to the invention the term "fermentation product" can be any substance derived from fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more (e.g., several) hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, Appl. Microbiol. Biotechnol. 59: 400-408; Nigam and Singh, 1995, Processes for fermentative production of xylitol—a sugar substitute, *Process Biochemistry* 30(2): 117-124; Ezeji et al., 2003, Production of acetone, butanol and ethanol by *Clostridium beijerinckii* BA101 and in situ recovery by gas stripping, *World Journal of Microbiology and Biotechnology* 19(6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard and Margaritis, 2004, Empirical modeling of batch fermentation kinetics for poly(glutamic acid) production and other microbial biopolymers, *Biotechnology and Bioengineering* 87(4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, Miya, and Kiriyama, 1997, Studies on hydrogen production by continuous culture system of hydrogen-producing anaerobic bacteria, *Water Science and Technology* 36(6-7): 41-47; and Gunaseelan, 1997, Anaerobic digestion of biomass for methane production: A review, *Biomass and Bioenergy,* 13(1-2): 83-114.

In another preferred aspect, the fermentation product is isoprene.

In another preferred aspect, the fermentation product is a ketone. It will be understood that the term "ketone" encompasses a substance that contains one or more (e.g., several) ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen and Lee, 1997, Membrane-mediated extractive fermentation for lactic acid production from cellulosic biomass, *Appl. Biochem. Biotechnol.* 63-65: 435-448.

Recovery

The fermentation product(s) are optionally recovered after fermentation using any method known in the art including, but not limited to, chromatography, electrophoretic procedures, differential solubility, distillation, or extraction. For example, alcohol, such as ethanol, is separated from the fermented material and purified by conventional methods of distillation. Ethanol with a purity of up to about 96 vol. % can be obtained, which can be used as, for example, fuel ethanol, drinking ethanol, i.e., potable neutral spirits, or industrial ethanol.

The present invention is further described by the following examples that should not be construed as limiting the scope of the invention.

EXAMPLES

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Materials & Methods

Enzymes:

Trehalase (Ms37 tr or Ms trehalase) (P33WJF) from *Myceliophthora sepedonium* is shown as amino acids 21-697 in SEQ ID NO: 30 herein.

Trehalase (Cv37 tr or Cv trehalase) (P33W9X) from *Chaetomium virescens* is shown as amino acids 21-690 in SEQ ID NO: 4 herein.

Trehalase (Tr37 tr or Tr37 trehalase) (P337ZG) from *Trichoderma reesei* is shown as SEQ ID NO: 12 in WO 2013/148993 and SEQ ID NO: 16 herein.

Trehalase (Tr65 tr or Tr65 trehalase) (P24TTB) from *Trichoderma reesei* is shown as SEQ ID NO: 31 herein.

Cellulase VD: Cellulolytic composition derived from *Trichoderma reesei* comprising GH61A polypeptide having cellulolytic enhancing activity derived from a strain of *Penicillium emersonii* (SEQ ID NO: 2 in WO 2011/041397 or SEQ ID NO: 8 herein), *Aspergillus fumigatus* beta-glucosidase (SEQ ID NO: 2 in WO 2005/047499 or SEQ ID NO: 6 herein) variant with the following substitutions: F100D, S283G, N456E, F512Y, disclosed in WO 2012/044915; *Aspergillus fumigatus* Cel7A CBH I disclosed as SEQ ID NO: 6 in WO2011/057140 and SEQ ID NO: 6 herein and *Aspergillus fumigatus* CBH II disclosed as SEQ ID NO: 18 in WO 2011/057140 and as SEQ ID NO: 8 herein.

Alpha-Amylase A (AAA): *Bacillus stearothermophilus* alpha-amylase with the mutations I181*+G182*+N193F truncated to 491 amino acids (SEQ ID NO: 18 herein).

Alpha-Amylase 369 (AA369): *Bacillus stearothermophilus* alpha-amylase with the mutations: I181*+G182*+N193F+V59A+Q89R+E129V+K177L+R179E+Q254S+M284V truncated to 491 amino acids (SEQ ID NO: 18).

Alpha-Amylase Blend B (AABB): Blend of Alpha-Amylase 369, Glucoamylase PoAMG498 and Pfu protease in a ratio of approximately 55:120:1 on µg Enzyme Protein basis.

*Penicillium oxalicum* glucoamylase variant PE498 ("PoAMG498"): *Penicillium oxalicum* glucoamylase variant having the following mutations: K79V+P2N+P4S+P11F+T65A+Q327F (using SEQ ID NO: 23 herein for numbering):

Protease Pfu ("PFU"): Protease derived from *Pyrococcus furiosus* shown in SEQ ID NO: 22 herein.

Glucoamylase E: comprises a blend comprising *Talaromyces emersonii* glucoamylase disclosed in WO99/28448 (SEQ ID NO: 13 herein), *Trametes cingulata* glucoamylase disclosed as SEQ ID NO: 2 in WO 06/69289 and SEQ ID NO: 14 herein, and *Rhizomucor pusillus* alpha-amylase with *Aspergillus niger* glucoamylase linker and SBD disclosed as SEQ ID NO: 15 herein with the following substitutions: G128D+D143N (activity ratio AGU:AGU:FAU(F): approx. 30:7:1).

Glucoamylase U: Blend comprising *Talaromyces emersonii* glucoamylase disclosed as SEQ ID NO: 34 in WO99/28448, *Trametes cingulata* glucoamylase disclosed as SEQ ID NO: 2 in WO 06/69289 and *Rhizomucor pusillus* alpha-amylase with *Aspergillus niger* glucoamylase linker and starch binding domain (SBD) disclosed disclosed in SEQ ID NO: 15 herein with the following substitutions: G128D+D143N (activity ratio in AGU:AGU:FAU-F is about 65:15:1).

Glucoamylase A: Blend of Glucoamylase E and Cellulase VD in a ratio of approximately 10:3 on μg Enzyme Protein basis.

Yeast:
ETHANOL RED™ from Fermentis, USA

Sequence Identity

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–Total Number of Gaps in Alignment)

Trehalase Assay:
Principle:
Trehalose+$H_2O$ $\xrightarrow{Trehalase}$ >2 Glucose
T=37° C., pH=5.7, A340 nm, Light path=1 cm
Spectrophotometric Stop Rate Determination Unit Definition:
One unit will convert 1.0 mmole of trehalose to 2.0 mmoles of glucose per minute at pH 5.7 at 37° C. (liberated glucose determined at pH 7.5).

(See Dahlqvist, A. (1968) Analytical Biochemistry 22, 99-107)

Protease Assays
AZCL-Casein Assay

A solution of 0.2% of the blue substrate AZCL-casein is suspended in Borax/$NaH_2PO_4$ buffer pH9 while stirring. The solution is distributed while stirring to microtiter plate (100 microL to each well), 30 microL enzyme sample is added and the plates are incubated in an Eppendorf Thermomixer for 30 minutes at 45° C. and 600 rpm. Denatured enzyme sample (100° C. boiling for 20 min) is used as a blank. After incubation the reaction is stopped by transferring the microtiter plate onto ice and the colored solution is separated from the solid by centrifugation at 3000 rpm for 5 minutes at 4° C. 60 microL of supernatant is transferred to a microtiter plate and the absorbance at 595 nm is measured using a BioRad Microplate Reader.

pNA-Assay 50 microL protease-containing sample is added to a microtiter plate and the assay is started by adding 100 microL 1 mM pNA substrate (5 mg dissolved in 100 microL DMSO and further diluted to 10 mL with Borax/$NaH_2PO_4$ buffer pH 9.0). The increase in $OD_{405}$ at room temperature is monitored as a measure of the protease activity.

Glucoamylase Activity (AGU)

Glucoamylase activity may be measured in Glucoamylase Units (AGU).

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
| --- | --- |
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
| --- | --- |
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Acid Alpha-Amylase Activity

When used according to the present invention the activity of an acid alpha-amylase may be measured in AFAU (Acid Fungal Alpha-amylase Units) or FAU-F.

Acid Alpha-Amylase Activity (AFAU)

Acid alpha-amylase activity may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

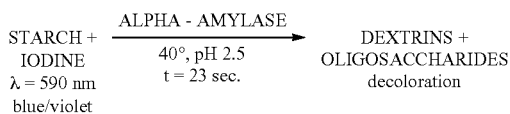

Standard conditions/reaction conditions:

| | |
|---|---|
| Substrate: | Soluble starch, approx. 0.17 g/L |
| Buffer: | Citrate, approx. 0.03M |
| Iodine (I2): | 0.03 g/L |
| CaCl$_2$: | 1.85 mM |
| pH: | 2.50 ± 0.05 |
| Incubation temperature: | 40° C. |
| Reaction time: | 23 seconds |
| Wavelength: | 590 nm |
| Enzyme concentration: | 0.025 AFAU/mL |
| Enzyme working range: | 0.01-0.04 AFAU/mL |

A folder EB-SM-0259.02/01 describing this analytical method in more detail is available upon request to Novozymes A/S, Denmark, which folder is hereby included by reference.

Determination of FAU-F

FAU-F Fungal Alpha-Amylase Units (Fungamyl) is measured relative to an enzyme standard of a declared strength.

| Reaction conditions | |
|---|---|
| Temperature | 37° C. |
| pH | 7.15 |
| Wavelength | 405 nm |
| Reaction time | 5 min |
| Measuring time | 2 min |

A folder (EB-SM-0216.02) describing this standard method in more detail is available on request from Novozymes A/S, Denmark, which folder is hereby included by reference.

Alpha-Amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M Ca$^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

Alpha-Amylase Activity (KNU-A)

Alpha amylase activity is measured in KNU(A) Kilo Novozymes Units (A), relative to an enzyme standard of a declared strength.

Alpha amylase in samples and α-glucosidase in the reagent kit hydrolyze the substrate (4,6-ethylidene(G$_7$)-p-nitrophenyl(G$_1$)-α,D-maltoheptaoside (ethylidene-G$_7$PNP) to glucose and the yellow-colored p-nitrophenol.

The rate of formation of p-nitrophenol can be observed by Konelab 30. This is an expression of the reaction rate and thereby the enzyme activity.

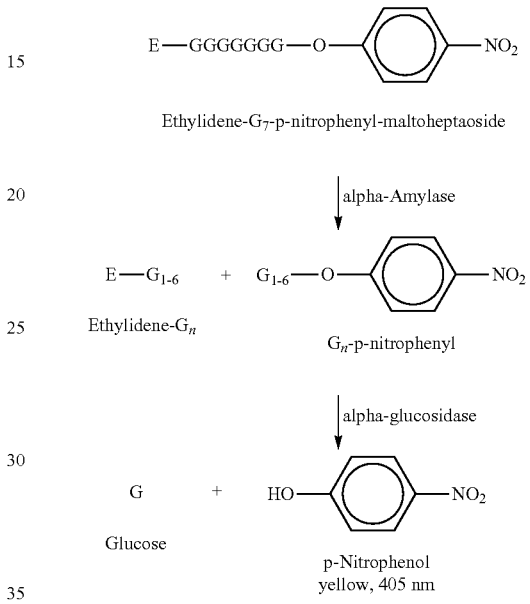

The enzyme is an alpha-amylase with the enzyme classification number EC 3.2.1.1.

| Parameter | Reaction conditions |
|---|---|
| Temperature | 37° C. |
| pH | 7.00 (at 37° C.) |
| Substrate conc. | Ethylidene-G$_7$PNP, R2: 1.86 mM |
| Enzyme conc. (conc. of high/low standard in reaction mixture) | 1.35-4.07 KNU(A)/L |
| Reaction time | 2 min |
| Interval kinetic measuring time | 1/18 sec. |
| Wave length | 405 nm |
| Conc. of reagents/chemicals critical for the analysis | α-glucosidase, R1: ≥3.39 kU/L |

A folder EB-SM-5091.02-D on determining KNU-A actitvity is available upon request to Novozymes A/S, Denmark, which folder is hereby included by reference.

pNP-G7 Assay

The alpha-amylase activity may be determined by a method employing the G7-pNP substrate. G7-pNP which is an abbreviation for 4,6-ethylidene(G$_7$)-p-nitrophenyl(G$_1$)-α, D-maltoheptaoside, a blocked oligosaccharide which can be cleaved by an endo-amylase, such as an alpha-amylase. Following the cleavage, the alpha-Glucosidase included in the kit digest the hydrolysed substrate further to liberate a free PNP molecule which has a yellow color and thus can be measured by visible spectophometry at λ=405 nm (400-420 nm.). Kits containing G7-pNP substrate and alpha-Glucosidase is manufactured by Roche/Hitachi (cat. No. 11876473).

Reagents:

The G7-pNP substrate from this kit contains 22 mM 4,6-ethylidene-G7-pNP and 52.4 mM HEPES (2-[4-(2-hydroxyethyl)-1-piperazinyl]-ethanesulfonic acid), pH 7.0).

The alpha-Glucosidase reagent contains 52.4 mM HEPES, 87 mM NaCl, 12.6 mM $MgCl_2$, 0.075 mM $CaCl_2$, ≥4 kU/L alpha-glucosidase).

The substrate working solution is made by mixing 1 mL of the alpha-Glucosidase reagent with 0.2 mL of the G7-pNP substrate. This substrate working solution is made immediately before use.

Dilution buffer: 50 mM MOPS, 0.05% (w/v) Triton X100 (polyethylene glycol p-(1,1,3,3-tetramethylbutyl)-phenyl ether ($C_{14}H_{22}O(C_2H_4O)$, (n=9-10))), 1 mM CaCl2, pH8.0.

Procedure:

The amylase sample to be analyzed is diluted in dilution buffer to ensure the pH in the diluted sample is 7. The assay is performed by transferring 20 µl diluted enzyme samples to 96 well microtiter plate and adding 80 µl substrate working solution. The solution is mixed and pre-incubated 1 minute at room temperature and absorption is measured every 20 sec. over 5 minutes at OD 405 nm.

The slope (absorbance per minute) of the time dependent absorption-curve is directly proportional to the specific activity (activity per mg enzyme) of the alpha-amylase in question under the given set of conditions. The amylase sample should be diluted to a level where the slope is below 0.4 absorbance units per minute.

Phadebas Activity Assay

The alpha-amylase activity may also be determined by a method using the Phadebas substrate (from for example Magle Life Sciences, Lund, Sweden). A Phadebas tablet includes interlinked starch polymers that are in the form of globular microspheres that are insoluble in water. A blue dye is covantly bound to these microspheres. The interlinked starch polymers in the microsphere are degraded at a speed that is proportional to the alpha-amylase activity. When the alpha-amylse degrades the starch polymers, the released blue dye is water soluble and concentration of dye can be determined by measuring absorbance at 620 nm. The concentration of blue is proportional to the alpha-amylase activity in the sample.

The amylase sample to be analysed is diluted in activity buffer with the desired pH. One substrate tablet is suspended in 5 mL activity buffer and mixed on magnetic stirrer. During mixing of substrate transfer 150 µl to microtiter plate (MTP) or PCR-MTP. Add 30 µl diluted amylase sample to 150 µl substrate and mix. Incubate for 15 minutes at 37° C. The reaction is stopped by adding 30 µl M NaOH and mix. Centrifuge MTP for 5 minutes at 4000×g. Transfer 100 µl to new MTP and measure absorbance at 620 nm.

The amylase sample should be diluted so that the absorbance at 620 nm is between 0 and 2.2, and is within the linear range of the activity assay.

Reducing Sugar Activity Assay:

The alpha-amylase activity may also be determined by reducing sugar assay with for example corn starch substrate. The number of reducing ends formed by the alpha-amylase hydrolysing the alpha-1,4-glycosidic linkages in starch is determined by reaction with p-Hydroxybenzoic acid hydrazide (PHBAH). After reaction with PHBAH the number of reducing ends can be measured by absorbance at 405 nm and the concentration of reducing ends is proportional to the alpha-amylase activity in the sample.

The corns starch substrate (3 mg/ml) is solubilised by cooking for 5 minutes in milliQ water and cooled down before assay. For the stop solution prepare a Ka-Na-tartrate/ NaOH solution (K—Na-tartrate (Merck 8087) 50 g/l, NaOH 20 g/l) and prepare freshly the stop solution by adding p-Hydroxybenzoic acid hydrazide (PHBAH, Sigma H9882) to Ka-Na-tartrate/NaOH solution to 15 mg/ml.

In PCR-MTP 50 µl activity buffer is mixed with 50 µl substrate. Add 50 µl diluted enzyme and mix. Incubate at the desired temperature in PCR machine for 5 minutes. Reaction is stopped by adding 75 µl stop solution (Ka-Na-tartrate/ NaOH/PHBAH). Incubate in PCR machine for 10 minutes at 95° C. Transfer 150 µl to new MTP and measure absorbance at 405 nm.

The amylase sample should be diluted so that the absorbance at 405 nm is between 0 and 2.2, and is within the linear range of the activity assay.

EnzChek® Assay:

For the determination of residual amylase activity an EnzChek® Ultra Amylase Assay Kit (E33651, Invitrogen, La Jolla, Calif., USA) may be used.

The substrate is a corn starch derivative, DQ™ starch, which is corn starch labeled with BODIPY® FL dye to such a degree that fluorescence is quenched. One vial containing approx. 1 mg lyophilized substrate is dissolved in 100 microliters of 50 mM sodium acetate (pH 4.0). The vial is vortexed for 20 seconds and left at room temperature, in the dark, with occasional mixing until dissolved. Then 900 microliters of 100 mM acetate, 0.01% (w/v) TRITON® X100, 0.125 mM $CaCl_2$, pH 5.5 is added, vortexed thoroughly and stored at room temperature, in the dark until ready to use. The stock substrate working solution is prepared by diluting 10-fold in residual activity buffer (100 mM acetate, 0.01% (w/v) TRITON® X100, 0.125 mM $CaCl_2$, pH 5.5). Immediately after incubation the enzyme is diluted to a concentration of 10-20 ng enzyme protein/ml in 100 mM acetate, 0.01% (W/v) TRITON® X100, 0.125 mM $CaCl_2$, pH 5.5.

For the assay, 25 microliters of the substrate working solution is mixed for 10 second with 25 microliters of the diluted enzyme in a black 384 well microtiter plate. The fluorescence intensity is measured (excitation: 485 nm, emission: 555 nm) once every minute for 15 minutes in each well at 25° C. and the $V_{max}$ is calculated as the slope of the plot of fluorescence intensity against time. The plot should be linear and the residual activity assay has been adjusted so that the diluted reference enzyme solution is within the linear range of the activity assay.

Determination of Pullulanase Activity (NPUN)

Endo-pullulanase activity in NPUN is measured relative to a Novozymes pullulanase standard. One pullulanase unit (NPUN) is defined as the amount of enzyme that releases 1 micro mol glucose per minute under the standard conditions (0.7% red pullulan (Megazyme), pH 5, 40° C., 20 minutes). The activity is measured in NPUN/ml using red pullulan.

1 mL diluted sample or standard is incubated at 40° C. for 2 minutes. 0.5 mL 2% red pullulan, 0.5 M KCl, 50 mM citric acid, pH 5 are added and mixed. The tubes are incubated at 40° C. for 20 minutes and stopped by adding 2.5 ml 80% ethanol. The tubes are left standing at room temperature for 10-60 minutes followed by centrifugation 10 minutes at 4000 rpm. OD of the supernatants is then measured at 510 nm and the activity calculated using a standard curve.

Media and Solutions

YP+2% glucose medium was composed of 1% yeast extract, 2% peptone and 2% glucose.

YP+2% maltodextrin medium was composed of 1% yeast extract, 2% peptone and 2% maltodextrin.

PDA agar plates were composed of potato infusion (potato infusion was made by boiling 300 g of sliced (washed but unpeeled) potatoes in water for 30 minutes and then decanting or straining the broth through cheesecloth. Distilled water was then added until the total volume of the suspension was one liter, followed by 20 g of dextrose and 20 g of agar powder. The medium was sterilized by autoclaving at 15 psi for 15 minutes (Bacteriological Analytical Manual, 8th Edition, Revision A, 1998).

LB plates were composed of 10 g of Bacto-Tryptone, 5 g of yeast extract, 10 g of sodium chloride, 15 g of Bacto-agar, and deionized water to 1 liter.

LB medium was composed of 10 g of Bacto-Tryptone, 5 g of yeast extract, 10 g of sodium chloride, and deionized water to 1 liter.

COVE sucrose plates were composed of 342 g of sucrose, 20 g of agar powder, 20 ml of COVE salts solution, and deionized water to 1 liter. The medium was sterilized by autoclaving at 15 psi for 15 minutes (Bacteriological Analytical Manual, 8th Edition, Revision A, 1998). The medium was cooled to 60° C. and 10 mM acetamide, 15 mM CsCl, TRITON® X-100 (50 µl/500 ml) were added.

COVE salts solution was composed of 26 g of MgSO4.7H2O, 26 g of KCL, 26 g of KH2PO4, 50 ml of COVE trace metals solution, and deionized water to 1 liter.

COVE trace metals solution was composed of 0.04 g of Na2B4O7.10H2O, 0.4 g of CuSO4.5H2O, 1.2 g of FeSO4.7H2O, 0.7 g of MnSO4.H2O, 0.8 g of Na2MoO4.2H2O, 10 g of ZnSO4.7H2O, and deionized water to 1 liter.

Example 1

Cloning of *Chaetomium virescens* Trehalase (Cv37 tr) Polypeptide (P33W9X) Coding Sequence from *Chaetomium virescens* CBS547.75.

The *Chaetomium virescens* trehalase (Cv Trehalase) polypeptide coding sequence was cloned from *Chaetomium virescens* CBS547.75 DNA by PCR.

*Chaetomium virescens* CBS547.75 was purchased from the Centraalbureau voor Schimmelcultures (Utrecht, the Netherlands). The fungal strain was cultivated in 100 ml of YP+2% glucose medium in 1000 ml Erlenmeyer shake flasks for 5 days at 20° C. Mycelia were harvested from the flasks by filtration of the medium through a Buchner vacuum funnel lined with MIRACLOTH® (EMD Millipore, Billerica, Mass., USA). Mycelia were frozen in liquid nitrogen and stored at −80° C. until further use. Genomic DNA was isolated using a DNEASY® Plant Maxi Kit (QIAGEN GMBH, Hilden Germany) according to the manufacturer's instructions.

Genomic sequence information was generated by Illumina MySeq (Illumina Inc., San Diego, Calif.). 5 µgs of the isolated *Chaetomium virescens* genomic DNA was used for library preparation and analysis according to the manufacturer's instructions. Genes were called using GeneMark.hmm ES version 2.3c and identification of the catalytic domain was made using "Trehalase PF01204" Hidden Markov Model provided by Pfam. The polypeptide coding sequence for the entire coding region was cloned from *Chaetomium virescens* CBS547.75 genomic DNA by PCR using the primers (SEQ ID NO: 24 and SEQ ID NO: 25) described below.

KKSC0334-F
(SEQ ID NO: 24)
5'- ACACAACTGGGGATCCACCATGACGCTCCGACACCTCGG -3'

KKSC0334-R
(SEQ ID NO: 25)
5'- CTAGATCTCGAGAAGCTTTCACGACCTCCTCCCTACCC -3'

Bold letters represent *Chaetomium virescens* enzyme coding sequence. Restriction sites are underlined. The sequence to the left of the restriction sites is homologous to the insertion sites of pDau109 (WO 2005/042735).

The amplification reaction (50 µls) was performed according to the manufacturer's instructions (Phusion HiFi DNA polymerase cat # M0530S, New England Biolabs Inc.) with the following final concentrations:

| PCR mix | |
|---|---|
| 5x HF Phusion Buffer | 10 ul |
| dNTP 10 mM | 1 ul |
| DMSO | 1.5 ul |
| Primer F | 1 ul |
| Prime R | 1 ul |
| Phusion polymerase | 0.5 uls |
| H2O | 35 ul |
| Genomic DNA | 1 uls |
| Total volume | 50 uls |

The PCR reaction was incubated in a DYAD® Dual-Block Thermal Cycler (BioRad, USA) programmed for 1 cycle at 98° C. for 30 seconds; 35 cycles each at 98° C. for 10 seconds, 72° C. for 2 minutes followed by 1 cycle at 72° C. for 7 minutes. Samples were cooled to 10° C. before removal and further processing.

Four µl of the PCR reaction was analyzed by 1% agarose gel electrophoresis using 40 mM Tris base, 20 mM sodium acetate, 1 mM disodium EDTA (TAE) buffer. A major band of about 2241 bp was observed. The remaining PCR reaction was purified directly with an ILLUSTRA™ GFX™ PCR DNA and Gel Band Purification Kit (GE Healthcare, Piscataway, N.J., USA) according to the manufacturer's instructions.

Two µg of plasmid pDau109 was digested with Bam HI and Hind III and the digested plasmid was run on a 1% agarose gel using 50 mM Tris base-50 mM boric acid-1 mM disodium EDTA (TBE) buffer in order to remove the stuffer fragment from the restricted plasmid. The bands were visualized by the addition of SYBR® Safe DNA gel stain (Life Technologies Corporation, Grand Island, N.Y., USA) and use of a 470 nm wavelength transilluminator. The band corresponding to the restricted plasmid was excised and purified using an ILLUSTRA™ GFX™ PCR DNA and Gel Band Purification Kit (Cat. no 28-9034-70 from GE Healthcare). The plasmid was eluted into 10 mM Tris pH 8.0 and its concentration adjusted to 20 ng per µl. An IN-FUSION® HD EcoDry-Down PCR Cloning Kit (BD Biosciences, Palo Alto, Calif., USA), was used to clone the 2241 bp PCR fragment into pDau109 digested with Bam HI and Hind III (20 ng). The IN-FUSION® total reaction volume was 10 µl. The IN-FUSION® total reaction volume was 10 µl. The IN-FUSION® reaction was transformed into FUSION-BLUE™ *E. coli* cells (BD Biosciences, Palo Alto, Calif., USA) according to the manufacturer's protocol and plated onto LB agar plates supplemented with 50 µg of ampicillin per ml. After incubation overnight at 37° C., transformant colonies were observed growing under selection on the LB plates supplemented with 50 μg of ampicillin per ml.

One plasmid with the correct *C. virescens* trehalase coding sequence (SEQ ID NO: 3) was chosen. The plasmid was designated pKKSC0334-1. Cloning of the *Chaetomium virescens* trehalase gene into Bam HI-HindIII digested pDau109 resulted in transcription of the *C. virescens* trehalase gene under the control of a NA2-tpi double promoter. NA2-tpi is a modified promoter from an *Aspergillus niger* neutral alpha-amylase gene in which the untranslated leader has been replaced by an untranslated leader from an *Aspergillus nidulans* triose phosphate isomerase gene.

The expression plasmid pKKSC0334-1 was transformed into protoplasts of *Aspergillus oryzae* MT3568 according to the method of European Patent EP 0238023, pages 14-15. *Aspergillus oryzae* MT3568 is an amdS (acetamidase) disrupted derivative of *A. oryzae* JaL355 (WO 2002/40694) in which pyrG auxotrophy was restored in the process of inactivating the *A. oryzae* amdS gene.

*E. coli* 3701 containing pKKSC0334-1 was grown overnight according to the manufacturer's instructions (Genomed) and plasmid Midi DNA of pKKSC0334-1 was isolated using a Plasmid Midi Kit (Genomed JETquick kit, cat. nr. 400250, GENOMED GmbH, Germany) according to the manufacturer's instructions. The purified plasmid DNA was transformed into *Aspergillus oryzae* MT3568. *A. oryzae* MT3568 protoplasts were prepared according to the method of Christensen et al., 1988, Bio/Technology 6: 1419-1422. The selection plates consisted of COVE sucrose with +10 mM acetamide +15 mM CsCl+TRITON® X-100 (50 μl/500 ml). The plates were incubated at 37° C. Briefly, 8 uls of plasmid DNA representing 3 ugs of DNA was added to 100 uls MT3568 protoplasts. 250 ul of 60% PEG solution was added and the tubes were gently mixed and incubate at 37° C. for 30 minutes. The mix was added to 10 ml of pre melted Cove top agarose (The top agarose melted and then the temperature equilibrated to 40° C. in a warm water bath before being added to the protoplast mixture). The combined mixture was then plated on two Cove-sucrose selection petri plates with 10 mM Acetamide. The plates are incubated at 37° C. for 4 days. Single *Aspergillus* transformed colonies were identified by growth on the selection Acetimide as a carbon source. Each of the four *A. oryzae* transformants were inoculated into 750 μl of YP medium supplemented with 2% glucose and also 750 μl of 2% maltodextrin and also DAP4C in 96 well deep plates and incubated at 37° C. stationary for 4 days. At same time the four transformants were restreaked on COVE-2 sucrose agar medium.

Culture broth from the *Aspergillus oryzae* transformants were then analyzed for production of the P33W9X trehalase polypeptide by SDS-PAGE using NUPAGE® 10% Bis-Tris SDS gels (Invitrogen, Carlsbad, Calif., USA) according to the manufacturer. A band at approximately 75 kDa was observed for each of the *Aspergillus oryzae* transformants. One *A. oryzae* transformant producing the P33W9X polypeptide was designated *A. oryzae* EXP09256.

For larger scale production, *A. oryzae* EXP09256 spores were spread onto a PDA plate and incubated for five days at 37° C. The confluent spore plate was washed twice with 5 ml of 0.01% TWEEN® 20 to maximize the number of spores collected. The spore suspension was then used to inoculate nine 500 ml flasks containing 100 ml of Dap-4C medium. The cultures were incubated at 30° C. with constant shaking at 150 rpm. At day four post-inoculation, the culture broth was collected by filtration through a bottle top MF75™ SUPOR® MachV 0.2 μm PES filter (Thermo Fisher Scientific, Roskilde, Denmark). Fresh culture broth from this transformant produced a band of GH37 protein of approximately 75 kDa (designated EXP09256). The identity of this band as the *C. virescens* trehalase polypeptide was verified by peptide sequencing.

Characterization of the EXP09256 trehalase polypeptide coding sequence from *Chaetomium virescens* CBS547.75

The genomic DNA sequence and deduced amino acid sequence of the *Chaetomium virescens* CBS547.75.

The *Chaetomium virescens* trehalase polypeptide (P33W9X) genomic coding sequence is shown in SEQ ID NO: 3 and SEQ ID NO: 4, respectively. The encoded predicted protein is 690 amino acids. Using the SignalP program (Nielsen et al., 1997, supra), a signal peptide of 20 residues was predicted. The predicted mature protein contains 670 amino acids with a predicted molecular mass of 75 kDa and a predicted isoelectric point of 5.5.

Example 2

Expression of Trehalase (P33WJF) from *Myceliophthora sepedonium* (Ms Tr37)

This strain was purchased from UAMH and received on the 12 Sep. 1988 as UAMH5004. UAMH is the University of Alberta Microfungus Collection and Herbarium.

*Myceliophthora sepedonium* strain UAHM5004 was obtained from the University of Alberta Microfungus Collection and Herbarium UAMH, Edmonton, Alberta, Canada T6G 2R3. The earlier genus and species designation *Cornyascus sepedonium* is still employed.

The trehalase polypeptide (P33WJF) coding sequence was cloned from *Myceliophthora sepedonium* strain UAHM5004 DNA by PCR.

The fungal strain was cultivated, DNA isolated genome sequenced and the trehalase enzyme candidate identified as in example 1.

The polypeptide coding sequence for the entire coding region was cloned from *Myceliophthora sepedonium* strain UAHM5004 genomic DNA by PCR using the primers (SEQ ID NO: 26 and SEQ ID NO: 27) described below.

KKSC0335-F (SEQ ID NO: 26)

5'- ACACAACTGGGGATCCACCATGGCGCTACGACACATCGC-3'

KKSC0335-R (SEQ ID NO: 27)

5'- CTAGATCTCGAGAAGCTTTTACGAGACGGAGACACTAAACA

Bold letters represent *Myceliophthora sepedonium* enzyme coding sequence. Restriction sites are underlined. The sequence to the left of the restriction sites is homologous to the insertion sites of pDau109 (WO 2005/042735).

The amplification reaction (50 μls) was performed according to the protocol in example 1 according the manufacturer's instructions (Phusion HiFi DNA polymerase cat # M0530S, New England Biolabs Inc Four μl of the PCR reaction was analyzed by 1% agarose gel electrophoresis using 40 mM Tris base, 20 mM sodium acetate, 1 mM disodium EDTA (TAE) buffer. A major band of about 2354 bp was observed. The remaining PCR reaction was purified directly with an ILLUSTRA™ GFX™ PCR DNA and Gel Band Purification Kit (GE Healthcare, Piscataway, N.J., USA) and cloned into pDau109 as in example 1.

One plasmid with the correct *M. sepedonium* trehalase coding sequence (SEQ ID NO: x) was chosen. The plasmid was designated pKKSC0335-1. The expression plasmid pKKSC0335-1 was transformed into protoplasts of *Aspergillus oryzae* MT3568 and a transformants chosen and propagated also according example 1.

Production of the trehalase polypeptide (P33WJF) by SDS-PAGE using NUPAGE® 10% Bis-Tris SDS gels (Invitrogen, Carlsbad, Calif., USA) according to the manufacturer. A band at approximately 76 kDa was observed for each of the *Aspergillus oryzae* transformants. One *A. oryzae* transformant producing the P33W9X polypeptide was designated *A. oryzae* EXP09258.

Larger scale production, *A. oryzae* EXP09258 was performed also according to Example 1.

Characterization of the EXP09258 trehalase polypeptide coding sequence from *Myceliophthora sepedonium* strain UAHM5004 The genomic DNA sequence and deduced amino acid sequence of the *Myceliophthora sepedonium* strain UAHM5004

Trehalase polypeptide (P33WJF) genomic coding sequence are shown in SEQ ID NO: 1 and SEQ ID NO: 2, respectively. The encoded predicted protein is 697 amino acids. Using the SignalP program (Nielsen et al., 1997, supra), a signal peptide of 20 residues was predicted. The predicted mature protein contains 677 amino acids with a predicted molecular mass of 76 kDa and a predicted isoelectric point of 5.1.

Example 3

Glucose Production with Trehalase Addition Using Supernatant of Ferm Drop

Ferm drop sample at the end of fermentation from industrial corn ethanol plant was first centrifuged, and supernatant was collected for the testing. The trehalose level in the supernatant was analyzed to be around 2 g/L by an Ion Chromatography assay. The pH of the supernatant was measured as 4.6, and LACTROL® was supplemented as antibacterial agent at the level of 3 ppm. Next, 2 ml of supernatant was aliquoted into 15 ml polypropylene tube. Each tube was dosed with trehalase listed in Table 1. The enzyme dosage was 0, 0.05, 0.5 and 5 ug/ml, respectively. Each treatment ran three replicate. Afterwards, all tubes were incubated in 32° C. water bath for 5 hours. Samples were taken at 5 hour of incubation for HPLC analysis. The HPLC preparation consisted of stopping the reaction by addition of 20 micro liters of 40% $H_2SO_4$, and filtering through a 0.45 micrometer filter. Agilent™ 1100 HPLC system coupled with RI detector was used to determine glucose concentration. The separation column was aminex HPX-87H ion exclusion column (300 mm×7.8 mm) from BioRad™.

TABLE 1

List of trehalase tested

| Purified ID | Sequence and ID Code | Donor source |
|---|---|---|
| U3EAN | SEQ ID NO: 30 - P33WJG | *Myceliophthora sepedonium* (Ms37 tr) |
| U3EAJ | SEQ ID NO: 4 - P33W9X | *Chaetomium virescens* (Cv37 tr) |
| U3EAH | SEQ ID NO: 16 - P337ZG | *Trichoderma reesei* (Tr37 tr) |

Results

The glucose results from HPLC analysis is summarized in FIG. 1. Compared to control without any trehalase addition, all treatments with trehalase showed glucose increase. The amount of glucose increase was depended on the dosage of trehalase and its source. Results showed *Myceliophthora sepidonium* trehalase (Ms trehalase) performed the best. At dosage of 0.5 ug/ml, all the trehalose was converted into glucose with 5 hour incubation. *Chaetomium virescens* trehalase was a little less efficient than *Myceliophthora sepidonium* trehalase, but still much better than *Trichoderma reesei* trehalase (Tr tr).

Example 4

Application of Ms Trehalase in Conventional SSF Process for Ethanol Production

All treatments were evaluated via 5 g small assay. Each treatment ran five replicate. Three corn mashes liquefied by Alpha-Amylase Blend B (AABB) (Mash A and B) and Alpha-Amylase A (AAA) (Mash C) from industrial corn ethanol plants were used for the testing. 3 ppm penicillin and 1000 ppm urea were supplemented into each mash. The pH of the slurries was adjusted to 5.0 with 40% $H_2SO_4$ or 50% NaOH. Approximately 5 g of the slurry was added to 15 ml polypropylene tube. The tubes were prepared by drilling a ⅟₃₂ inch hole and the empty tubes were then weighed before corn slurry was added. The tubes were weighed again after mash was added to determine the exact weight of mash in each tube. Each tube was dosed with actual enzyme dosage based on the exact weight of corn slurry in each tube. The enzyme dosage for each treatment was listed in Table 2. Trehalase from *Myceliophthora sepidonium* (Ms37 trehalase) (SEQ ID NO: 30) was used in this study. Afterwards, the tubes were dosed with 50 ul of yeast propagate to around 5 g corn mash, and then were incubated in 32° C. water batch for SSF. Samples were taken at 53 hour of fermentation for HPLC analysis. The HPLC preparation consisted of stopping the reaction by addition of 50 micro liters of 40% $H_2SO_4$, centrifuging, and filtering through a 0.45 micrometer filter. Agilent™ 1100 HPLC system coupled with RI detector was used to determine sugars, acids and ethanol concentration. The separation column was aminex HPX-87H ion exclusion column (300 mm×7.8 mm) from BioRad™.

TABLE 2

AMG and trehalase dosage for each treatment in SSF

| | Mash | AMG | AMG, AGU/g-DS | Trehalase, ug EP/g-DS |
|---|---|---|---|---|
| 1 | Mash A | Glucoamylase U | 0.56 | 0 |
| 2 | | | | 5 |
| 3 | | Glucoamylase E | 0.60 | 0 |
| 4 | | | | 5 |
| 5 | | Glucoamylase A | 0.60 | 0 |
| 6 | | | | 5 |
| 7 | Mash B | Glucoamylase U | 0.56 | 0 |
| 8 | | | | 5 |
| 9 | | Glucoamylase E | 0.60 | 0 |
| 10 | | | | 5 |
| 11 | | Glucoamylase A | 0.60 | 0 |
| 12 | | | | 5 |
| 13 | Mash C | GlucoamylaseU | 0.56 | 0 |
| 14 | | | | 5 |
| 15 | | Glucoamylase E | 0.60 | 0 |
| 16 | | | | 5 |
| 17 | | Glucoamylase A | 0.60 | 0 |
| 18 | | | | 5 |

Results

The results from HPLC analysis were summarized in Table 3. Compared to the control, treatment with trehalase addition achieved much higher ethanol titer, ranging from between 0.5 to 1.2% yield increase.

TABLE 3

Ethanol yield increase with trehalase addition compared to the control in SSF

| Treatment | Mash A | Mash B | Mash C |
|---|---|---|---|
| Glucoamylase U (control) | — | — | — |
| Glucoamylase U + Ms37 trehalase | 0.70% | 0.64% | 0.90% |
| Glucoamylase E (control) | — | — | — |
| Glucoamylase E + Ms37 trehalase | 1.13% | 0.91% | 1.16% |
| Glucoamylase A (control) | — | — | — |
| Glucoamylase A + Ms37 trehalase | 0.54% | 0.64% | 1.01% |

Example 5

Purification of GH37 Trehalases

Filtered culture broth from fermentation of *A. oryzae* harboring the GH37 trehalase gene was added solid ammonium sulfate to a final concentration of 2 M and pH adjusted to 7. The solution, containing the trehalase, was applied to a hydrophobic interaction column (butyl Toyopearl, approximately 50 ml in a XK26 column, equilibrated with buffer A), using as buffer A 50 mM Hepes+2 M ammonium sulfate pH 7.0, and as buffer B 50 mM Hepes pH 7.0. Unbound material was washed off the column with equilibration buffer and the trehalase was eluted with a linear gradient (100% to 0% A) over 5 column volumes and 10 ml fractions were collected. Based on the chromatogram trehalase containing fractions were pooled and dialyzed against a large volume of 20 mM Hepes pH 7.0.

The purified GH37 trehalases are listed in the table below:

| Purified Sample ID | Donor Scientific Name | Protein Sequence Reference ID |
|---|---|---|
| U3EAN | *Myceliophthora sepedonium* | SEQ ID NO: 30 - P33WJF |
| U3EAJ | *Chaetomium virescens* | SEQ ID NO: 4 - P33W9X |
| U3EAH | *Trichoderma reesei* | SEQ ID NO: 16 - P337ZG |

Molecular Weight of the Purified Trehalases

The molecular weight, as estimated from SDS-PAGE, was approximately 100 kDa for all three trehalases and the purity was in all cases >95%.

Example 6

Purification of a GH65 Trehalase from *Trichoderma reesei* (SEQ ID NO: 31)

Filtered culture broth from fermentation of *A. oryzae* harboring the GH65 trehalase gene from *Trichoderma reesei* (P24TTB) was loaded on a gel filtration column (about 780 ml Sephadex G-25 medium) equilibrated with 50 mm Na-acetate pH 5.0 and fractions collected. Based on the chromatogram fractions containing protein (A280>A260) that ran straight throw the column were pooled. The trehalase containing pool was concentrated using a Viva cell with a 30 kDa cut-off membrane.

Molecular Weight of the Purified Trehalases

The molecular weight, as estimated from SDS-PAGE, was approximately 120 kDa and the purity was >95%.

Example 7

Determination of Trehalase Activity (GOD)

GOD-Perid 50 microliter trehalase-containing enzyme solution (appropriately diluted with 20 mM MES buffer pH 5.0) is dispensed in a microtiter plate well (e.g. NUNC 269620) and 50 microliter substrate (10 mg/ml trehalose in 20 mM MES buffer pH 5.0) is added. The plate is sealed and incubated 15 min., shaken with 750 rpm at 32° C. After the incubation 20 microliter of reaction solution is transferred to an empty microtiter plate and 180 microliter GOD-perid [600 ppm glucose oxidase (Sigma G1625), 20 ppm peroxidase (Sigma P8125), 0.1% ATBS (Roche 102946) in 0.1 M K-phosphate buffer pH 7.0] is added. The plate is left for 30 minutes at 20-30° C. and following this the absorbance at 420 nm is measured in a microtiter plate spectrophotometer.

Example 8 pH Profile

The pH profile was determined at 32° C. in the pH range of 2.0 to 7.5 (in 0.5 pH-unit steps) as described above in the section "Determination of trehalase activity, GOD-perid", except that a buffer cocktail (110 mM acetic acid, 110 mM citric acid and 110 mM MES) was used instead of the 20 mM MES buffer pH 5.0 buffer. The results are summarized in table 5 below. The values given for each pH in the range of 2.0-7.5 are the relative activity in % normalized to the value at optimum.

| | Relative activity | | | | | | | | | | | |
|---|---|---|---|---|---|---|---|---|---|---|---|---|
| pH | 2.5 | 3 | 3.5 | 4 | 4.5 | 5 | 5.5 | 6 | 6.5 | 7 | 7.5 | 8 |
| Tr37 tr SEQ ID NO: 16 U3EAH | 36 | 100 | 98 | 68 | 35 | 18 | 16 | 14 | 15 | 13 | 10 | 7 |
| Cv37 tr SEQ ID NO: 4 U3EAJ | 27 | 73 | 81 | 100 | 86 | 77 | 70 | 76 | 90 | 77 | 53 | 25 |
| Ms37 tr SEQ ID NO: 30 U3EAN | 26 | 85 | 88 | 100 | 59 | 52 | 52 | 46 | 2 | 32 | 24 | 18 |

Example 9

Thermostability Using DSC Data

The thermostability of trehalases were determined by Differential Scanning calorimetry (DSC) using a VP-capillary DSC instrument (MicroCal Inc., Piscataway, N.J., USA) equipped with an auto sampler. Aliquots of the trehalase, purified as described in Example 1, were buffer-changed (see buffer in table below) using prepacked NAP-5 columns. The samples were diluted with the corresponding buffer to approximately 0.5 mg/ml and the buffer was used as reference solution. Sample and reference solutions (approx. 0.5 ml) were thermally pre-equilibrated for 10 minutes at 20° C.

and the DSC scan was performed from 20 to 100° C. at a scan rate of 200 K/hour. Data-handling was performed using the MicroCal Origin software (version 7.0383). The thermal denaturation temperature, Td (° C.), was taken as the top of denaturation peak (major endothermic peak) in thermograms (Cp vs. T) obtained after heating the trehalase solution in the buffer at a constant programmed heating rate. Denaturation temperatures were determined at an accuracy of approximately +/−0.5° C.

The results of the DSC measurements are summarized in the table below.

| Purified Sample ID | Donor Scientific Name | Protein Sequence SEQ ID and Reference ID | Buffer | Td (° C.) |
|---|---|---|---|---|
| U3EAN | Myceliophthora sepedonium | SEQ ID NO: 30 P33WJF | 50 mM MES pH 5.0 | 68.9 |
| U3EAJ | Chaetomium virescens | SEQ ID NO: 4 P33W9X | 50 mM MES pH 5.0 | 65.1 |
| U3EAH | Trichoderma reesei | SEQ ID NO: 16 P337ZG | 50 mM MES pH 5.0 | 67.0 |
| U6B9P | Trichoderma reesei | SEQ ID NO: 31 P24TTB | 50 mM MES pH 5.0 | 64.7 |

Example 10

Glucose Production by Ms37 Trehalase (SEQ ID NO: 30) and Tr65 Trehalase (SEQ ID NO: 31)

Ferm drop samples at the end of fermentation from two industrial corn ethanol plants were collected and pH was measured as 4.68 (A) and 4.49 (B) respectively. Ferm drop samples were centrifuged at 3500 rpm for 15 minutes, and then supernatants were collected and used for the trehalase application test. First, penicillium was supplemented as antibacterial agent at the level of 3 ppm. Next, 2 ml of supernatant was aliquoted into 15 ml polypropylene tube. Each tube was dosed with trehalase listed in the table below. The enzyme doses tested were 0, 0.05, 0.15, 0.5 and 5 ug per ml of supernatant. Each treatment ran three replicate. Afterwards, all tubes were incubated in 32° C. water bath for 5 hours. Samples were taken at 5 hour of incubation for HPLC analysis. The HPLC preparation consisted of stopping the reaction by addition of 20 micro liters of 40% H2SO4, and filtering through a 0.45 micrometer filter. Agilent™ 1100 HPLC system coupled with RI detector was used to determine glucose concentration. The separation column was aminex HPX-87H ion exclusion column (300 mm×7.8 mm) from BioRad™.

Trehalases Tested

| Purified ID | GH family | Donor source and SEQ ID |
|---|---|---|
| U3EAN | GH37 | Myceliophthora sepidonium (SEQ ID NO: 30) |
| U6BP9 | GH65 | Trichoderma reesei (SEQ ID NO: 31) |

Results

Figure 2:
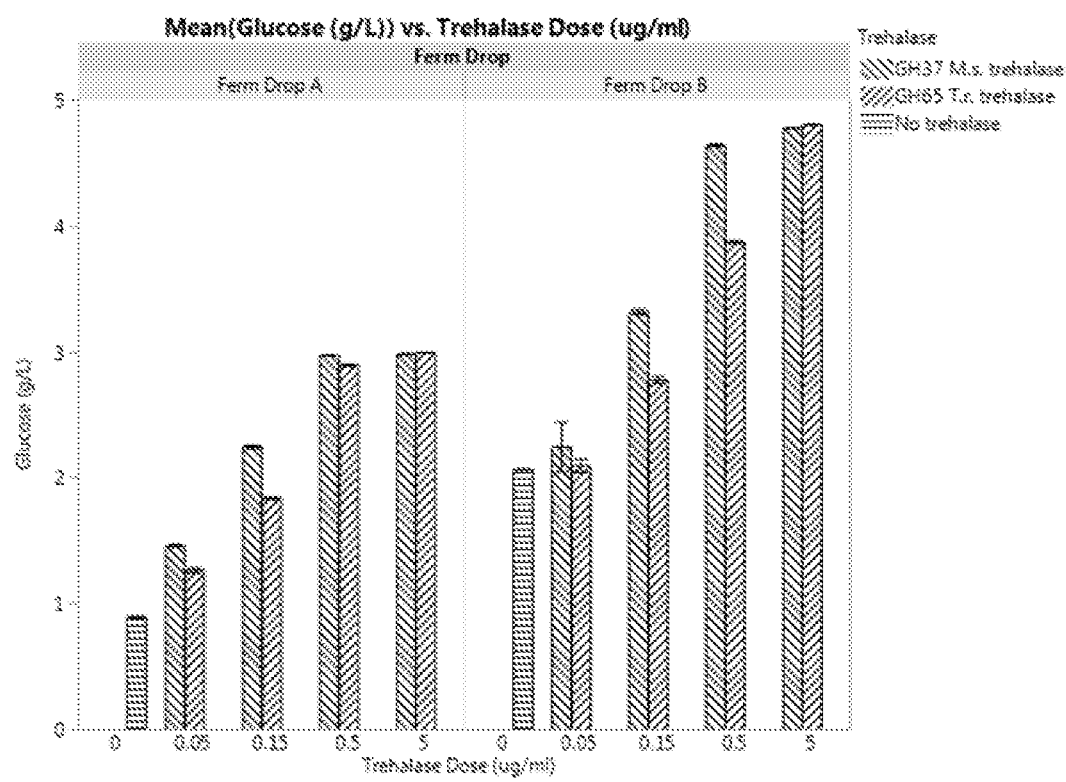
FIG. 2 shows the glucose production by Ms trehalase (SEQ ID NO: 30) and GH65 Tr trehalase (SEQ ID NO: 31) addition in supernatant of ferm drop.

The glucose results from HPLC analysis were summarized by JMP in FIG. 2. Compared to control without any trehalase addition, treatments with trehalase showed glucose increase, except the lowest dose of 0.05 ug/ml in Ferm Drop B. The amount of glucose increase was dependent on the dosage of trehalase and its source. Results showed that Myceliophthora sepidonium GH37 trehalase (SEQ ID NO: 30) performed better than Trichoderma reesei GH65 trehalase (SEQ ID NO: 31). At high dose of 5 ug/ml trehalase addition, the trehalose in ferm drop samples was completely converted to glucose by the trehalases.

The present invention is presented in the following numbered paragraphs:

1. A polypeptide having trehalase activity, selected from the group consisting of:
    (a) a polypeptide having at least 90% sequence identity to the mature polypeptide of SEQ ID NO: 30 or SEQ ID NO: 2 or at least 80% sequence identity to the mature polypeptide of SEQ ID NO: 4;
    (b) a polypeptide encoded by a polynucleotide that hybridizes under high stringency conditions with (i) the mature polypeptide coding sequence of SEQ ID NO: 29, SEQ ID NO: 1 or SEQ ID NO: 3, (ii) the cDNA sequence thereof, or (iii) the full-length complement of (i) or (ii);
    (c) a polypeptide encoded by a polynucleotide having at least 60% sequence identity to the mature polypeptide coding sequence of SEQ ID NO: 29 or SEQ ID NO: 1 or SEQ ID NO: 3 or the cDNA sequence thereof;
    (d) a variant of the mature polypeptide of SEQ ID NO: 30, SEQ ID NO: 2 or SEQ ID NO: 4 comprising a substitution, deletion, and/or insertion at one or more (e.g., several) positions; and
    (e) a fragment of the polypeptide of (a), (b), (c), or (d) that has trehalase activity.

2. The polypeptide of paragraph 1, having at least 91%, at least 92%, at least 93%, at least 94%, at least 95%, at least 96%, at least 97%, at least 98%, at least 99% or 100% sequence identity to the mature polypeptide of SEQ ID NO: 30 or SEQ ID NO: 2.

3. The polypeptide of paragraph 1 or 2, which is encoded by a polynucleotide that hybridizes under very high stringency conditions with (i) the mature polypeptide coding sequence of SEQ ID NO: 29 or SEQ ID NO: 1, (ii) the cDNA sequence thereof, or (iii) the full-length complement of (i) or (ii).

4. The polypeptide of any of paragraphs 1-3, which is encoded by a polynucleotide having at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 29 or SEQ ID NO: 1 or the cDNA sequence thereof.

5. The polypeptide of any of paragraphs 1-4, comprising or consisting of SEQ ID NO: 30 or SEQ ID NO: 2 or the mature polypeptide of SEQ ID NO: 30 shown as amino acids 21-694 or SEQ ID NO: 2 shown as amino acids 21-697 of SEQ ID NO: 2.

6. The polypeptide of any of paragraphs 1-6, which is a variant of the mature polypeptide of SEQ ID NO: 30 or SEQ ID NO: 2 comprising a substitution, deletion, and/or insertion at one or more positions.

7. The polypeptide of any of paragraphs 1-6, which is a fragment of SEQ ID NO: 30 or SEQ ID NO: 2, wherein the fragment has trehalase activity.

8. The polypeptide of any of paragraphs 1-7, having at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 4.

9. The polypeptide of any of paragraphs 1-8, which is encoded by a polynucleotide that hybridizes under very high stringency conditions with (i) the mature polypeptide coding sequence of SEQ ID NO: 3, (ii) the cDNA sequence thereof, or (iii) the full-length complement of (i) or (ii).

10. The polypeptide of any of paragraphs 1-9, which is encoded by a polynucleotide having at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 3 or the cDNA sequence thereof.

11. The polypeptide of any of paragraphs 1-10, comprising or consisting of SEQ ID NO: 4 or the mature polypeptide of SEQ ID NO: 4 shown as amino acids 21-690 of SEQ ID NO: 4.

12. The polypeptide of any of paragraphs 1-11, which is a variant of the mature polypeptide of SEQ ID NO: 4 comprising a substitution, deletion, and/or insertion at one or more positions.

13. The polypeptide of any of paragraphs 1-12, which is a fragment of SEQ ID NO: 4 wherein the fragment has trehalase activity.

14. A composition comprising the polypeptide of any of paragraphs 1-13.

15. A whole broth formulation or cell culture composition comprising the polypeptide of any of paragraphs 1-14.

16. A polynucleotide encoding the polypeptide of any of paragraphs 1-14.

17. A nucleic acid construct or expression vector comprising the polynucleotide of paragraph 16 operably linked to one or more control sequences that direct the production of the polypeptide in an expression host.

18. A recombinant host cell comprising the polynucleotide of paragraph 16 operably linked to one or more control sequences that direct the production of the polypeptide.

19. A method of producing the polypeptide of any of paragraphs 1-14, comprising cultivating a cell, which in its wild-type form produces the polypeptide, under conditions conducive for production of the polypeptide.

20. The method of paragraph 19, further comprising recovering the polypeptide.

21. A method of producing a polypeptide having trehalase activity, comprising cultivating the host cell of paragraph 18 under conditions conducive for production of the polypeptide.

22. The method of paragraph 21, further comprising recovering the polypeptide.

23. A transgenic plant, plant part or plant cell transformed with a polynucleotide encoding the polypeptide of any of paragraphs 1-14.

24. A method of producing a polypeptide having trehalase activity, comprising cultivating the transgenic plant or plant cell of paragraph 21 under conditions conducive for production of the polypeptide.

25. The method of paragraph 24, further comprising recovering the polypeptide.

26. A process of producing a fermentation product, comprising
   (a) liquefying a starch-containing material with an alpha-amylase; optionally pre-saccharifying the liquefied material before step (b);
   (b) saccharifying the liquefied material;
   (c) fermenting using a fermentation organism;
   wherein
      i) a glucoamylase;
      ii) a trehalase of any of paragraphs 1-13;
      iii) optionally a cellulolytic enzyme composition and/or a protease;
   are present and/or added during
      saccharification step (b);
      fermentation step (c);
      simultaneous saccharification and fermentation;
      optionally presaccharification step before step (b).

27. The process of paragraph 26, wherein the alpha-amylase is a bacterial alpha-amylase, in particular of the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 18 herein.

28. The process of paragraph 27, wherein the *Bacillus stearothermophilus* alpha-amylase or variant thereof is truncated, preferably to be from 485-495 amino acids long, such as around 491 amino acids long.

29. The process of any of paragraphs 26 or 28, wherein the *Bacillus stearothermophilus* alpha-amylase has a double deletion at positions I181+G182, and optionally a N193F substitution, or deletion of R179+G180 (using SEQ ID NO: 18 for numbering).

30. The process of any of paragraphs 26-29, wherein the *Bacillus stearothermophilus* alpha-amylase has a substitution in position S242, preferably a S242A, E or Q substitution (using SEQ ID NO: 18 for numbering).

31. The process of any of paragraphs 26-30, wherein the *Bacillus stearothermophilus* alpha-amylase has a substitution in position E188, preferably E188P substitution (using SEQ ID NO: 18 for numbering).

32. The process of any of paragraphs 26-31, wherein the alpha-amylase in liquefaction step (a) is selected from the following group of *Bacillus stearothermophilus* alpha-amylase variants:
   I181*+G182*+N193F+E129V+K177L+R179E;
   I181*+G182*+N193F+V59A+Q89R+E129V+K177L+R179E+H208Y+K220P+N224L+Q254S
   I181*+G182*+N193F+V59A+Q89R+E129V+K177L+R179E+Q254S+M284V;
   I181*+G182*+N193F+V59A+E129V+K177L+R179E+Q254S+M284V and
   I181*+G182*+N193F+E129V+K177L+R179E+K220P+N224L+S242Q+Q254S (using SEQ ID NO: 18 herein for numbering).

33. The process of any of paragraphs 26-32, wherein the glucoamylase is of fungal origin, preferably from a strain of *Aspergillus*, preferably *A. niger*, *A. awamori*, or *A. oryzae*; or a strain of *Trichoderma*, preferably *T. reesei*; or a strain of *Talaromyces*, preferably *T. emersonii*, or a strain of *Gloeophyllum*, such as *G. serpiarium* or *G. trabeum*.

34. The process of any of paragraphs 26-33, wherein the glucoamylase is derived from *Talaromyces emersonii*, such as the one shown in SEQ ID NO: 13 herein.

35. The process of any of paragraphs 26-34, wherein the glucoamylase is selected from the group consisting of:
(i) a glucoamylase comprising the mature polypeptide of SEQ ID NO: 13 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 13 herein.

36. The process of any of paragraphs 26-35, wherein the glucoamylase is derived from *Gloeophyllum serpiarium*, such as the one shown in SEQ ID NO: 19 herein.

37. The process of any of paragraphs 26-36, wherein the glucoamylase is selected from the group consisting of:
(i) a glucoamylase comprising the mature polypeptide of SEQ ID NO: 19 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 19 herein.

38. The process of any of paragraphs 26-37, wherein the glucoamylase is derived from *Gloeophyllum trabeum* such as the one shown in SEQ ID NO: 20 herein.

39. The process of any of paragraphs 26-38, wherein the glucoamylase present and/or added in saccharification is selected from the group consisting of:
(i) a glucoamylase comprising the mature polypeptide of SEQ ID NO: 20 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 20 herein.

40. The process of any of paragraphs 26-39, further wherein an alpha-amylase is present and/or added during saccharification step (b); fermentation step (c); simultaneous saccharification and fermentation; or the optional presaccharification step before step (b).

41. The process of paragraph 40, wherein the alpha-amylase is of fungal or bacterial origin.

42. The process of paragraph 40 or 41, wherein the alpha-amylase is derived from a strain of the genus *Rhizomucor*, preferably a strain the *Rhizomucor pusillus*, such as the one shown in SEQ ID NO: 3 in WO 2013/006756, such as a *Rhizomucor pusillus* alpha-amylase hybrid having an *Aspergillus niger* linker and starch-bonding domain, such as the one shown in SEQ ID NO: 15 herein.

43. The process of any of paragraphs 40-42, wherein the alpha-amylase present and/or added in saccharification and/or fermentation is selected from the group consisting of:
(i) an alpha-amylase comprising the mature polypeptide of SEQ ID NO: 15 herein;
(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 15 herein.

44. The process of any of paragraphs 40-43, wherein the alpha-amylase is a variant of the alpha-amylase shown in SEQ ID NO: 15 having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 15 for numbering).

45. The process of any of paragraphs 36-44, wherein the alpha-amylase is derived from a *Rhizomucor pusillus*, in particular with an *Aspergillus niger* glucoamylase linker and starch-binding domain (SBD), preferably the one disclosed as SEQ ID NO: 15 herein, preferably having one or more of the following substitutions: G128D, D143N, preferably G128D+D143N (using SEQ ID NO: 15 for numbering).

46. The process of any of paragraphs 44-45, wherein the alpha-amylase variant has at least 60% identity, such as at least 70%, preferably at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 15 herein.

47. The process of any of paragraphs 26-46, wherein the cellulolytic enzyme composition is derived from *Trichoderma reesei*, *Humicola insolens* or *Chrysosporium lucknowense*.

49. The process of any of paragraphs 26-48, wherein the cellulolytic enzyme composition comprising a beta-glucosidase, a cellobiohydrolase, an endoglucanase and optionally a GH61 polypeptide.

50. The process of any of paragraph 26-49, wherein the cellulolytic enzyme composition comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigatus*, such as one disclosed in SEQ ID NO: 2 in WO 2005/047499 or SEQ ID NO: 10 herein or an *Aspergillus fumigatus* beta-glucosidase variant disclosed in WO 2012/044915; in particular an *Aspergillus fumigatus* beta-glucosidase variant with one or more, such as all, of the following substitutions: F100D, S283G, N456E, F512Y; or a strain of the genus a strain *Penicillium*, such as a strain of the *Penicillium brasilianum* disclosed in WO 2007/019442, or a strain of the genus *Trichoderma*, such as a strain of *Trichoderma reesei*.

51. The process of any of paragraphs 26-50, wherein the cellulolytic enzyme composition comprises a cellobiohydrolase I (CBH I), such as one derived from a strain of the genus *Aspergillus*, such as a strain of *Aspergillus fumigatus*, such as the Cel7a CBH I disclosed in SEQ ID NO: 6 in WO 2011/057140 or SEQ ID NO: 6 herein, or a strain of the genus *Trichoderma*, such as a strain of *Trichoderma reesei*.

52. The process of any of paragraphs 26-50, wherein the cellulolytic enzyme composition comprises a cellobiohydrolase II (CBH II, such as one derived from a strain of the genus *Aspergillus*, such as a strain of *Aspergillus fumigatus*; such as the one disclosed as SEQ ID NO: 8 herein or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

53. The process of any of paragraphs 26-52, wherein the cellulolytic enzyme composition further comprises a GH61 polypeptide having cellulolytic enhancing activity such as one derived from the genus *Thermoascus*, such as a strain of *Thermoascus aurantiacus*, such as the one described in WO 2005/074656 as SEQ ID NO: 2 or SEQ ID NO: 21 herein; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397 as SEQ ID NO: 2 or SEQ ID NO: 12 herein.

54. The process of any of paragraphs 26-54, wherein the cellulolytic enzyme composition is a *Trichoderma reesei* cellulolytic enzyme composition, further comprising *Ther-*

*moascus aurantiacus* GH61A polypeptide having cellulolytic enhancing activity (SEQ ID NO: 2 in WO 2005/074656 or SEQ ID NO: 21 herein) and *Aspergillus fumigatus* beta-glucosidase (SEQ ID NO: 2 of WO 2005/047499) or SEQ ID NO: 6 herein.

55. The process of any of paragraphs 26-54, wherein the cellulolytic enzyme composition is a *Trichoderma reesei* cellulolytic enzyme composition further comprising *Penicillium emersonii* GH61A polypeptide having cellulolytic enhancing activity disclosed in WO 2011/041397 as SEQ ID NO: 2 or SEQ ID NO: 12 herein; and *Aspergillus fumigatus* beta-glucosidase (SEQ ID NO: 2 of WO 2005/047499 or SEQ ID NO: 10 herein) or a variant thereof with one or more, such as all, of the following substitutions: F100D, S283G, N456E, F512Y.

56. The process of any of paragraphs 26-55, wherein the cellulolytic enzyme composition is dosed from 0.0001-3 mg EP/g DS, preferably 0.0005-2 mg EP/g DS, preferably 0.001-1 mg/g DS, more preferred from 0.005-0.5 mg EP/g DS, even more preferred 0.01-0.1 mg EP/g DS.

57. The process of any of paragraphs 26-56, wherein the presaccharification is carried out at a temperature from 40-75° C., such as 50-70° C., preferably 60° C.; a pH between 4-6, preferably 5; for a period of 30-360 minutes, such as from 60-420 minutes, such as around between 150-180 minutes.

58. A process of any of paragraphs 26-57, comprising the steps of:
(a) liquefying a starch-containing material with an alpha-amylase;
optionally pre-saccharifying the liquefied material before step (b);
(b) saccharifying the liquefied material;
(c) fermenting using a fermentation organism;
wherein
  i) a glucoamylase;
  ii) a trehalase of any of paragraphs 1-13;
are present and/or added during
  saccharification step (b);
  fermentation step (c);
  simultaneous saccharification and fermentation;
  optionally presaccharification step before step (b).

59. A process of any of paragraphs 26-58, comprising the steps of:
(a) liquefying a starch-containing material with an alpha-amylase;
optionally pre-saccharifying the liquefied material before step (b);
(b) saccharifying the liquefied material;
(c) fermenting using a fermentation organism;
wherein
  i) a glucoamylase from *Talaromyces emersonii* or *Gloeophyllum serpiarium;*
  ii) a trehalase shown in any of paragraphs 1-13;
are present and/or added during
  saccharification step (b);
  fermentation step (c);
  simultaneous saccharification and fermentation;
  optionally presaccharification step before step (b).

60. A process of any of paragraphs 26-58, comprising the steps of:
(a) liquefying a starch-containing material with an alpha-amylase;
optionally pre-saccharifying the liquefied material before step (b);
(b) saccharifying the liquefied material;
(c) fermenting using a fermentation organism;
wherein
  i) a glucoamylase from *Talaromyces emersonii* or *Gloeophyllum serpiarium;*
  ii) a trehalase shown any of paragraphs 1-13;
  iii) a cellulolytic enzyme composition derived from *Trichoderma reesei;*
are present and/or added during
  saccharification step (b);
  fermentation step (c);
  simultaneous saccharification and fermentation;
  optionally presaccharification step before step (b).

61. The process of any of paragraphs 26-60, wherein saccharification step (a) and fermentation step (b) are done separately or simultaneously.

62. The process of any of paragraphs 26-61, wherein the fermentation product is recovered after fermentation.

63. The process of any of paragraphs 26-62, wherein the starch-containing material is plant material selected from the corn (maize), cobs, wheat, barley, rye, milo, sago, cassava, tapioca, sorghum, rice, peas, beans, sweet potatoes, or a mixture thereof, preferably corn.

64. The process of any of paragraphs 26-63, wherein the temperature in liquefaction is above the initial gelatinization temperature, in particular in the range from 70-100° C., such as between 75-95° C., such as between 75-90° C., preferably between 80-90° C., such as 82-88° C., such as around 85° C.

65. The process of any of paragraphs 26-64, wherein liquefaction step (a) is carried out at a pH in the range between 3 and 7, preferably from 4 to 6, or more preferably from 4.5 to 5.5.

66. The process of any of paragraphs 26-65, wherein the dry solid content (DS) in liquefaction lies in the range from 20-55 wt.-%, preferably 25-45 wt.-%, more preferably 30-40 wt.-% or 30-45 wt.-%.

66. The process of any of paragraphs 26-65, further comprises, prior to the liquefaction step (a), the steps of:
x) reducing the particle size of the starch-containing material, preferably by dry milling;
y) forming a slurry comprising the starch-containing material and water.

67. The process of any of paragraphs 26-66, wherein a jet-cooking step is carried out prior to liquefaction in step (a).

68. The process of any of paragraphs 26-67, wherein the starch-containing material is reduced in particle size, such by dry milling or wet milling or using particle size emulsion technology.

69. The process of any of paragraphs 26-68, wherein the fermentation is carried out for 30 to 150 hours, preferably 48 to 96 hours.

70. The process of any of paragraphs 26-69, wherein the temperature during fermentation in step (b) or simultaneous saccharification and fermentation in steps (a) and (b) is between 25° C. and 40° C., preferably between 28° C. and 36° C., such as between 28° C. and 35° C., such as between 28° C. and 34° C., such as around 32° C.

71. The process of any of paragraphs 26-70, wherein further a protease is present during saccharification and/or fermentation.

72. The process of any of paragraphs 26-71, wherein glucoamylase is present and/or added in an amount of 0.001 to 10 AGU/g DS, preferably from 0.01 to 5 AGU/g DS, especially 0.1 to 0.5 AGU/g DS.

73. The process of any of paragraphs 26-72, wherein the fermentation product is an alcohol, preferably ethanol, especially fuel ethanol, potable ethanol and/or industrial ethanol.

74. The process of any of paragraphs 26-73, further wherein a protease is present and/or added during
- saccharification step (b);
- fermentation step (c);
- simultaneous saccharification and fermentation;
- optionally presaccharification step before step (b).

75. The process of any of paragraphs 26-74, wherein the protease is derived from Thermoascus, in particular *Thermoascus aurantiacus*, especially *Thermoascus aurantiacus* CGMCC No. 0670 (classified as EC 3.4.24.39) shown in SEQ ID NO: 17 herein.

76. The process of paragraph 75, wherein the protease is the one shown in SEQ ID NO: 17 herein or a protease being at least 60%, such as at least 70%, such as at least 80%, such as at least 90%, such as at least 95%, such as at least 96%, such as at least 97%, as as at least 98%, such as at least 99% identical to SEQ ID NO: 17 herein.

77. The process of any of paragraphs 26-74, wherein the protease is derived from a strain of *Meripilus*, in particular *Meripilus giganteus*, in particular the one shown as SEQ ID NO: 32 herein.

78. The process of paragraph 77, wherein the protease is the one shown in SEQ ID NO: 32 herein or a protease being at least 60%, such as at least 70%, such as at least 80%, such as at least 90%, such as at least 95%, such as at least 96%, such as at least 97%, as as at least 98%, such as at least 99% identical to SEQ ID NO: 32 herein.

79. The process of any of paragraphs 26-78, wherein the fermenting organism is derived from a strain of Saccharomyces, such as *Saccharomyces cerevisae*.

80. A process of producing fermentation products from starch-containing material comprising:
   (i) saccharifying a starch-containing material at a temperature below the initial gelatinization temperature; and
   (ii) fermenting using a fermentation organism;
   wherein saccharification and/or fermentation is done in the presence of the following enzymes: glucoamylase, alpha-amylase, trehalase of any of paragraphs 1-13, and optionally a protease and/or a cellulolytic enzyme composition.

81. A process of producing a fermentation product from pretreated cellulosic material, comprising:
   (a) hydrolyzing said pretreated cellulosic material with a cellulolytic enzyme composition;
   (b) fermenting using a fermenting organism; and
   (c) optionally recovering the fermentation product,
   wherein a trehalase of any of paragraphs 1-13 is added and/or present in hydrolysis step (a) and/or fermentation step (b).

82. The process of any of paragraphs 26-81, wherein the trehalase is added in an amount between 0.01-20 ug EP trehalase/g DS, such as between 0.05-15 ug EP terhalase/g DS, such as between 0.5 and 10 ug EP trehalase/g DS.

83. The process of any of paragraphs 81-82, wherein the cellulolytic enzyme composition is derived from *Trichoderma reesei, Humicola insolens* or *Chrysosporium lucknowense*.

84. The process of any of paragraphs 81-83, wherein the cellulolytic enzyme composition comprising a beta-glucosidase, a cellobiohydrolase, an endoglucanase and optionally a GH61 polypeptide.

85. The process of any of paragraph 81-84, wherein the cellulolytic enzyme composition comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigatus*, such as one disclosed in SEQ ID NO: 2 in WO 2005/047499 or SEQ ID NO: 10 herein or an *Aspergillus fumigatus* beta-glucosidase variant disclosed in WO 2012/044915; in particular an *Aspergillus fumigatus* beta-glucosidase variant with one or more, such as all, of the following substitutions: F100D, S283G, N456E, F512Y; or a strain of the genus a strain *Penicillium*, such as a strain of the *Penicillium brasilianum* disclosed in WO 2007/019442, or a strain of the genus *Trichoderma*, such as a strain of *Trichoderma reesei*.

86. The process of any of paragraphs 81-85, wherein the cellulolytic enzyme composition comprises a cellobiohydrolase I (CBH I), such as one derived from a strain of the genus *Aspergillus*, such as a strain of *Aspergillus fumigatus*, such as the Cel7a CBH I disclosed in SEQ ID NO: 6 in WO 2011/057140 or SEQ ID NO: 6 herein, or a strain of the genus *Trichoderma*, such as a strain of *Trichoderma reesei*.

87. The process of any of paragraphs 81-86, wherein the cellulolytic enzyme composition comprises a cellobiohydrolase II (CBH II, such as one derived from a strain of the genus *Aspergillus*, such as a strain of *Aspergillus fumigatus*; such as the one disclosed as SEQ ID NO: 8 herein or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

88. The process of any of paragraphs 81-87, wherein the cellulolytic enzyme composition further comprises a GH61 polypeptide having cellulolytic enhancing activity such as one derived from the genus *Thermoascus*, such as a strain of *Thermoascus aurantiacus*, such as the one described in WO 2005/074656 as SEQ ID NO: 2 or SEQ ID NO: 21 herein; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397 as SEQ ID NO: 2 or SEQ ID NO: 12 herein.

89. The process of any of paragraphs 81-88, wherein the cellulolytic enzyme composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656 or SEQ ID NO: 21 herein) and *Aspergillus fumigatus* beta-glucosidase (SEQ ID NO: 2 of WO 2005/047499) or SEQ ID NO: 6 herein.

90. The process of any of paragraphs 81-89, wherein the cellulolytic enzyme composition is a *Trichoderma reesei* cellulolytic enzyme composition further comprising *Penicillium emersonii* GH61A polypeptide having cellulolytic enhancing activity disclosed in WO 2011/041397 as SEQ ID NO: 2 or SEQ ID NO: 12 herein; and *Aspergillus fumigatus* beta-glucosidase (SEQ ID NO: 2 of WO 2005/047499 or SEQ ID NO: 10 herein) or a variant thereof with one or more, such as all, of the following substitutions: F100D, S283G, N456E, F512Y.

91. The process of any of paragraphs 81-90, wherein the cellulolytic enzyme composition is dosed from 0.0001-3 mg EP/g DS, preferably 0.0005-2 mg EP/g DS, preferably 0.001-1 mg/g DS, more preferred from 0.005-0.5 mg EP/g DS, even more preferred 0.01-0.1 mg EP/g DS.

The invention claimed is:

1. A process of producing a fermentation product, comprising steps:
   (a) liquefying a starch-containing material with an bacterial alpha-amylase;
   (b) saccharifying the starch-containing liquefied material; and
   (c) fermenting the starch-containing liquefied material from step (b) using yeast as a fermentation organism in a fermentation reaction, wherein the fermentation reaction comprises an enzymatic composition which comprises: i) a fungal glucoamylase, and ii) a fungal alpha amylase, and a polypeptide having trehalase activity, wherein the polypeptide having trehalase activity is having at least 95% amino acid sequence identity to the amino acid sequence of the mature polypeptide of SEQ ID NO: 30, and wherein said mature polypeptide of SEQ ID NO: 30 consists the amino acid sequence from position 21 to position 694 of the amino acid sequence as set forth in SEQ ID NO: 30.

2. The process of producing a fermentation product according to claim 1, wherein the process comprises pre-saccharifying the starch-containing liquefied material before step (b).

3. The process of producing a fermentation product according to claim 1, wherein said enzymatic composition is present or added during said saccharification step (b), or said fermentation step (c).

4. The process of producing a fermentation product according to claim 2, wherein said enzymatic composition is present or added during said pre-saccharification.

5. The process of producing a fermentation product according to claim 1, wherein said mature polypeptide of SEQ ID NO: 30 is encoded by a polynucleotide having at least 90% nucleotide sequence identity to the mature polypeptide SEQ ID NO: 30 coding nucleotide sequence as set forth in SEQ ID NO: 29.

6. The process of claim 1, wherein the polypeptide having trehalase activity has the amino acid sequence of the mature polypeptide of SEQ ID NO: 30.

7. The process of claim 1, wherein the fermentation reaction further comprises a serine protease or metallo protease.

8. The process of claim 1, wherein the fermentation reaction further comprises a cellulolytic composition comprising fungal cellulases.

9. The process of claim 8, wherein the cellulolytic composition comprises a *Penicillium emersonii* GH61A polypeptide.

10. The process of claim 8, wherein the cellulolytic composition comprises an *Aspergillus fumigatus* beta-glucosidase.

11. The process of claim 8, wherein the cellulolytic composition comprises an *Aspergillus fumigatus* cellobiohydrolase.

12. The process of claim 11, wherein the *Aspergillus fumigatus* cellobiohydrolase is a cellobiohydrolase I (CBHI).

13. The process of claim 11, wherein the *Aspergillus fumigatus* cellobiohydrolase is a cellobiohydrolase II (CBHII).

14. The process of claim 8, wherein the cellulolytic composition comprises an *Aspergillus fumigatus* cellobiohydrolase I (CBHI) and an *Aspergillus fumigatus* cellobiohydrolase II (CBHII).

* * * * *